(12) United States Patent
Debinski et al.

(10) Patent No.: US 9,974,830 B2
(45) Date of Patent: May 22, 2018

(54) MOLECULAR SIGNATURE OF CANCER

(71) Applicant: Wake Forest University Health Sciences, Winston-Salem, NC (US)

(72) Inventors: Waldemar Debinski, Winston-Salem, NC (US); Jill Wykosky, LaJolla, CA (US); Denise Mazess Herpai, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days. days.

(21) Appl. No.: 15/018,991

(22) Filed: Feb. 9, 2016

(65) Prior Publication Data

US 2016/0193289 A1 Jul. 7, 2016

Related U.S. Application Data

(60) Division of application No. 13/692,324, filed on Dec. 3, 2012, now Pat. No. 9,290,558, which is a division of application No. 12/201,662, filed on Aug. 29, 2008, now Pat. No. 8,343,461, which is a continuation-in-part of application No. PCT/US2007/005964, filed on Mar. 8, 2007.

(60) Provisional application No. 61/041,397, filed on Apr. 1, 2008, provisional application No. 60/780,241, filed on Mar. 8, 2006.

(51) Int. Cl.

| A61K 47/48 | (2006.01) |
|---|---|
| A61K 38/17 | (2006.01) |
| A61K 49/00 | (2006.01) |
| C07K 14/52 | (2006.01) |
| A61K 38/20 | (2006.01) |
| A61K 45/06 | (2006.01) |
| C07K 14/705 | (2006.01) |
| A61K 38/45 | (2006.01) |
| A61K 47/64 | (2017.01) |
| A61K 47/68 | (2017.01) |
| A61K 38/00 | (2006.01) |

(52) U.S. Cl.
CPC ........ *A61K 38/177* (2013.01); *A61K 38/2086* (2013.01); *A61K 38/45* (2013.01); *A61K 45/06* (2013.01); *A61K 47/64* (2017.08); *A61K 47/642* (2017.08); *A61K 47/6801* (2017.08); *A61K 49/0002* (2013.01); *C07K 14/52* (2013.01); *C07K 14/705* (2013.01); *A61K 38/00* (2013.01); *C12Y 204/02036* (2013.01)

(58) Field of Classification Search
CPC .............. A61K 38/177; A61K 47/48
USPC ............... 424/193.1, 185.1, 184.1
See application file for complete search history.

(56) References Cited

U.S. PATENT DOCUMENTS

| 5,328,984 | A | 7/1994 | Pastan et al. |
|---|---|---|---|
| 5,919,456 | A | 7/1999 | Puri et al. |
| 6,296,843 | B1 | 10/2001 | Debinski |
| 2004/0180823 | A1 | 9/2004 | Pasquale et al. |
| 2005/0147593 | A1 | 7/2005 | Kinch et al. |
| 2005/0153923 | A1 | 7/2005 | Kinch |
| 2005/0249736 | A1 | 11/2005 | Krasnoperov et al. |
| 2006/0121043 | A1 | 6/2006 | Kinch et al. |
| 2006/0121539 | A1 | 6/2006 | Debinski et al. |
| 2006/0122138 | A1 | 6/2006 | Kinch et al. |
| 2006/0177452 | A1 | 8/2006 | Pasquale et al. |

FOREIGN PATENT DOCUMENTS

| WO | WO 02/02799 A1 | 1/2002 |
|---|---|---|
| WO | WO 03/004057 A1 | 1/2003 |
| WO | WO 2005/042028 A2 | 5/2005 |
| WO | WO 2006/047298 A2 | 5/2006 |

OTHER PUBLICATIONS

Harlow E and Lane D. Antibodies, a Laboratory Manual, Cold Spring Harbor Laboratory Press. 1988, pp. 591-592.
Bowie Ju et al, Deciphering the message in protein sequences: tolerant to amino acid substitutions. Science. 1990; 257: 1306-1310.
Burgess WH et al. Activities of heparin-binding (acidic fibroblast) growth factor-1 from its receptor-binding activities by site-directed mutagenesis of a single lysine residue. Journal of Cell Biology. Nov. 1990; 111: 2129-2138.
Lazar E et al. Transforming growth factor alpha: mutation of aspartic acid 47 and leucine 48 results in different biological activities. Molecular and Cell Biology. Mar. 1988; 8(3): 1247-1252.
AAH32698.1 (Ephrin A1 [*Homo sapiens*] Jun. 2002).
MeSH (glioblastoma, 1994).
International Search Report and Written Opinion, PCT/US07/05964, dated Oct. 1, 2007.
Raza SM et al, Identification of necrosis-associated genes in glioblastomas by cDNA microarray analysis. Clinical Cancer Research. Jan. 1, 2004; 10: 212-221.
Carles-Kinch K et al. Antibody targeting of the EphA2 tyrosine kinase inhibits malignant cell behavior. Cancer Research. May 15, 2002; 62: 2840-2847.
Davis S et al. Ligands for EPH-related receptor tyrosine kinases that require membrane attachment or clustering for activity, Science. Nov. 4, 1994; 266: 816-819.
Duxbury MS et al. EphA2: a determinant of malignant cellular behavior and a potential therapeutic target in pancreatic adenocarcinoma. Oncogene. 2004; 23: 1448-1456.
Holzman LB et al. A novel immediate-early response gene of endothelium is induced by cytokines and encodes a secreted protein. Molecular and Cellular Biology. Nov. 1990; 10(11): 5830-5838.
Koolpe M et al. An ephrin mimetic peptide that selectively targets the EphA2 receptor. The Journal of Biological Chemistry, Dec. 6, 2002; 277(49): 46974-46979.
Landen Jr, CN et al, Therapeutic EphA2 gene targeting in vivo using neutral liposomal small interfering RNA delivery. Cancer Res. 2005; 65(15): 6910-6918.

(Continued)

*Primary Examiner* — Yan Xiao
(74) *Attorney, Agent, or Firm* — Myers Bigel, P.A.

(57) ABSTRACT

The present invention provides compounds, compositions, and methods for detecting, diagnosing and treating cancers such as glioblastoma multiforme.

9 Claims, 32 Drawing Sheets

(56) References Cited

OTHER PUBLICATIONS

Wykosky J et al. EphA2 as a novel molecular marker and target in glioblastoma multiforme, Mol Cancer Res. Oct. 2005; 3(10): 541-551.
Supplementary European Search Report, EP 07 75 2648, completed May 7, 2009.
Bartley TD et al. B61 is a ligand for the ECK receptor protein-tyrosine kinase. Nature. Apr. 7, 1994; 368: 558-560.
Flanagan JG and Vanderhaeghen P. The ephrins and EPH receptors in neural development. Annual Review of Neuroscience. 1998; 21: 309-345.
Whitlock K. Glioma: studies offer new drug targets. Oncology Times. Sep. 25, 2005: 25-27.
Duxbury MS et al. Ligation of EphA2 by Ephrin A1-Fc inhibits pancreatic adenocarcinoma cellular invasiveness. Biochemical and Biophysical Research CommunicationS. 2004; 320: 1096-1102.
SIGMA product information. Product No. E 7902: EphA1 Extracellular Domain/Fc Chimera, Human, Recombinant, Expressed in NSO mouse myeloma cells. Sigma-Aldrich, Inc., Saint Louis, Missouri. 2 pages.
Flanagan JG and Vanderhaeghen P. The ephrins and EPH receptors in neural development. Ann. Rev. Neurosci. 1998; 21: 309-45.
Wykosky J et al. Soluble monomeric EphrinA1 is released from tumor cells and is a functional ligand for the EphA2 receptor. Oncogene. 2008; 27: 7260-7273.
R&D Systems product information. Catalog No. 602-A1: Recombinant Mouse Ephrin-A1 Fc Chimera. R&D Systems, Inc., Minneapolis, Minnesota, 1 page.
SIGMA product information. Product No. E 9902: Ephrin-A1 Extracellular Domain/Fc Chimera, Mouse, Recombinant, Expressed in NSO mouse myeloma cells. Sigma-Aldrich, Inc., Saint Louis, Missouri. 2 pages.

MOLECULAR SIGNATURE OF CANCER

RELATED APPLICATIONS

This application is a divisional of and claims priority to U.S. patent application Ser. No. 13/692,324, filed Dec. 3, 2012, now allowed, which is a divisional of U.S. patent application Ser. No. 12/201,662, filed Aug. 29, 2008, now U.S. Pat. No. 8,343,461, which claims the benefit under 35 U.S.C. § 119(e) of U.S. Provisional Patent Application No. 61/041,397, filed Apr. 1, 2008, and also is a Continuation-in-Part and claims the benefit under 35 U.S.C. § 120 of PCT International Application No. PCT/US2007/005964, filed Mar. 8, 2007 and published in English under PCT Article 21(2), which claims priority to U.S. Provisional Patent Application No. 60/780,241, filed Mar. 8, 2006; the entire contents of all of these applications are incorporated herein by reference.

GOVERNMENT FUNDING

This was made, in part, with United States government support under grant numbers RO1 CA 741451 and F31 NSO55533-01 from the National Institutes of Health. The United States government has certain rights to this invention.

STATEMENT REGARDING ELECTRONIC FILING OF A SEQUENCE LISTING

A Sequence Listing in ASCII text format, submitted under 37 C.F.R. § 1.821, entitled 9151-106IP.ST25.txt, 35,890 bytes in size, generated on Aug. 28, 2008 and filed via EFS-Web, is provided in lieu of a paper copy. This Sequence Listing is hereby incorporated by reference into the specification for its disclosures.

FIELD OF THE INVENTION

The present invention concerns compounds, compositions, and methods for detecting, diagnosing and treating cancers such as glioblastoma multiforme.

BACKGROUND OF THE INVENTION

Cancer is now the number one cause of death in North America. Malignant tumors of the central nervous system (CNS) are the third leading cause of cancer-related deaths in adolescents and adults between the ages of 15 and 34, and in children, brain tumors are the leading cause of cancer death. Furthermore, the two-year survival rate for patients with glioblastoma multiforme (GBM), a high-grade glioma (HGG), grade IV, is less than 20% (Davis et al. (1998) J. Neurosurg. 88:1-10), and there has been a steady increase in the incidence of brain cancers during the last 20 years ("Reports from the front" (1995) Science 267:1414). Almost any cancer can metastasize to the CNS (Olson et al. (1974) Arch. Neurol. 30:122-136).

A common approach to the treatment of malignant gliomas involves surgery (Berger (1994) Sem. Oncol. 21:172-185), radiation therapy (Gunderson & Tepper, Eds. (2000) Clinical Radiation Oncology (Churchill-Livingstone, Philadelphia), pp 314-35), and various chemotherapeutic regimens (Lesser & Grossman (1994) Sem. Oncol. 21:220-235), but neither single nor multimodal treatments are curative. At present, treatment is implemented to improve or sustain neurological function of the patient, to diminish the size of the tumor growing intracranially, and to lengthen intervals between treatments. Thus, new and molecular-specific methods of HGG treatment are urgently needed.

The transmembrane protein EphA2 is overexpressed and an attractive molecular target in glioblastoma multiforme (GBM), the most common primary brain tumor, which has a high incidence of recurrence and dim prognosis (Wykosky et al. (2005) Mol. Cancer Res. 3:541-551). Only 3% of patients survive five years, with a median survival of approximately 14 months (Davis et al. (1998) J. Neurosurg. 88:1-10; Stupp et al. (2005) N. Engl. J. Med. 352:987-996). Interestingly, ephrinA1, a ligand for EphA2, is virtually not detectable in GBM cell lines, and is present at low levels in the majority of specimens despite the abundant overexpression of the receptor (Wykosky et al. (2005) Mol. Cancer Res. 3:541-551). A similar pattern of differential EphA2/ephrinA1 expression has been reported in breast cancer (Macrae et al. (2005) Cancer Cell 8:111-118).

The ephrins comprise a family of protein ligands for the Eph receptor tyrosine kinases, and are unique among ligands for receptor tyrosine kinases in that they have been described as GPI-linked (ephrinA) or transmembrane (ephrinB) cell surface proteins rather than soluble factors (Davis et al. (1994) Science 266:816-819). Hence, it has been widely accepted that endogenous activation of Eph receptors by their ephrin ligands requires stable cell-cell contact and/or clustering by ephrin ligands (Shao et al. (1995) J. Biol. Chem. 270:5636-5641; Stein et al. (1998) Genes Dev. 12:667-678).

The physiological role of ephrins and Eph receptors lies primarily in the formation and organization of the vasculature (McBride et al. (1998) Mech. Dev. 77:201-204; Wang et al. (1998) Cell 93:741-753) and the patterning of topographic maps in the developing retinotectal and central nervous systems, where Eph signaling transmits cues for axon guidance (Drescher et al. (1995) Cell 82:359-370; Nakamoto et al. (1996) Cell 86:755-766; Knoll et al. (2002) Trends Neurosci. 25:145-149; Rashid et al. (2005) Neuron 47:57-69). Furthermore, some Eph receptors, including EphA2 and EphB2 (Nakada et al. (2004) Cancer Res. 64:3179-3185), have been implicated in tumorigenesis. Specifically, the EphA2 receptor is overexpressed and functionally important in cancers of the breast (Zelinski et al. (2001) Cancer Res. 61:2301-2306; Wu et al. (2004) Pathol. Oncol. Res. 10:26-33), prostate (Walker-Daniels et al. (1999) Prostate 41:275-280; Zeng et al. (2003) Am. J. Pathol. 163:2271-2276), brain (Wykosky et al. (2005) Mol. Cancer Res. 3:541-551; Hatano et al. (2005) Neoplasia 7:717-722), and ovary (Thaker et al. (2004) Clin. Cancer Res. 10:5145-5150).

Due to the absence of the receptor in normal brain, opportunities exist for EphA2-targeted therapies based on ephrinA1, similar in high GBM cell molecular-specificity to what has been shown previously for another glioma-associated antigen, IL-13 receptor alpha-2 (Debinski et al. (1998) Nat. Biotechnol. 16:449-453). Interestingly, the ligand for EphA2, ephrinA1, is on average expressed (i) at lower levels when the receptor is elevated, and (ii) at higher levels when the receptor is low. Hence, it was hypothesized that ephrinA1 is a tumor-suppressing protein in several solid tumors. Furthermore, a soluble recombinant homodimer, ephrinA1-Fc, activates EphA2 in GBM and other tumor cells, resulting in alteration of their malignant features. However, the prevailing notion has been that ephrinA1 must be anchored to the plasma membrane and form a oligodimer in order to activate EphA2 in malignancy.

Previously, the tumor-suppressing potential of ephrinA1 has been demonstrated using, e.g., a recombinant, covalently-linked homodimeric ephrinA1-Fc. This protein activates and reverses the oncogenic properties of EphA2 in tumor cells in culture, causing receptor down-regulation, cell morphology changes, suppression of integrin function, and negative regulation of invasion, migration, and anchorage-independent growth (Wykosky et al. (2005) Mol. Cancer Res. 3:541-551); (Miao et al. (2000) Nat. Cell Biol. 2:62-69; Carter (2002) Nat. Cell Biol. 4:565-573; Walker-Daniels et al. (2002) Mol. Cancer Res. 1:79-87; Duxbury et al. (2004) Biochem. Biophys. Res. Commun. 320:1096-1102). The known physiological roles of ephrinA1, also thought to be mediated by a membrane-anchored form of the ligand and dependent on cell-cell contact, include induction of cell repulsion and growth cone collapse during central nervous system development (Marquardt et al. (2005) Cell 121:127-139). In addition, ephrinA1 has been shown to be expressed in the developing vasculature during embryogenesis (McBride et al. (1998) Mech. Dev. 77:201-204), induces endothelial cell migration (Pandey et al. (1995) Science 268:567-569) and the formation of capillary-like structures in vitro (Daniel et al. (1996) Kidney Int. Suppl 57:S73-S81), and plays a role in angiogenesis and neovascularization in vivo (Cheng et al. (2002) Mol. Cancer Res. 1:2-11).

EphrinA1 was originally isolated as a TNF-α-inducible, immediate-early response gene product from normal human umbilical vein endothelial cells (Holzman et al. (1990) Mol. Cell Biol. 10:5830-5838). The full-length mature protein is composed of 187 amino acids with a molecular weight of 22 kDa. The C-terminus of ephrinA1, due to its hydrophobic nature interrupted by several charged amino acids extending to the extreme C-terminal end, has high structural similarity to GPI-linked, membrane-anchored proteins (Ferguson et al. (1988) Annu. Rev. Biochem. 57:285-320). Interestingly, however, the original study did not provide evidence for its presence on the surface of normal endothelial cells. It was only later demonstrated that the ligand may exist as a GPI-linked protein in ephrinA1-transfected human embryonic kidney and breast cancer cells by its release into the media upon proteolytic cleavage with phosphatidylinositol-specific phospholipase C (PI-PLC) (Shao et al. (1995) J. Biol. Chem. 270:5636-5641). Additional indirect support for the membrane-anchored presence of the ligand was in the finding that soluble ephrinA1 could activate the EphA5 receptor only when clustered by antibodies against C-terminal epitope tags (Davis et al. (1994) Science 266:816-819).

These observations, coupled with structural studies on active Eph/ephrin complexes (Himanen et al. (2001) Nature 414:933-938; Toth et al. (2001) Dev. Cell 1:83-92), gave rise to the notion that clustering of ephrins is a process necessary for Eph receptor activation that can be accomplished in a number of ways: via membrane attachment (Davis et al. (1994) Science 266:816-819; Shao et al. (1995) J. Biol. Chem. 270:5636-5641), antibody-mediated clustering (Davis et al. (1994) Science 266:816-819), or the formation of soluble homodimers through disulfide bonding of an IgG-Fc conjugate (Stein et al. (1998) Genes Dev. 12:667-678). Hence, membrane-bound ephrinA1 is considered the endogenous, functional form of the ligand (Beckmann et al. (1994) EMBO J. 13:3757-3762; Xu et al. (1997) J. Mol. Med. 75:576-586; Kullander et al. (2002) Nat. Rev. Mol. Cell Biol. 3:475-486; Pasquale (2005) Nat. Rev. Mol. Cell Biol. 6:462-475). The majority of studies on the role of ephrinA1 and other ephrinA's, both in physiology and in tumorigenesis, employ the Fc-conjugated dimeric forms of the ligand, often pre-clustered by the addition of IgG (Davis et al. (1994) Science 266:816-819; Daniel et al. (1996) Kidney Int. Suppl. 57:S73-S81).

There remains a need to simplify and more efficiently utilize ephrinA1, e.g., for its anti-tumor activity.

SUMMARY OF THE INVENTION

A first aspect of the present invention is ephrinA1 in monomeric form. The ephrinA1 is preferably isolated, recombinant ephrinA1.

A second aspect of the present invention is a composition comprising, consisting of or consisting essentially of ephrinA1 in monomeric form in (and preferably solubilized in) a pharmaceutically acceptable carrier, e.g., an aqueous carrier.

A third aspect of the present invention is a method of detecting a cancer tumor expressing the oncogenic receptor EphA2 in a subject, comprising: administering ephrinA1 in monomeric form to said subject, wherein said ephrinA1 is coupled to a detectable group, and then detecting said detectable group at said tumor in said subject.

A fourth aspect of the present invention is a method of treating a cancer expressing the oncogenic receptor EphA2 in a subject, comprising: administering ephrinA1 in monomeric form to said subject in a treatment effective amount, wherein said ephrinA1 is coupled to a therapeutic agent.

A fifth aspect of the present invention is a method of treating cancer in a subject in need thereof, comprising administering a first compound that specifically binds to Eph receptors to said subject in a treatment effective amount, wherein said first compound is coupled to a first therapeutic agent, and concurrently administering a second compound that specifically binds to IL-13 receptors (IL-13R) to said subject in a treatment effective amount, wherein said second compound is coupled to a second therapeutic agent. In some embodiments, the Eph receptors are EphA2, and the IL-13 receptors are IL-13Rα2.

A particular aspect of the invention is a method of treating cancer in a subject, comprising: administering the subject a first compound that specifically binds to an Eph receptor to the subject in a treatment effective amount, wherein the first compound is coupled to a first therapeutic agent, and concurrently administering the subject a second compound that specifically binds to an IL-13 receptor (IL-13R) to the subject in a treatment effective amount, wherein the second compound is coupled to a second therapeutic agent. In some embodiments, the first compound comprises ephrinA1. In some embodiments, the first compound consists essentially of monomeric ephrinA1. In some embodiments, the second compound comprises IL-13, or anti-IL-13Rα2 antibody or peptide. In some embodiments, the method further comprises concurrently administering a third compound comprising a Frataxin-1 (Fra-1) antagonist to the subject in a treatment effective amount, wherein the third compound is coupled to a third therapeutic agent. In some embodiments, the cancer is selected from the group consisting of breast cancer, colorectal cancer, head and neck cancer, thyroid cancer, malignant gliomas, and prostate cancer, such as glioblastoma multiforme.

A further aspect of the invention is a composition comprising or consisting essentially of, together in a pharmaceutically acceptable carrier: a first compound that specifically binds to an Eph receptor in a subject in a treatment effective amount, wherein the first compound is coupled to a therapeutic agent, a second compound that specifically binds to an IL-13R in a subject in a treatment effective amount, wherein the second compound is coupled to a therapeutic agent, and, optionally but in some embodiments preferably, a third compound comprising a Fra-1 antagonist in a treatment effective amount, wherein the third compound is coupled to a therapeutic group. In some embodiments the first compound comprises ephrinA1; in some embodiments the first compound consists essentially of monomeric ephrinA1. In some embodiments the second compound comprises IL-13 or anti-IL-13Rα2 antibody or peptide.

A further aspect of the present invention is the use of ephrinA1 as described herein, or the combination of such ephrinA1 and another therapeutic agent such as IL-13 (and its mutants) as described herein, for the preparation of a medicament for use in detecting, diagnosing or treating a cancer as described herein.

The foregoing and other objects and aspects of the present invention are explained in greater detail in the specification set forth below.

BRIEF DESCRIPTION OF THE DRAWINGS

FIG. 1A. Western blot of confluent parental, mock- and ephrinA1-transfected U-251 MG GBM cells. Three individual ephrinA1-expressing clones are shown (#4, #7, #12). FIG. 1B. Light microscopy of U-251[ephrinA1](+) #7, #12, and SK-BR-3 breast cancer cells plated at high and low density. FIG. 1C. Western blot of EphA2 in high density mock-transfected cells and in low and high density U-251 [ephrinA1](+)#7, #12, and SK-BR-3 cells.

FIG. 2A. Western blot of ephrinA1 immunoreactivity in media obtained from parental U-251 MG, mock, U-251[ephrinA1](+) #4, #7, #12, and SK-BR-3 cells, all subject to reducing conditions. FIG. 2B. Western blot of ephrinA1 immunoreactivity in media obtained from parental U-251 MG, mock, and U-251[ephrinA1](+) #4 and #7 cells under non-reducing conditions.

FIG. 3A. Light microscopy of U-251 MG cells after treatment for 30 min with conditioned media obtained from parental, mock, and U-251[ephrinA1](+) #4, #7, and #12 cells. FIG. 3B. Light microscopy of U-251 MG cells after treatment for 15 min with U-251[ephrinA1](+) #12 media. 100 μL or 1000 μL of conditioned media was diluted to a final volume of 10 mL with serum-free growth media or undiluted (10000 μL). Parental and mock-conditioned media were undiluted. FIG. 3C. F-actin staining of U-251 MG cells treated with 1 μg/mL of ephrinA1-Fc or IgG control for the indicated times.

FIG. 4A. Western blot of EphA2 immunoreactivity in U-251 MG cells treated for 1 hr with conditioned media from parental U-251 MG, mock, and U-251[ephrinA1](+) #4, #7, and #12 cells. FIG. 4B. Western blot of EphA2 immunoreactivity in U-251 MG cells treated with U-251[ephrinA1](+) #4 media or 1 μg/mL ephrinA1-Fc for the indicated times.

FIG. 5A. Western blotting of total cell lysates for phosphorylated-ERK (p-ERK), total ERK, and β-Actin following treatment with media obtained from U-251 ephrinA1[+] #4 cells. FIG. 5B. Western blotting for p-ERK, total ERK, and β-Actin following treatment with 1 μg/ml ephrinA1-Fc. Densitometry revealed the fold change in p-ERK expression normalized to total ERK for each timepoint. FIG. 5C. Colony formation in soft agar of parental, mock-, and U-251ephrinA1[+] #4 and #12 cells as well as parental U-251 MG cells treated with 1 μg/mL ephrinA1-Fc. Colonies consisting of more than 50 cells were counted. **, p<0.001 vs. Mock, Bonferroni's Multiple Comparison Test.

FIG. 6A. Western blotting under non-reducing conditions of conditioned media from parental U-251 MG, mock-transfected, U-251[His-ephrinA1](+) #1 and #11 cells, and of pure His-ephrinA1 protein isolated from the conditioned media of [ephrinA1](+) #11 cells. FIG. 6B. Light microscopy of U-251 MG cells treated for 1 hour with less than 0.5 μg/mL His-ephrinA1 protein. Photographs taken with a 10× objective (left panels) or 20× objective lens (right panels). Controls were treated with an equal volume of vehicle (column elution buffer). FIG. 6C. SDS-PAGE analysis of non-reduced and reduced (DTT/IA) ephrinA1-Fc showing the relative sizes of dimeric versus monomeric ephrinA1-Fc used to treat U-251 MG cells. FIG. 6D. Phosphotyrosine (p-Tyr) and EphA2 detected by western blotting following immunoprecipitation with EphA2 in U-251 MG cells treated with dimeric or monomeric ephrinA1-Fc or IgG, PBS, or DTT/IA. Densitometry analysis revealed the relative density of phosphorylated EphA2 compared to total EphA2. FIG. 6E. Light microscopy of U-251 MG cells treated with 1 μg/mL dimeric or monomeric ephrinA1-Fc, IgG, or PBS. FIG. 6F. Migration assay measuring the percent wound closure over time of U-251 MG cells in the presence of dimeric or monomeric ephrinA1-Fc. **, p<0.001 vs. IgG-treated cells, Bonferroni's Multiple Comparison Test.

FIG. 8A. DT390-ephrin A1 is a major bacterial protein upon induction with IPTG. I, molecular size markers; II, pre-induced lysated of cells; III, IPTG-induced production of DT390-ephrin A1 in bacteria (lanes I to III represent SDS-PAGE); IV, western blot using anti-ephrinA1 antibody of partially purified DT390-ephrinA1 cytotoxin. FIG. 8B. Cell proliferation assay in U-215 MG GBM cells using DT390-ephrinA1 (15 nM) in the absence or presence of an excess of ephrinA1-Fc.

FIG. 10A, Frequency of IL-13Rα2, EphA2, or Fra-1 expression. Tissue sections stained for IL-13Rα2, EphA2, or Fra-1 were analyzed and placed into one of three categories based on the average percent of positive-staining cells/section: 0-10%, 10-50%, or 50-100%. Values are expressed as the percent of total samples in each histological category: astrocytomas (A, low-grade astrocytoma; AA, anaplastic astrocytoma; GBM, glioblastoma) and normal brain. FIGS. 10B-10D, IL-13Rα2, EphA2, and Fra-1 expression with respect to staining intensity. Tissue sections stained for IL-13Rα2, EphA2, or Fra-1 were analyzed based on the overall specific staining intensity of the marker in each section and assigned a score: 0, none; 1, low; 2, moderate; 3, strong. FIG. 10B, Expression of IL-13Rα2, EphA2, and Fra-1 depicted as staining intensity vs. the percent of samples in each histological sub-type (normal brain, A, AA, or GBM). FIG. 10C, Expression of IL-13Rα2, EphA2, or Fra-1 depicted as a function of histological sub-type vs. staining intensity. * $p<0.05$;  $p<0.01$, * $p<0.001$ vs. GBM. FIG. 10D, Expression of IL-13Rα2, EphA2, or Fra-1 as a histogram representing the staining intensity of each patient sample with respect to histological sub-type.

FIG. 11A, Photomicrographs of IL-13Rα2, EphA2, and Fra-1 immunostaining in 3 different representative sections of normal brain, low-grade astrocytomas, anaplastic astrocytomas, and GBM. FIG. 11B, Photomicrographs of IL-13Rα2, EphA2, and Fra-1 immunostaining in a representative sub-set of 4 of the 16 GBM patient specimens described in Table 3. FIG. 11C, Western blot for IL-13Rα2, EphA2, and Fra-1 in human GBM tumor tissue lysates (arbitrarily numbered 1-9). β-actin served as a control for equal loading of proteins. FIG. 11D, Western blot for IL-13Rα2, EphA2, and Fra-1 in human GBM xenograft tumors and cell lines and EGFR amplification status in the tumors. The numbers of xenograft cell lines correspond to the tumors from which they originated.

FIG. 12A, Cell viability of human GBM primary explant cells (BTCOE 4536) and established human GBM cells (U-251 MG) in response to IL13.E13K-PE38QQR or ephrinA1-PE38QQR. FIG. 12B, Western blot of IL-13Rα2 and EphA2 immunoreactivity in BTCOE 4536 and U-251 MG cells. FIG. 12C, Immunofluorescent staining for GFAP in BTCOE 4536 cells.

DETAILED DESCRIPTION

Figure 1A:
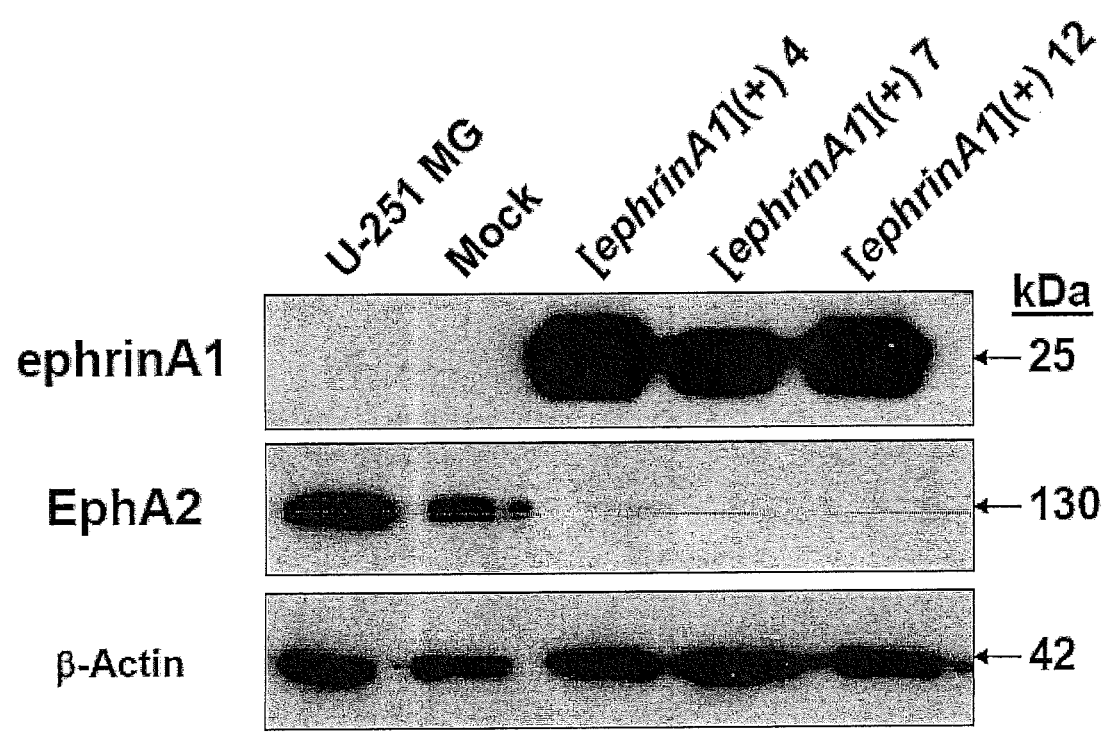
FIGS. 1A-1C. EphrinA1 and EphA2 expression in GBM and breast cancer cells in the presence or absence of cell-cell contact.

The present invention is explained in greater detail below. This description is not intended to be a detailed catalog of all the different ways in which the invention may be implemented, or all of the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure which do not depart from the instant invention. Hence, the following specification is intended to illustrate some particular embodiments of the invention, and not to exhaustively specify all permutations, combinations and variations thereof.

As used in the description of the invention and the appended claims, the singular forms "a", "an" and "the" are intended to include the plural forms as well, unless the context clearly indicates otherwise. Furthermore, the term "about," as used herein when referring to a measurable value such as an amount of a compound, dose, time, temperature, and the like, is meant to encompass variations of 20%, 10%, 5%, 1%, 0.5%, or even 0.1% of the specified amount. Also, as used herein, "and/or" refers to and encompasses any and all possible combinations of one or more of the associated listed items, as well as the lack of combinations when interpreted in the alternative ("or").

The disclosures of all United States patent references cited herein are hereby incorporated by reference herein in their entirety.

It has been previously demonstrated that the EphA2 receptor tyrosine kinase is an attractive molecular target in glioblastoma multiforme (GBM), the most common and lethal primary malignant brain tumor. The expression of this receptor has been directly linked to poor cancer patient survival in GBM, as well as in breast and prostate carcinomas. See, e.g., U.S. Patent Application Publication 2006/0121539 (Debinski et al.), which is incorporated by reference herein.

It has now been uncovered that ephrinA1, a ligand for the EphA2 receptor, can be released into the extracellular environment as a monomeric protein by both ephrinA1-transfected cancer cells and cancer cells that endogenously express the ligand. This monomer of ephrinA1 retains its functional activity toward EphA2 in conditioned media and after purification from the media of ephrinA1-expressing cells. In addition, a recombinant Fc-fusion ephrinA1 reduced to its monomeric form exhibits tumor-suppressing properties by activating the EphA2 oncoprotein, which leads to anti-oncogenic signaling and down-regulation of the receptor. Released as a monomer, ephrinA1 elicits profound changes in cancer cell morphology, suppresses the oncogenic Ras-MAPK signaling pathway, and impairs migration and anchorage-independent growth. These data indicate that monomeric ephrinA1 is a tumor-suppressing protein in GBM and in other cancers, such as of the breast. Further, a monomer of ephrinA1 effectively augments neuronal growth cone collapse, suggesting that this monomeric form of the ligand is utilized in modulating developmental processes as well.

EphrinA1 can decrease the tumorigenic potential of GBM and other cancer cells through the activation and subsequent down-regulation of the EphA2 oncoprotein, which has been previously observed using a recombinant, dimeric form of ephrinA1-Fc and/or cells expressing ephrinA1 in co-culture with those expressing EphA2 (Wykosky et al. (2005) Mol. Cancer Res. 3:541-551; Walker-Daniels et al. (2002) Mol. Cancer Res. 1:79-87; Carles-Kinch et al. (2002) Cancer Res. 62:2840-2847; Duxbury et al. (2004) Oncogene 23:1448-1456). The function of ephrinA1 has been studied in this manner because this protein, like other members of the ephrin family, is considered a membrane-anchored ligand requiring cell-cell contact or oligomerization/clustering, if soluble, in order to mimic its membrane-bound nature and fulfill the structural requirements for activation of the cognate Eph receptor.

The Eph receptors comprise the largest family of tyrosine kinase receptors, a group of transmembrane proteins that are crucial in mediating important signal transduction pathways in cells such as those controlling growth, migration, and differentiation. The fourteen members of the Eph receptors are divided into A and B classes based on the similarity of their extracellular domains and their ability to interact with their membrane-bound ligands, the ephrins.

The notion that Ephs and ephrins may not, in fact, require the formation of oligomeric complexes in physiology has recent precedence in the study of this family of proteins in the context of normal nervous system development. Another member of the ephrinA family, ephrinA5, can engage in a functional interaction with the EphB2 receptor in a 1:1 heterodimeric complex, both in crystal structures and in solution, even at exceedingly high concentrations (Himanen et al. (2004) Nat. Neurosci. 7:501-509). This 1:1 ephrinA/EphB interaction is in contrast to the heterotetrameric and higher-order oligomeric complexes thought to be necessary for full Eph receptor activation and function (Davis et al. (1994) Science 266:816-819; Himanen et al. (2001) Nature 414:933-938; Toth et al. (2001) Dev. Cell 1:83-92; Bartley et al. (1994) Nature 368:558-560). In addition, it represents one of the few known instances of cross-talk between A and B class Ephs and ephrins, which was in fact cited as a possible explanation for the existence of the unexpected, functional 1:1 receptor/ligand complex (Himanen et al. (2004) Nat. Neurosci. 7:501-509).

It has now been demonstrated for the first time that monomeric ephrins play a role as soluble factors in activating Ephs of their own class during cancer maintenance and/or progression and normal developmental/physiological processes. This has simplifying implications on the design of therapies against solid tumors exploiting the ephrinA1/EphA2 system.

In support of this finding, 12-amino acid ephrinA1-mimetic peptides have the capacity to bind and activate EphA2 (Koolpe et al. (2002) J. Biol. Chem. 277:46974-46979; U.S. Patent Publication No. 2004/0180823). The peptides compete with other ephrinA ligands for binding to the receptor, which may indicate that they utilize the ephrinA binding sites of EphA2. The amino acid sequences of these peptides do not show homology to ephrinA1.

The experiments with a homodimer of ephrinA1-Fc reduced to a monomeric form, as well as the monomer of His-ephrinA1 isolated from conditioned media, directly reveal the functional activity of this ligand as a non covalently-linked single-chain protein. This, together with the finding that soluble, monomeric ephrinA1 is present in the media of GBM and breast cancer cells and exhibits functional properties similar to dimeric ephrinA1-Fc, suggests that the ligand is capable of interacting with EphA2 in a manner that is not dependent on juxtacrine interactions.

Results demonstrating that ephrinA1, as a non covalently-linked monomer, is functional in eliciting collapse of neuronal growth cones support a role for the monomer in physiology. The role of dimeric or clustered ephrinA ligands in affecting this process has been established previously (Marquardt et al. (2005) Cell 121:127-139; Meima et al. (1997) Eur. J. Neurosci. 9:177-188). With respect to development, it is well-known that a major function of Eph/ephrin interaction is the formation of boundaries between populations of cells, such as with respect to the developing retinotectal system (Nakamoto et al. (1996) Cell 86:755-766; Rashid et al. (2005) Neuron 47:57-69; Xu et al. (1997) J. Mol. Med. 75:576-586). While processes such as these may be in part dependent on cell-cell contact, a paracrine role for ephrinA1, both in physiology and in cancer is evident.

The role of ephrinA1 as a tumor-suppressing protein in GBM was first suspected based on findings that the ligand was largely absent in the majority of GBM cases, in sharp contrast to abundantly overexpressed EphA2 (Wykosky et al. (2005) Mol. Cancer Res. 3:541-551). This expression pattern, coupled with the ability of recombinant homodimeric ephrinA1-Fc to decrease invasion and anchorage-independent growth, pointed to the ligand as a potentially not-sufficiently-increased-during-oncogenesis tumor-suppressing protein in GBM. A similar pattern of differential EphA2/ephrinA1 expression has been shown in breast cancer (Macrae et al. (2005) Cancer Cell 8:111-118), and ephrinA1 can possess these same tumor-suppressing properties in several other solid tumors (Walker-Daniels et al. (2002) Mol. Cancer Res. 1:79-87; Carles-Kinch et al. (2002) Cancer Res. 62:2840-2847; Duxbury et al. (2004) Oncogene 23:1448-1456). Presumably, under normal circumstances, ephrinA1 activates EphA2 in pre-malignant and malignant cells, maintaining the expression of the receptor at a low level and, by this, suppressing oncogenic signaling pathways. In support of this, ephrinA1-mediated activation of EphA2 has been shown to suppress the activity of ERK in breast and prostate cancer (Miao et al. (2001) Nat. Cell Biol. 3:527-530) as well as a two-stage model of skin carcinogenesis (Guo et al. (2006) Cancer Res. 66:7050-7058). A similar phenomenon in GBM cells has now been found.

Therefore, EphA2 could play a dual role in cancer: anti-oncogenic when activated by tumor-suppressing ephrinA1 and maintained at low levels, and oncogenic when ephrinA1 is not present and thus contributing to its own overexpression that is driven by other mechanisms. In fact, the oncogenicity of un-activated, non-tyrosine-phosphorylated EphA2 has been shown directly in its ability to transform mammary epithelial cells (Zelinski et al. (2001) Cancer Res. 61:2301-2306), which may be attributed to its ligand-independent kinase activity (Zantek et al. (1999) Cell Growth Differ. 10:629-638). Additional support for ephrins as potential tumor-suppressing proteins acting through Eph receptors is contained in a recent study that shows the EphB4 receptor as a tumor suppressor in breast cancer via stimulation with ephrinB2, a ligand which is absent in the majority of breast cancer cells (Noren et al. (2006) Nat. Cell Biol. 8:815-825). Interestingly, ephrinA1 has also been shown to play a role in angiogenesis and neovascularization through its effect on endothelial cells expressing EphA receptors (Daniel et al. (1996) Kidney Int. Suppl. 57:S73-S81; Cheng et al. (2002) Mol. Cancer Res. 1:2-11). However, these observations point toward a possible pleiotropic effect of ephrinA1 with respect to cell-type and specific environment.

The form of ephrinA1 required or able to exert tumor-suppressing functions through EphA2 has not been previously established. Covalently-linked dimers or clustered forms of the ligand have been shown to activate the receptor, which results in decreased tumorigenic potential, both in vitro and in vivo (Noblitt et al. (2004) Cancer Gene Ther. 11:757-766). Soluble, monomeric ephrinA1 has now been shown to exhibit a full spectrum of biological activities. Furthermore, ephrinA1 is not dependent on juxtacrine interactions and can, indeed, function in a paracrine manner. These findings will aid in deciphering the role of ephrinA1 and EphA2 in solid tumor progression. In addition, they will facilitate the design and allow for a wider application of ephrinA1-based therapeutics targeting the EphA2 receptor involving, inter alia, the use of simplified soluble recombinant proteins and viral gene therapy.

EphA2 is internalized when bound by its natural ligand, ephrin-A1 (Walker-Daniels et al. (2002) Mol Cancer Res 1:79-87) and thus represents an attractive target for therapies utilizing bacterial toxin-containing cytotoxins (Debinski W. (2002) Molecular "Targeting of Brain Tumors with Cytotoxin," In: Chimeric Toxins (Lorberboum-Galski & Lazarovici, eds., Harwood Academic Publishers) pp. 222-246; Debinski (2002) Cancer Invest. 20:801-809). Moreover, EphA2 can serve as a target for active immunotherapy in the form of anti-cancer vaccines (Hatano et al. (2005) Neoplasia 7:717-22; A1 ves et al. (2003) Cancer Res 63:8476-8480). Coincidentally, the same applies to IL-13Rα2, which has become a target of interest in the design of anti-cancer vaccines (Okano et al. (2002) Clin Cancer Res 8:2851-2855). Thus, EphA2 is a novel target for prospective molecularly targeted therapies of GBM.

What makes the EphA2/ephrin A1 system different from the IL-13 system in HGG is that the ephrinA1 ligand has a profound anti-tumor effect on cancer cells, and its peptidomimetics are being searched (Koolpe et al. (2002) J. Biol. Chem. 277:46974-46979; U.S. Patent Publication No. 2004/0180823). Also, EphA2 is expressed in an additional compartment of HGG, the neo-vascular bed, which should provide a greater benefit when using anti-EphA2 targeted drugs. In addition, the recombinant drug candidates may be of use in many other solid tumors. Being that the heterogeneity of HGG is one of the factors hampering the outcome of treatments, a possibility of having at least two specific molecular targets for therapeutic delivery of differing intratumoral distribution in this disease may be an advantage.

Recombinant cytotoxins consisting of a ligand targeted to a tumor-specific molecule and a bacterial toxin derivative are emerging as a way to improve the outcome of patients with GBM and other cancers. IL-13-based, bacterial toxin-containing recombinant cytotoxic fusion proteins have been previously generated and shown to be very potent anti-glioma cytotoxins in vitro and in vivo (Debinski et al. (1999) Clin. Cancer Res. 5:985-990; Debinski et al. (1995) Clin. Cancer Res. 1:1253-1258; Debinski et al. (1998) Nature Biotech. 16:449-453). The first generation of IL-13-based cytotoxin, hIL13-PE38QQR, contains wild-type IL-13 and a derivative of the bacterial toxin *Pseudomonas* exotoxin A (PE). This cytotoxin was in Phase III clinical trials in patients with recurrent GBM and showed highly significantly better progression-free survival when compared to standard of care.

Recombinant cytotoxins are: (a) water soluble and relatively small (50 to 200 kDa) compounds, (b) deliverable using an interstitial/intratumoral drug administration system termed convection enhanced delivery (CED) (Debinski (2002) Cancer Invest. 20:801-809; Laske et al. (1997) Nature Med. 3:1362-1368), (c) very potent at killing cells: their $IC_{50}$s can be in the femtomolar range (Debinski et al. (1999) Clin. Cancer Res. 5:985-990), (d) virtually independent of anti-apoptotic cell predisposition (Keppler-Hafkemeyer et al. (1998) Biochemistry 37:16934-16942; Keppler-Hafkemeyer et al. (2000) Int. J. Cancer 87:86-94), (e) not readily resistant, and (f) cytotoxic in proportion to the number of internalized binding sites on cancer cells, and thus independent of any other role plasma membrane targets for cytotoxins may play in cancer pathogenesis (Pastan et al. (1992) Ann. Rev. Biochem. 61:331-354). Recombinant cytotoxins represent a new qualitative group of anti-cancer therapeutics (Carglia et al. (2000) Eur. J. Biochem. 267: 3919-3936).

1. Definations.

As used herein, "ephrin" or "ephrins" are those proteins, peptides, variants, and/or fragments thereof, belonging to the ephrin family of proteins, e.g., ephrinA1, ephrinA2, ephrinA3, ephrinA4, ephrinA5, ephrinB1, ephrinB2, and ephrinB3. In some embodiments, ephrins are ephrinA1 proteins or peptides. In some embodiments, ephrin molecules are mammalian (e.g., human or mouse) ephrinA1 proteins or peptides.

As used herein, the terms "Eph" or "Eph receptor" refer to a class of transmembrane receptor tyrosine kinases, thought to include at least eleven paralogous genes, though many more orthologs exist within this class, e.g. homologs from different species. Eph receptors, in general, are a discrete group of receptors related by homology. They are characterized by an extracellular domain containing a characteristic spacing of cysteine residues near the N-terminus, and two fibronectin type III repeats. Exemplary Eph receptors include EphA1, EphA2, EphA3, EphA4, EphA5, EphA6, EphA7, EphA8, EphB1, EphB2, EphB3, EphB4 and EphB5, eph, elk, eck, sek, mek4, hek, hek2, eek, erk, tyro1, tyro4, tyro5, tyro6, tyro11, cek4, cek5, cek6, cek7, cek8, cek9, cek10, bsk, rtk1, rtk2, rtk3, myk1, myk2, ehk1, ehk2, pagliaccio, htk, erk and nuk receptors. Furthermore, "mek4/sek receptors" refers to a closely related subgroup of the Eph receptor family, including the "mek4-related receptors" such as mek4, cek4, hek and tyro4; the "sek-related receptors" such as sek, cek8, pagliaccio, tyro1 and rtk1; and other phylogenetically related homologs such as eek, bsk, ehk1, ehk2, and cek7. In some embodiments, Eph receptors are the EphA2 receptors.

Ligands of the Eph receptors include, but are not limited to, the ephrins, such as those listed above. In some embodiments, ligands of the EphA2 receptors are ephrinA1 proteins or polypeptides. Further discussion of ephrins and Eph receptors is found in U.S. Patent Application Publication No. 2006/0121539 (Debinski et al.), which is incorporated by reference herein in its entirety.

One of skill in the art will appreciate that analogues or fragments of ephrins will also specifically bind to the Eph receptors. Thus, the term "ephrin," when used in reference to a targeting molecule, also includes fragments, analogues or peptide mimetics of ephrins that also specifically bind to the Eph receptors (See, e.g., Pat. Publication Nos. 2006/0177452 and 2004/0180823 to Pasquale et al.).

"IL13" or "IL-13" as used herein refers to interleukin-13, which is a pleiotropic cytokine. IL-13 has approximately 30% sequence identity with IL4 and exhibits IL4-like activities on monocytes/macrophages and human B cells (Minty et al. (1993) Nature 362:248; McKenzie et al. (1987) Proc. Natl. Acad. Sci. USA 90:3735). In particular, IL-13 appears to be a potent regulator of inflammatory and immune responses. IL-13 can up-regulate the monocyte/macrophage expression of CD23 and MHC class I and class II antigens, down-regulate the expression of Fc.gamma, and inhibit antibody-dependent cytotoxicity. IL-13 can also inhibit nitric oxide production as well as the expression of pro-inflammatory cytokines (e.g., IL-1, IL-6, IL-8, IL-10 and IL-12) and chemokines (MIP-1, MCP), but enhance the production of IL-1.

Recombinant IL-13 is commercially available from a number of sources (e.g., R&D Systems, Minneapolis, Minn., and Sanofi Bio-Industries, Inc., Tervose, Pa.). A1 ternatively, a gene or cDNA encoding IL-13 may be cloned into a plasmid or other expression vector and expressed in any of a number of expression systems according to methods well known to those of skill in the art. Methods of cloning and expressing IL-13 and the nucleic acid sequence for IL-13 are well known (see, for example, Minty et al. (1993) supra and McKenzie (1987) supra). In addition, the expression of IL-13 as a component of a chimeric molecule is detailed below. A1 so contemplated is the use of specific IL-13 mutants as described in U.S. Pat. No. 6,884,603 (Debinski et al.).

One of skill in the art will appreciate that analogues or fragments of IL-13 will also specifically bind to the IL-13 receptor. For example, conservative substitutions of residues (e.g., a serine for an alanine or an aspartic acid for a glutamic acid) comprising native IL-13 will provide IL-13 analogues that also specifically bind to the IL-13 receptor. Thus, the term "IL-13," when used in reference to a targeting molecule, also includes fragments, analogues or peptide mimetics of IL-13 that also specifically bind to the IL-13 receptor.

Further discussion of IL-13 as contemplated by the present invention can be found in U.S. Pat. No. 5,328,984 (Pastan et al.), U.S. Pat. No. 5,614,191 (Puri et al.), U.S. Pat. No. 5,919,456 (Puri et al.), U.S. Pat. No. 6,296,843 (Debinski), U.S. Pat. No. 6,428,788 (Debinski et al.), U.S. Pat. No. 6,518,061 (Puri et al.), U.S. Pat. No. 6,576,232 (Debinski et al.), U.S. Pat. No. 6,630,576 (Debinski), and U.S. Pat. No. 6,884,603 (Debinski et al.).

"Recombinant" nucleic acid as used herein refers to a nucleic acid produced by combining two or more nucleic acid sequences from different sources, e.g., by use of molecular biology techniques, to form a new nucleic acid, e.g., a "heterologous" nucleic acid. The recombinant nucleic acid may be provided in the form of a "vector" or "delivery vector" in order to transform or transfect cells to contain the new nucleic acid. As used herein, a "vector" or "delivery vector" can be a viral or non-viral vector that is used to deliver a nucleic acid to a cell, tissue or subject.

A "recombinant" protein is a protein produced by a recombinant nucleic acid. The nucleic acid may or may not be inserted into the genome of a host cell. The nucleic acid may exist, e.g., in plasmid form in a host cell. Alternatively, the recombinant protein may be produced by in vitro translation of the recombinant nucleic acid.

As used herein, an "active" protein or peptide is one that retains at least one biological activity normally associated with that protein. Preferably, an "active" protein retains all of the activities possessed by the unmodified protein. By "retains" biological activity, it is meant that the polypeptide retains at least about 50%, 60%, 75%, 85%, 90%, 95%, 97%, 98%, 99%, or more, of the biological activity of the native protein (and can even have a higher level of activity than the native protein). A "non-active" protein or polypeptide is one that exhibits essentially no detectable biological activity normally associated with the polypeptide (e.g., at most, only an insignificant amount, e.g., less than about 10% or even 5%).

An "active fragment" of an ephrin protein of this invention is an amino acid sequence having fewer than all of the amino acids of the full or complete amino acid sequence of an ephrin, and that retains one or more of the activities associated with the ephrinA1 protein. For example, activities of the ephrinA1 protein include, but are not limited to, interacting with, binding to, and activating the EphA2 receptor.

A "biologically active fragment" or "active fragment" as used herein includes a polypeptide that comprises a sufficient number of amino acids to have one or more of the biological activities of the proteins or polypeptides of this invention. A fragment of a polypeptide of this invention can be produced by methods well known and routine in the art. Fragments of this invention can be produced, for example, by enzymatic or other cleavage of naturally-occurring proteins or polypeptides or by synthetic protocols that are well known. Such fragments can be tested for one or more of the biological activities of this invention according to the methods described herein, and/or according to any art-known and routine methods for identifying such activities. Such production and testing to identify biologically active fragments of the polypeptides described herein would be well within the scope of one of ordinary skill in the art and would be routine.

Fragments of the polypeptides of this invention may be at least about ten amino acids in length and retain one or more of the biological activities of the ephrin proteins. For example, non-homologous amino acid fragments that are 12 amino acids in length are active in EphA2 binding (Koolpe et al. (2002) J. Biol. Chem. 277:46974-46979).

An "isolated" protein or polypeptide means a protein or polypeptide that is separated or substantially free from at least some of the other components of the naturally occurring organism or virus, for example, the cell or viral structural components or other proteins or nucleic acids commonly found associated with the protein. As used herein, the "isolated" protein or polypeptide is at least about 25%, 30%, 40%, 50%, 60%, 70%, 75%, 80%, 85%, 90%, 95%, 97%, 98%, 99% or more pure (w/w).

As used herein an "isolated" cell is a cell that is free or substantially free from at least some of the other components of the naturally occurring organism. An "isolated" cell can be a cultured cell. Alternatively, an "isolated" cell can be a cell in a pharmaceutical composition. Further, an "isolated" cell can be a cell that has been implanted into a recipient host. According to this embodiment, the cell can be derived from the host subject or can be foreign to the subject.

By the term "express," "expresses" or "expression" of a nucleic acid coding sequence, in particular an ephrinA1 coding sequence, it is meant that the sequence is translated into a protein or polypeptide of ephrinA1. Prokaryotic and eukaryotic expression systems may each be employed according to standard techniques. The most common prokaryotic organism used for protein expression is E. coli. Eukaryotic expression may be desirable when post-translational processing and protein folding that are specific to eukaryotic cells is desired, e.g., glycosylation. Three common eukaryotic expression systems are yeast cells, insect cells, and mammalian cells.

To modify the ephrinA1 amino acid sequences disclosed herein or otherwise known in the art, amino acid substitutions can be based on any characteristic known in the art, including the relative similarity or differences of the amino acid side-chain substituents, for example, their hydrophobicity, hydrophilicity, charge, size, and the like. In particular embodiments, conservative substitutions (i.e., substitution with an amino acid residue having similar properties) are made in the amino acid sequence encoding ephrinA1.

In making amino acid substitutions, the hydropathic index of amino acids can be considered. The importance of the hydropathic amino acid index in conferring interactive biologic function on a protein is generally understood in the art (Kyte and Doolittle (1982) J. Mol. Biol. 157:105, incorporated herein by reference in its entirety). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of its hydrophobicity and charge characteristics (Kyte and Doolittle (1982) J. Mol. Biol. 157:105), and these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is also understood in the art that the substitution of amino acids can be made on the basis of hydrophilicity. U.S. Pat. No. 4,554,101 (incorporated herein by reference in its entirety) teaches that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (±3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

Expression vectors can be designed for expression of proteins or polypeptides in prokaryotic or eukaryotic cells. For example, polypeptides can be expressed in bacterial cells such as E. coli, insect cells (e.g., in the baculovirus expression system), yeast cells or mammalian cells. Suitable host cells are discussed further in Goeddel, Gene Expression Technology: Methods in Enzymology 185, Academic Press, San Diego, Calif. (1990). Examples of vectors for expression in yeast S. cerevisiae include pYepSec1 (Baldari et al. (1987) EMBO J. 6:229-234), pMFa (Kurjan and Herskowitz (1982) Cell 30:933-943), pJRY88 (Schultz et al. (1987) Gene 54:113-123), and pYES2 (Invitrogen Corporation, San Diego, Calif.). Baculovirus vectors available for expression of nucleic acids to produce proteins in cultured insect cells (e.g., Sf 9 cells) include the pAc series (Smith et al. (1983) Mol. Cell. Biol. 3:2156-2165) and the pVL series (Lucklow & Summers (1989) Virology 170:31-39).

Vectors can be introduced into prokaryotic or eukaryotic cells via conventional transformation or transfection techniques. As used herein, the terms "transformation" and "transfection" refer to a variety of art-recognized techniques for introducing foreign nucleic acids (e.g., DNA) into a host cell, including calcium phosphate or calcium chloride co-precipitation, DEAE-dextran-mediated transfection, lipofection, electroporation, microinjection, DNA-loaded liposomes, lipofectamine-DNA complexes, cell sonication, gene bombardment using high velocity microprojectiles, and viral-mediated transfection. Suitable methods for transforming or transfecting host cells can be found in Sambrook et al. (Molecular Cloning: A Laboratory Manual, 2nd Edition, Cold Spring Harbor Laboratory press (1989)), and other laboratory manuals.

"Subjects" as used herein are generally human subjects and includes, but is not limited to, cancer patients. The subjects may be male or female and may be of any race or ethnicity, including, but not limited to, Caucasian, African-American, African, Asian, Hispanic, Indian, etc. The subjects may be of any age, including newborn, neonate, infant, child, adolescent, adult, and geriatric. Subjects may also include animal subjects, particularly mammalian subjects such as canines, felines, bovines, caprines, equines, ovines, porcines, rodents (e.g. rats and mice), lagomorphs, primates (including non-human primates), etc., screened for veterinary medicine or pharmaceutical drug development purposes.

Cancers that can be detected and/or treated by the compounds, compositions and methods described herein include those malignancies deprived of ephrinA1 and having increased levels of EphA2, its receptor, which is an oncogenic receptor. Examples of such cancers include, but are not limited to, breast cancer, bladder cancer, pancreatic cancer, colorectal cancer, head and neck cancer, thyroid cancer, prostate cancer, and brain cancer such as gliomas (e.g., GBM), etc.

"Therapeutic agent" as used herein may be any therapeutic agent including, but not limited to, genetic materials or agents, radionuclides, chemotherapeutic agents, and cytotoxic agents. See, e.g., U.S. Pat. No. 6,949,245 to Sliwkowski.

"Radionuclide" as described herein includes, but is not limited to, $^{227}$Ac, $^{211}$At, $^{131}$Ba, $^{77}$Br, $^{109}$Cd, $^{51}$Cr, $^{67}$Cu, $^{165}$Dy, $^{155}$Eu, $^{153}$Gd, $^{198}$Au, $^{166}$Ho, $^{113m}$In, $^{115m}$In, $^{123}$I, $^{125}$I, $^{131}$I, $^{189}$Ir, $^{191}$Ir, $^{192}$Ir, $^{194}$Ir, $^{52}$Fe, $^{55}$Fe, $^{59}$Fe, $^{177}$Lu, $^{109}$Pd, $^{32}$P, $^{226}$Ra, $^{186}$Re, $^{188}$Re, $^{153}$Sm, $^{46}$Sc, $^{47}$Sc, $^{72}$Se, $^{75}$Se, $^{105}$Ag, $^{89}$Sr, $^{35}$S, $^{177}$Ta, $^{117m}$Sn, $^{121}$Sn, $^{166}$Yb, $^{169}$Yb, $^{90}$Y, $^{212}$Bi, $^{119}$Sb, $^{197}$Hg, $^{97}$Ru, $^{100}$Pd, $^{101m}$Rh, and $^{212}$Pb.

"Chemotherapeutic agent" as used herein includes, but is not limited to, methotrexate, daunomycin, mitomycin C, cisplatin, vincristine, epirubicin, fluorouracil, verapamil, cyclophosphamide, cytosine arabinoside, aminopterin, bleomycin, mitomycin C, democolcine, etoposide, mithramycin, chlorambucil, melphalan, daunorubicin, doxorubicin, tamosifen, paclitaxel, vincristin, vinblastine, camptothecin, actinomycin D, and cytarabine. Other examples are found in U.S. Patent Application Publication 2006/0121539 (Debinski et al.), which is incorporated by reference herein in its entirety.

"Cytotoxic agent" or "toxic agent" as used herein includes, but is not limited to, maytansinoids and maytansinoid analogs, taxoids, CC-1065 and CC-1065 analogs, dolastatin and dolastatin analogs, ricin (or more particularly the ricin A chain), aclacinomycin, Diphtheria toxin, Monensin, Verrucarin A, Abrin, Tricothecenes, and Pseudomonas exotoxin A, taxol, cytochalasin B, gramicidin D, ethidium bromide, emetine, mitomycin, etoposide, tenoposide, antimitotic agents, such as the vinca alkaloids (e.g., vincristine and vinblastine), colchicin, anthracyclines, such as doxorubicin and daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof, antimetabolites (e.g., methotrexate, 6-mercaptopurine, 6-thioguanine, cytarabine, and 5-fluorouracil decarbazine), alkylating agents (e.g., mechlorethamine, thioepa chlorambucil, melphalan, carmustine (BSNU), lomustine (CCNU), cyclothosphamide, busulfan, dibromomannitol, streptozotocin, mitomycin C, and cis-dichlorodiamine platinum (II) (DDP)), and antibiotics, including, but not limited to, dactinomycin (formerly actinomycin), bleomycin, mithramycin, calicheamicin, and anthramycin (AMC)).

In some embodiments, cytotoxic agents include a Pseudomonas exotoxin or a Diphtheria toxin. See U.S. Pat. No. 5,328,984 to Pastan et al. and U.S. Pat. No. 6,296,843 to Debinski, which are each incorporated by reference herein in its entirety. Pseudomonas exotoxins can include, but are not limited to, Pseudomonas exotoxin A (PE). The Pseudomonas exotoxin can be modified such that it substantially lacks domain Ia, and in some embodiments Pseudomonas exotoxins include PE38QQR and PE4E. Diphtheria toxins can include DT390, a diphtheria toxin in which the native binding domain is eliminated. It will be appreciated that in various embodiments, the therapeutic agents can be attached to, e.g., the amino terminus or the carboxyl terminus.

"Detectable group" as used herein includes, but is not limited to, radiolabels (e.g., $^{35}$S, $^{125}$I, $^{32}$P, $^{3}$H, $^{14}$C, $^{131}$I), enzyme labels (e.g., horseradish peroxidase, alkaline phosphatase), gold beads, chemiluminescence labels, ligands (e.g., biotin, digoxin) and/or fluorescence labels (e.g., rhodamine, phycoerythrin, fluorescein, fluorescent proteins), a fluorescent protein including, but not limited to, a green fluorescent protein or one of its many modified forms, a nucleic acid segment in accordance with known techniques, and energy absorbing and energy emitting agents.

The terms "treat," "treating" or "treatment" as used herein refers to any type of treatment that imparts a benefit to a patient afflicted with a disease, including improvement in the condition of the patient (e.g., in one or more symptoms), delay in the progression of the disease, etc.

The term "pharmaceutically acceptable" as used herein means that the compound or composition is suitable for administration to a subject to achieve the treatments described herein, without unduly deleterious side effects in light of the severity of the disease and necessity of the treatment.

"Concurrently administering" or "concurrently administer" as used herein means that the two or more compounds or compositions are administered closely enough in time to produce a combined effect (that is, concurrently may be simultaneously, or it may be two or more events occurring within a short time period before or after each other, e.g., sequentially). Simultaneous concurrent administration may be carried out by mixing the compounds prior to administration, or by administering the compounds at the same point in time but at different anatomic sites and/or by using different routes of administration.

The definitions and techniques described herein also apply to the IL-13 proteins, toxin proteins, and other compounds and compositions mentioned hereinabove and hereinbelow.

2. Ephrin Compounds.

In some embodiments, active compounds of the present invention include ephrin molecules, e.g., ephrinA1, ephrinA2, ephrinA3, ephrinA4, ephrinA5, ephrinB1, ephrinB2, ephrinB3 proteins, peptides, variants, and fragments thereof. In particular embodiments, ephrin molecules are ephrinA1 proteins. In some embodiments, ephrin molecules are mammalian (e.g., human or mouse) ephrinA1 proteins. Further discussion of ephrin molecules, and their receptors, e.g., EphA2, is found in U.S. Patent Application Publication No. 2006/0121539 (Debinski et al.), which is incorporated by reference herein in its entirety. In some embodiments, recombinant ephrinA1 includes a histidine tag for ease of purification.

EphrinA1 in dimeric form is known and may be from any (preferably mammalian) species, including, but not limited to, mouse, human, rat, dog, cat, monkey, etc. In some embodiments, the dimeric ephrinA1 includes the extracellular domain of ephrinA1 fused to the carboxy-terminal 6× histidine-tagged Fc region of human IgG via a polypeptide linker, as commercially available (e.g., Mouse Ephrin-A1/Fc Chimera, R&D Systems, Inc.).

In some embodiments of the invention, the ephrinA1 is provided in monomeric form. Active ephrinA1 in monomeric form is preferred over the currently-used covalently-linked dimeric form for its ease of use and design of ephrinA1-based therapies.

In one non-limiting embodiment of the invention, the amino acid/peptide sequence may be that of human ephrinA1 isoform a of SEQ ID NO:1 (NCBI Accession No. AAH32698):

MEFLWAPLLGLCCSLAAADRHTVFWNSSNPKFRNEDYTIHVQL

NDYVDIICPHYEDHSVADAAMEQYILYLVEHEEYQLCQPQSKD

QVRWQCNRPSAKHGPEKLSEKFQRFTPFTLGKEFKEGHSYYYI

-continued
SKPIHQHEDRCLRLKVTVSGKITHSPQAHVNPQEKRLAADDPE

VRVLHSIAHSAAPRLFPLAWTVLLLPLLLLQTP or fragments or analogs thereof, encoded by the cDNA sequence of SEQ ID NO:2 (NCBI Accession No. BCO32698). In non-limiting embodiments, a fragment of the peptide sequence starts at the aspartic acid residue at amino acid 19 (in bold). In further non-limiting embodiments, a fragment of the peptide sequence starts at the aspartic acid residue at amino acid 19, and ends at amino acid 182.

In another non-limiting embodiment of the invention, the amino acid/peptide sequence may be that of human ephrinA1 isoform a of SEQ ID NO:3 (NCBI Accession No. NP 004419):

MEFLWAPLLGLCCSLAAADRHTVFWNSSNPKFRNEDYTIHVQL

NDYVDIICPHYEDHSVADAAMEQYILYLVEHEEYQLCQPQSKD

QVRWQCNRPSAKHGPEKLSEKFQRFTPFTLGKEFKEGHSYYYI

SKPIHQHEDRCLRLKVTVSGKITHSPQAHDNPQEKRLAADDPE

VRVLHSIGHSAAPRLFPLAWTVLLLPLLLLQTP or fragments or analogs thereof, encoded by the genomic DNA sequence of SEQ ID NO:4 (NCBI Accession No. NM_004428). In non-limiting embodiments, a fragment of the peptide sequence starts at the aspartic acid residue at amino acid 19 (in bold). In further non-limiting embodiments, a fragment of the peptide sequence starts at the aspartic acid residue at amino acid 19, and ends at amino acid 182.

There is not 100% identity between the reported sequences of the human ephrinA1 isoform a genomic and cDNA clones. This results in a difference of 2 amino acid residues in the predicted protein sequences (underlined). The reported chimpanzee genomic sequence agrees with the human genomic sequence.

In another non-limiting embodiment of the invention, the amino acid/peptide sequence may be that of human ephrinA1 isoform b (NCBI Accession No. NP_872626) (SEQ ID NO:5):

MEFLWAPLLGLCCSLAAADRHTVFWNSSNPKFRNEDYTIHVQL

NDYVDIICPHYEDHSVADAAMEQYILYLVEHEEYQLCQPQSKD

QVRWQCNRPSAKHGPEKLSEKFQRFTPFTLGKEFKEGHSYYYI

SHSPQAHDNPQEKRLAADDPEVRVLHSIGHSAAPRLFPLAWTV

LLLPLLLLQTP or fragments or analogs thereof, encoded by SEQ ID NO:6 (NCBI Accession No. NM_182685). This isoform lacks a segment of 22 amino acids found in isoform a (residues 131-152). In non-limiting embodiments, a fragment of the peptide sequence starts at the aspartic acid residue at amino acid 19 (in bold). In further non-limiting embodiments, a fragment of the peptide sequence starts at the aspartic acid residue at amino acid 19, and ends at amino acid 160.

In a further non-limiting embodiment of the invention, the amino acid/peptide sequence may be that of murine ephrinA1 (NCBI Accession No. NP_034237) (SEQ ID NO:7):

```
MEFLWAPLLGLCCSLAAADRHIVFWNSSNPKFREEDYTVHVQL

NDYLDIICPHYEDDSVADAAMERYTLYMVEHQEYVACQPQSKD

QVRWNCNRPSAKHGPEKLSVKFQRFTPFILGKEFKEGHSYYYI

SKPIYHQESQCLKLKVTVNGKITHNPQAHVNPQEKRLQADDPE

VQVLHSIGYSAAPRLFPLVWAVLLLPLLLLQSQ
``` or fragments or analogs thereof, encoded by the DNA sequence of SEQ ID NO:8 (NCBI Accession No. NM_010107). In non-limiting embodiments, a fragment of the peptide sequence starts at the aspartic acid residue at amino acid 19 (in bold). In further non-limiting embodiments, a fragment of the peptide sequence starts with the aspartic acid at amino acid 19, and ends at amino acid 182.

Active compounds including small interfering RNA (siRNA) are also contemplated herein (Landen Jr. et al. (2005) Cancer Res. 65:6910-6918). Methods involving siRNA can be used to silence a targeted gene, e.g., an Eph receptor (such as EphA2).

3. IL-13 Compounds.

In some embodiments, active compounds of the present invention include Interleukin 13 molecules, e.g., IL-13 proteins, peptides, variants, and fragments thereof. In particular embodiments, IL-13 molecules are IL-13 proteins. In some embodiments, IL-13 molecules are mammalian (e.g., human or mouse) IL-13 proteins. Further discussion of IL-13 molecules and mutants thereof is found in U.S. Pat. No. 6,884,603 (Debinski et al.), which is incorporated by reference herein in its entirety. In some embodiments, recombinant IL-13 includes a histidine tag for ease of purification.

IL-13 is known and may be from any (preferably mammalian) species, including, but not limited to, mouse, human, rat, dog, cat, monkey, etc. In one non-limiting embodiment of the invention, the amino acid/peptide sequence may be that of human IL-13 of SEQ ID NO:9 (NCBI Accession No. NP_002179):

```
MHPLLNPLLL ALGLMALLLT TVIALTCLGG FASPGPVPPS

TALRELIEEL VNITQNQKAP LCNGSMVWSI NLTAGMYCAA

LESLINVSGC SAIEKTQRML SGFCPHKVSA GQFSSLHVRD

TKIEVAQFVK DLLLHLKKLF REGQFN
``` or fragments or analogs thereof, encoded by the cDNA sequence of SEQ ID NO:10 (NCBI Accession No. NM_002188). In non-limiting embodiments, a fragment of the peptide sequence starts at the aspartic acid residue at amino acid 35 (in bold). In further non-limiting embodiments, a fragment of the peptide sequence starts with the aspartic acid at amino acid 35, and ends at amino acid 146.

In a further non-limiting embodiment of the invention, the amino acid/peptide sequence may be that of murine IL-13 (NCBI Accession No. NP_032381) (SEQ ID NO:11):

```
MALWVTAVLA LACLGGLAAP GPVPRSVSLP LTLKELIEEL

SNITQDQTPL CNGSMVWSVD LAAGGFCVAL DSLTNISNCN

AIYRTQRILH GLCNRKAPTT VSSLPDTKIE VAHFITKLLS

YTKQLFRHGP F
``` or fragments or analogs thereof, encoded by the DNA sequence of SEQ ID NO:12 (NCBI Accession No. NM 008355).

In a still further non-limiting embodiment of the invention, the amino acid/peptide sequence may be that of rat IL-13 (NCBI Accession No. NP_446280) (SEQ ID NO:13):

```
MALWVTAVLA LACLGGLATP GPVRRSTSPP VALRELIEEL

SNITQDQKTS LCNSSMVWSV DLTAGGFCAA LESLTNISSC

NAIHRTQRIL NGLCNQKASD VASSPPDTKI EVAQFISKLL

NYSKQLFRYG H
``` or fragments or analogs thereof, encoded by the DNA sequence of SEQ ID NO:14 (NCBI Accession No. NM 053828).

Active compounds including small interfering RNA (siRNA) for targeting IL-13 or the IL-13Rα2 are also contemplated herein (Lively et al. (2007) J. A1 lergy Clin. Immunol. PMID 17936889; Kawakami et al. (2005) J. Immunother. 28(3):193-202). Methods involving siRNA can be used to silence IL-13 or IL-13Rα2 expression.

4. Fra-1 Compounds.

In some embodiments, active compounds of the present invention are fos-related antigen 1 (Fra-1) molecules, e.g., Fra-1 proteins, peptides, variants, and fragments thereof. In particular embodiments, Fra-1 molecules are Fra-1 proteins. In some embodiments, Fra-1 molecules are mammalian (e.g., human, rat or mouse) Fra-1 proteins. Further discussion of Fra-1 molecules is found in U.S. Pat. No. 6,884,581 (Debinski et al.) and U.S. Patent Application Publication No. 2002/0151457 (Debinski et al.), which is incorporated by reference herein in its entirety. In some embodiments, recombinant Fra-1 includes a histidine tag for ease of purification.

Fra-1 is known and may be from any (preferably mammalian) species, including, but not limited to, mouse, human, rat, dog, cat, monkey, etc. In one non-limiting embodiment of the invention, the amino acid/peptide sequence may be that of human Fra-1 of SEQ ID NO:15 (NCBI Accession No. CAA34679):

```
MFRDFGEPGP SSGNGGGYGG PAQPPAAAQA AQQKFHLVPS

INTMSGSQEL QWMVQPHFLG PSSYPRPLTY PQYSPPQPRP

GVIRALGPPP GVRRRPCEQI SPEEEERRRV RRERNKLAAA

KCRNRRKELT DFLQAETDKL EDEKSGLQRE IEELQKQKER

LELVLEAHRP ICKIPEGAKE GDTGSTSGTS SPPAPCRPVP

CISLSPGPVL EPEALHTPTL MTTPSLTPFT PSLVFTYPST

PEPCASAHRK SSSSSGDPSS DPLGSPTLLA L
``` or fragments or analogs thereof, encoded by the cDNA sequence of SEQ ID NO:16 (NCBI Accession No. X16707).

In a further non-limiting embodiment of the invention, the amino acid/peptide sequence may be that of rat Fra-1 (NCBI Accession No. AAA41171) (SEQ ID NO:17):

```
MYRDFGEPGP SSGAGSAYGR PAQPQQAQTQ TVQQQKFHLV

PSINAVSGSQ ELQWMVQPHF LGPSGYPRPL TYPQYSPPQP

RPGVIRALGP PPGVRRRPCE QISPEEEERR RVRRERNKLA

AAKCRNRRKE LTDFLQAETD KLEDEKSGLQ REIEELQKQK
```

```
ERLELVLEAH RPICKIPEED KKDTGGTSST SGAGSPPGPC

RPVPCISLSP GPVLEPEALH TPTLMTTPSL TPFTPSLVFT

YPSTPEPCSS AHRKSSSSSG DPSSDPLGSP TLLAL
``` or fragments or analogs thereof, encoded by the DNA sequence of SEQ ID NO:18 (NCBI Accession No. M19651).

In a further non-limiting embodiment of the invention, the amino acid/peptide sequence may be that of murine Fra-1 (NCBI Accession No. AAC52888) (SEQ ID NO:19):

```
MYRDYGEPGP SSGAGSAYGR PAQPPQAQAQ TAQQQKFHFV

PSIDSSSQEL HWMVQPHFLG PTGYPRPLAY PQYSPPQPRP

GVIRALGPPP GVRRRPCEQI SPEEEERRRV RRERNKLAAA

KCRNRRKELT DFLQAETDKL EDEKSGLQRE IEELQKQKER

LELVLEAHRL ICKIPEGDKK DPGGSGSTSG ASSPPAPGRP

VPCISLSPGP VLEPEALHTP TLMTTPSLTP FTPSLVFTYP

STPEPCSSTH RKSSSSSGDP SSDPLGSPTL LAL
``` or fragments or analogs thereof, encoded by the DNA sequence of SEQ ID NO:20 (NCBI Accession No. U34245).

Active compounds including small interfering RNA (siRNA) for targeting Fra-1 are further contemplated herein (Belguise et al. (2005) Oncogene 24:1434-1444). Methods involving siRNA can be used to silence Fra-1 expression. Also, some other drugs, such as chemotherapeutics, may in fact work through Fra-1 down-regulation.

5. Conjugates.

EphrinA1 induces EphA2 receptor internalization in addition to signaling through the receptor. This enables the utilization of ephrinA1 in the design of agents that require receptor-mediated internalization in order to be active, such as re-directed bacterial toxins (Debinski W. (2002) Molecular "Targeting of Brain Tumors with Cytotoxin," In: Chimeric Toxins (Lorberboum-Galski & Lazarovici, eds., Harwood Academic Publishers) pp. 222-246; Debinski (2002) Cancer Invest. 20:801-809). Accordingly, in some embodiments, ephrinA1 is provided in recombinant chimera constructs including cytotoxic proteins composed of ephrinA1 and modified proteinaceous bacterial toxins, which is a form of non-viral gene therapy. In this approach, it is expected that in one molecule of a drug candidate, a combined effect of receptor activation and a receptor-mediated drug delivery may work additively or even synergistically.

EphrinA1 in monomeric or covalently-linked dimeric form including, but not limited to, those described above, may be coupled to or conjugated to a therapeutic agent in accordance with any of a variety of techniques, such as those employed in the production of immunoconjugates. See, e.g., U.S. Pat. No. 6,949,245 to Sliwkowski.

In some embodiments, recombinant fusion chimera protein anti-cancer cytotoxins are composed of a carrier/ligand and an effector (catalyst). Carrier/ligands can be proteinaceous compounds, such as growth factors, cytokines, and monoclonal antibodies. Among effectors, bacterial toxins, such as Pseudomonas exotoxin A and Diphtheria toxin, or plant toxins, such as ricin may be utilized in some embodiments. The fusion protein is targeted only to cells expressing a target receptor/adaptor for a carrier/ligand. These targets internalize in response to carrier/ligand binding. Targets include, but are not limited to, protein receptors, antigens of various nature, adhesion molecules, gangliosides, etc. For example, EphA2 is over-expressed in a majority of patients with GBM and its ligand induces a receptor-mediated internalization once it binds the receptor (Walker-Daniels et al. (2002) Mol. Cancer Res. 1:79-87). The latter may be used for, e.g., recombinant bacterial toxin-containing cytotoxins to exert anti-tumor action (Debinski (2002) Molecular "Targeting of Brain Tumors with Cytotoxin," In: Chimeric Toxins (Lorberboum-Galski & Lazarovici, eds., Harwood Academic Publishers) pp. 222-246; Debinski (2002) Cancer Invest. 20:801-809; Debinski (2002) Cancer Invest. 20:801-809).

Chemotherapeutic agents useful in the generation of such active compounds include those described above. Conjugates of ephrinA1 and one or more small molecule toxins, such as a calicheamicin, a maytansine (See U.S. Pat. No. 5,208,020), a trichothene, and CC 1065 are also contemplated herein. In some embodiments, conjugates of ephrinA1 to Pseudomonas exotoxins are used (U.S. Pat. No. 5,328,984 to Pastan et al.).

In some embodiments of the invention, the ephrinA1 is conjugated to one or more maytansine molecules (e.g., about 1 to about 10 maytansine molecules per ephrinA1 molecule). Maytansine may, for example, be converted to May-SS-Me which may be reduced to May-SH3 and reacted with modified ephrinA1 (Chari et al. (1992) Cancer Res. 52:127-131) to generate an active compound.

Another conjugate of interest includes an ephrinA1 conjugated to one or more calicheamicin molecules. The calicheamicin family of antibiotics is capable of producing double-stranded DNA breaks at sub-picomolar concentrations. Structural analogues of calicheamicin that may be used include, but are not limited to, $\gamma_1^1$, $\alpha_2^1$, $\alpha_3^1$, N-acetyl-$\gamma_1^1$, PSAG and $\theta_1^1$, (Hinman et al. (1993) Cancer Res. 53:3336-3342; Lode et al. (1998) Cancer Res. 58:2925-2928). See also U.S. Pat. Nos. 5,714,586, 5,712,374, 5,264,586, and 5,773,001.

Enzymatically active toxins and fragments thereof which can be used are described above and include diphtheria A chain, nonbinding active fragments of diphtheria toxin, exotoxin A chain (from Pseudomonas aeruginosa), ricin A chain, abrin A chain (from Corrybacterium typhimuriae), modeccin A chain, alpha-sarcin, Aleurites fordii proteins, dianthin proteins, Phytolaca americana proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. See, for example, WO 93/21232 published Oct. 28, 1993.

The present invention further contemplates a conjugate formed between active compounds and an antibody or a compound with nucleolytic activity (e.g., a ribonuclease or a DNA endonuclease such as a deoxyribonuclease; DNase).

A variety of radioactive isotopes or radionuclides are available for the production of radioconjugated compounds as described above.

In some embodiments, conjugates of a monomeric ephrinA1 and therapeutic agents or detectable groups may be made using a variety of bi-functional protein coupling agents such as N-succinimidyl-3-(2-pyridyldithiol)propionate (SPDP), succinimidyl-4-(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2, 4-dinitrobenzene). For example, a ricin conjugate can be prepared as described in Vitetta et al. (1987) Science 238: 1098. Carbon-14-labeled 1-isothiocyanatobenzyl-3-methyl-diethylene triaminepentaacetic acid (MX-DTPA) is an exemplary chelating agent for conjugation of radionucleotide to the ephrinA1. See WO 94/11026. The linker may be a "cleavable linker" facilitating release of the cytotoxic drug in the cell. For example, an acid-labile linker, peptidase-sensitive linker, dimethyl linker or disulfide-containing linker (Chari et al. (1992) Cancer Res. 52:127-131) may be used.

Alternatively, a fusion protein including the ephrinA1 and therapeutic agent or detectable group may be made, e.g. by recombinant techniques or peptide synthesis.

In yet another embodiment, the ephrinA1 may be conjugated to a "receptor" (such as streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

Also contemplated herein are conjugates including ephrin mimetic peptides, as found in U.S. Patent Publication Nos. 2006/0177452 (Pasquale et al.) and 2004/0180823 (Pasquale et al.).

In some embodiments, the ephrinA1 includes amino acids 19-205 of the human ephrinA1, fused to a *Pseudomonas* exotoxin or Diptheria toxin. (U.S. Pat. No. 5,328,984 to Pastan et al. and U.S. Pat. No. 6,296,843 to Debinski). *Pseudomonas* exotoxins include, but are not limited to, *Pseudomonas* exotoxin A (PE). The *Pseudomonas* exotoxin can be modified such that it substantially lacks domain Ia, and *Pseudomonas* exotoxins may further include PE38QQR and PE4E. Diphtheria toxins include DT390, a diphtheria toxin in which the native binding domain is eliminated. It will be appreciated that the toxin can be connected to either of the amino terminus, e.g., DT390-ephrinA1, or the carboxyl terminus, e.g., ephrinA1-PE38QQR and ephrinA1-PE4E).

Another example of an embodiment of a structure of ephrinA1-based cytotoxin is as follows: (I) ephrinA1 has an extension at its C-terminal end by a hinge region of human IgG only and a His-tag, and not the whole Fc-His as it is now used by commercial suppliers (the released ligand will be in a form of a homodimer, similarly to ephrinA-Fc-His), (II) nickel column-purified ephrinA1-hinge-His will be subjected to reducing conditions and freed sulfhydryl groups in the hinge region will be used for conjugation with maleimide-derivatized PE38QQR to form a covalent bond between the proteins, and (III) the ephrinA1-hinge-His-PE38QQR conjugate will be purified to isolate a monomer of ephrinA1-hinge-His-PE38QQR conjugate. In this conjugate, only one molecule of ephrinA1-hinge-His will be conjugated to one molecule of PE38QQR, since the singular reactive sites for conjugation will be in the hinge region of an engineered ephrinA1 and at the N-terminal end of PE38QQR. The size of this conjugate is ~70 kDa. See also Debinski et al. (1992) Cancer Res. 52:5379-5385. There are many alternative embodiments if further modification is desired. This includes the use of DT rather than PE toxin, adding hinge-CH2 to ephrinA1 (to increase the yield, if needed), generating monomers of ephrinA1 released from cells, and its derivatization with thiol-providing hetero-bifunctional cross-linkers as previously employed.

IL-13-based conjugates are also contemplated herein. See, e.g., U.S. Pat. No. 5,328,984 (Pastan et al.), U.S. Pat. No. 5,614,191 (Puri et al.), U.S. Pat. No. 5,919,456 (Puri et al.), U.S. Pat. No. 6,296,843 (Debinski), U.S. Pat. No. 6,428,788 (Debinski et al.), U.S. Pat. No. 6,518,061 (Puri et al.), U.S. Pat. No. 6,576,232 (Debinski et al.), U.S. Pat. No. 6,630,576 (Debinski), and U.S. Pat. No. 6,884,603 (Debinski et al.). The first generation of IL-13-based cytotoxin, hIL13-PE38QQR, entered Phase III clinical trials in 2004 and is a Fast Track drug (Kunwar et al. (2003) J. Neurosurgery 98:697).

Fra-1-based conjugates are also embraced by this invention. As with ephrinA1 and IL-13, Fra-1-based conjugates can be fused to PE or DT molecules at either the amino terminus, e.g., DT390-Fra-1, or the carboxyl terminus, e.g., Fra-1-PE38QQR and Fra-1-PE4E.

6. Pharmaceutical Formulations.

The active compounds, conjugates, and/or compositions thereof described herein may be formulated for administration in a pharmaceutical carrier in accordance with known techniques. See, e.g., Remington, *The Science and Practice of Pharmacy* ($9^{th}$ Ed. 1995). In the manufacture of a pharmaceutical formulation according to the invention, the active compound(s) (including the physiologically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound(s) as a unit-dose formulation, for example, a tablet, which may contain from 0.01 or 0.5% to 95% or 99% by weight of the active compound. One or more active compounds may be incorporated in the formulations of the invention, which may be prepared by any of the well-known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active compound which is being used.

Particular routes of parenteral administration include intrathecal injection, including directly into the tumor or a tumor resection cavity, and intraventricular injection into a ventricle of the brain.

Active compounds and compositions may be administered by intratumor injection (including tumors in any region such as tumors of the brain), or in the case of brain tumors injection into a ventricle of the brain.

Formulations of the present invention suitable for parenteral administration comprise sterile aqueous and non-aqueous injection solutions of the active compound, which preparations are preferably isotonic with the blood of the intended recipient. These preparations may contain antioxidants, buffers, bacteriostats and solutes that render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound or composition in a unit dosage form in a sealed container. The compound or composition is provided in the form of a lyophilizate that is capable of being reconstituted with a suitable pharmaceutically acceptable carrier to form a liquid composition suitable for injection thereof into a subject. The unit dosage form typically comprises from about 10 mg to about 10 grams of the compound or composition. When the compound or composition is substantially water-insoluble, a sufficient amount of emulsifying agent that is physiologically acceptable may be employed in sufficient quantity to emulsify the compound or composition in an aqueous carrier. One such useful emulsifying agent is phosphatidyl choline.

Further, the present invention provides liposomal formulations of the compounds disclosed herein and compositions thereof. The technology for forming liposomal suspensions is well known in the art. When the compound or composition thereof is an aqueous-soluble composition, using conventional liposome technology, the same may be incorporated into lipid vesicles. In such an instance, due to the water solubility of the compound or composition, the compound or composition will be substantially entrained within the hydrophilic center or core of the liposomes. The lipid layer employed may be of any conventional composition and may either contain cholesterol or may be cholesterol-free. When the compound or composition of interest is water-insoluble, again employing conventional liposome formation technology, the composition may be substantially entrained within the hydrophobic lipid bilayer that forms the structure of the liposome. In either instance, the liposomes that are produced may be reduced in size, as through the use of standard sonication and homogenization techniques.

Liposomal formulations containing the compounds disclosed herein or compositions thereof (e.g., ephrinA1 in monomeric form, or a conjugate thereof; IL-13 conjugates, and Fra-1 conjugates), may be lyophilized to produce a lyophilizate, which may be reconstituted with a pharmaceutically acceptable carrier, such as water, to regenerate a liposomal suspension. Examples of liposomal formulations that can be used include the neutral lipid 1,2-dioleoyl-sn-glycero-3-phosphatidylcholine (DPOC) (See, e.g., Landen Jr. et al. (2005) Cancer Res. 65:6910-6918).

Other pharmaceutical compositions may be prepared from the water-insoluble compounds disclosed herein, or compositions thereof, such as aqueous base emulsions. In such an instance, the composition will contain a sufficient amount of pharmaceutically acceptable emulsifying agent to emulsify the desired amount of the compound or composition thereof. Particularly useful emulsifying agents include phosphatidyl cholines, and lecithin.

In addition to active compounds, the pharmaceutical compositions may contain other additives, such as pH-adjusting additives. In particular, useful pH-adjusting agents include acids, such as hydrochloric acid, bases or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. Of course, as indicated, the pharmaceutical compositions of the present invention may be lyophilized using techniques well-known in the art.

The therapeutically effective dosage of any one active agent, the use of which is in the scope of present invention, will vary somewhat from compound to compound, and patient to patient, and will depend upon factors such as the age and condition of the patient and the route of delivery. Such dosages can be determined in accordance with routine pharmacological procedures known to those skilled in the art.

As a general proposition, the initial pharmaceutically effective amount of the active compound or composition administered parenterally will be in the range of about 0.1 to 50 mg/kg of patient body weight per day, with the typical initial range of antibody used being 0.3 to 20 mg/kg/day, more preferably 0.3 to 15 mg/kg/day. The desired dosage can be delivered by a single bolus administration, by multiple bolus administrations, or by continuous infusion administration of active compound, depending on the pattern of pharmacokinetic decay that the practitioner wishes to achieve.

The active compound(s) is suitably administered to the patient at one time or over a series of treatments. Depending on the type and severity of the disease, about 1 µg/kg to 15 mg/kg (e.g. 0.1-20 mg/kg) of active compound(s) is an initial candidate dosage for administration to the patient, whether, for example, by one or more separate administrations, or by continuous infusion. A typical daily dosage might range from about 1 µg/kg to 100 mg/kg or more, depending on the factors mentioned above. For repeated administrations over several days or longer, depending on the condition, the treatment is sustained until a desired suppression of disease symptoms occurs. The preferred dosage of the active compound will be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g., such that the patient receives from about two to about twenty, e.g. about six doses of the anti-ErbB2 antibody). An initial higher loading dose, followed by one or more lower doses may be administered. An exemplary dosing regimen comprises administering an initial loading dose of about 4 mg/kg, followed by a weekly maintenance dose of about 2 mg/kg of the active compound. However, other dosage regimens may be useful. The progress of this therapy is easily monitored by conventional techniques and assays.

Subjects treated by the methods of the present invention can also be administered one or more additional therapeutic agents. See U.S. Pat. No. 5,677,178. Chemotherapeutic agents may be administered by methods well known to the skilled practitioner, including systemically, direct injection into the cancer, or by localization at the site of the cancer by associating the desired chemotherapeutic agent with an appropriate slow release material or intra-arterial perfusing of the tumor. The preferred dose may be chosen by the practitioner based on the nature of the cancer to be treated, and other factors routinely considered in administering. See, e.g., U.S. Pat. No. 7,078,030.

Subjects may also be treated by radiation therapy, including, but not limited to, external beam radiotherapy, which may be at any suitable dose (e.g., 20 to 70 Gy or more per tumor, typically delivered over a fractionated schedule).

Pharmaceutical compositions containing monomeric ephrinA1 in unlabeled form may be administered to subjects as blocking reagents, in like manner as described in Abrams et al., U.S. Pat. No. RE38,008, in conjunction with the administration of monomeric ephrinA1 coupled to a therapeutic group.

Monomeric ephrinA1 coupled to a diagnostic group may also be used in vitro as histological reagents on tissue samples, where binding of the ephrinA1 is indicative of cancer tissue in the tissue sample.

7. Combination Therapies.

Growth factor or cytokine receptors on tumor cells are attractive targets for tumor diagnosis, imaging, and therapy of gliomas provided that they offer widespread distribution, high levels of expression, and are specific for cancer cells (Debinski W. (2002) Molecular "Targeting of Brain Tumors with Cytotoxin," In: Chimeric Toxins (Lorberboum-Galski & Lazarovici, eds., Harwood Academic Publishers) pp. 222-246; Debinski (2002) Cancer Invest. 20:801-809). One such target is a receptor (R) for the immune regulatory cytokine, interleukin-13 (IL-13) (McKenzie et al. (1993) Proc. Natl. Acad. Sci. USA 90:3735-3739; Minty et al. (1993) Nature 362:248-251). The uniqueness of this cytokine is that its cancer-related receptor is present at limited amounts on several normal tissues. Furthermore, the binding to and physiological signaling by IL-13 on normal cells and tissues is specifically achieved through a high-affinity, heterodimeric receptor complex, which it shares with IL-4. Malignant glioma cells, on the other hand, express on their surfaces primarily a non-signaling monomeric form of the IL-13R to which IL-4 can neither bind nor transmit a signal.

This monomeric IL-13 receptor is now a molecularly defined protein and termed IL-13R$\alpha$2 (Mintz et al. (2002) Neoplasia 4:388-399). This restricted receptor is one of the first three factors ever documented to be expressed in a majority of patients with GBM and not in normal brain (Murphy et al. (1995) Gene 159:131-135; Rich et al. (1996) Gene 180:125-130). Numerous experiments further supported the notion that molecular targeting of IL-13R$\alpha$2 is an attractive strategy for molecular detection and treatment of GBM. Targeted cytotoxic therapy, targeted gene therapy, targeted radiation therapy, and targeted chemotherapy all have the potential of being applied to patients with HGGs. Several therapeutic approaches are being developed with this target in mind, including vaccines (Okano et al. (2002) Clin. Cancer Res. 8:2851-2855; Mintz et al. (2002) Neuro-Oncology 4(4):334; targeted viruses (Zhou et al. (2002) Proc. Natl. Acad. Sci. USA 99:15124-15129), re-targeted cytotoxic T cells (Kahlon et al. (2004) Cancer Res. 64:9160-9167) and new IL-13-based cytotoxins (Li et al. (2002) Prot. Engin. 15:419-427; Mintz et al. (2003) J. Neuro-Oncol. 64:117-123). Thus, one embodiment of the present invention embraces targeting IL-13R$\alpha$2 in the treatment of cancer.

Fra-1 is a member of the Fos family of AP-1 transcription factors, which include c-Fos, FosB and Fra-2. These proteins form heterodimers with the Jun family of AP-1 transcription factors, bind to AP-1 consensus DNA-binding sites in the promoters of specific target genes, and up-regulate transcription (Curran et al. (1988) Cell 55:395-7). Genes regulated by AP-1 transcription factors include VEGF-A, uPAR, and MMP-9, proteins that have been implicated in the control of tumor cell motility and invasiveness, tumor progression, and angiogenesis (Young & Colburn (2006) Gene 379:1-11). Fra-1 over-expression has been detected in multiple human cancers including breast, head and neck, and colon (Young & Colburn (2006) Gene 379:1-11). VEGF-D, a c-Fos-inducible gene, has been shown to be over-expressed in malignant gliomas, however, these tumors do not over-express c-Fos (Debinski et al. (2001) Mol. Med. 7:598-608). Rather, it has been shown that gliomas over-express Fra-1, which is capable of modulating the malignant properties of glioma cells, including morphology, anchorage-independent growth, and tumorigenic potential (Debinski & Gibo (2005) Mol. Cancer Res. 3:237-49). Fra-1 has also been shown to have an effect on a number of other solid tumors, such as thyroid, prostate, and breast cancer, and the possibility of using Fra-1 as a therapeutic target in these malignancies and others has been explored (Young & Colburn (2006) Gene 379:1-11).

IL-13R$\alpha$2, EphA2, and Fra-1 have now been shown to be molecular denominators of GBM and are therefore attractive targets for therapies, including immunotherapy. IL-13, EphA2, and Fra-1 represent a novel combination of factors that are each expressed at high levels in a sub-set of GBM patients, but when combined are expressed in virtually all patients with GBM. Importantly, the expression of these proteins was not detected in normal brain, which makes them highly suited as targets for molecular diagnostics and therapeutics designed to spare healthy brain tissue from the harms of non-specific anti-tumor therapies. A combinatorial approach to novel drug development using these proteins as targets would spare the expensive and time-consuming process of individualized molecular profiling and should make molecularly-targeted therapies more economical and feasible.

Accordingly, the present invention embraces a therapeutic approach which targets IL-13R$\alpha$2, EphA2, and alternatively Fra-1, concomitantly to improve the outcome of patients with cancer. Treatment of a subject with cancer involves administering a treatment effective amount of a first compound that specifically binds to an Eph receptor, wherein said first compound is coupled to a first therapeutic agent, and concurrently administering a second compound that specifically binds to an IL-13 receptor to said subject in a treatment effective amount, wherein said second compound is coupled to a second therapeutic agent. In particular embodiments, the subject is concurrently administered a treatment effective amount of a third compound that specifically binds to Fra-1, wherein said third compound is coupled to a third therapeutic agent.

As used herein, the term "treating cancer" or "treatment of cancer" means to inhibit the spread of cancer, decrease tumor size, lessen or reduce the number of cancerous cells in the body, or ameliorate or alleviate the symptoms associated with the cancer. The treatment is considered therapeutic if there is a decrease in mortality and/or morbidity, or a decrease in disease burden manifested by reduced numbers of malignant cells in the body.

Administering a therapeutically effective amount or treatment effective amount is intended to provide a therapeutic benefit in the treatment or management of cancer. The specific amount that is therapeutically effective can be readily determined by the ordinary medical practitioner, and can vary depending on factors known in the art, such as the type of cancer, the patient's history and age, the stage of cancer, the co-administration of other anti-cancer agents, including radiation therapy.

Methods of the invention can be used to treat and manage patients suffering from various stages of primary cancer. Further encompassed is the treatment of patients who have been previously treated for cancer, as well as those who have not previously been treated for cancer. The invention encompasses first-line, second-line, third-line and further line cancer treatments.

Cancers that can be treated or managed using methods of the invention include but are not limited to, those associated with an increase in the expression of IL-13Rα2, EphA2, or Fra-1, e.g., breast cancer, bladder cancer, pancreatic cancer, colorectal cancer, head and neck cancer, thyroid cancer, prostate cancer, and gliomas. In particular embodiments, the cancer is GBM.

The present invention is explained in greater detail in the following non-limiting Examples.

EXAMPLES

Tissue, Cell Culture, and Antibodies.

GBM cell line U-251 MG and breast cancer cell line SK-BR-3 were obtained from the American Type Culture Collection (Manassas, Va.) and grown in DMEM with 10% FBS and 0.1 mmol/L MEM non-essential amino acids (SIGMA) or RPMI with 10% FBS, respectively. Conditioned media was collected from sub-confluent monolayers and centrifuged to pellet any non-soluble debris; supernatant was collected and used immediately or stored at −20° C. until use. Cells were photographed by phase contrast microscopy and images were processed using Jasc Paint Shop Pro v. 6.01. Primary rat cortical neuronal cultures were prepared as previously described (Turner et al. (2002) Exp. Neurol. 178:21-32). Recombinant mouse ephrinA1/Fc chimera and IgG1 isotype control were obtained from R&D Systems (Minneapolis, Minn.).

Human GBM tumor tissue was obtained from the operating room, snap-frozen and stored at −80° C. until use. For culture, fresh tissue was minced into small pieces, 5 mL digestion buffer (1 mg/mL collagenase Type II, 1 mg/mL collagenase Type IV, 2 mg/mL DNase, 4% NUSERUM in DMEM) was added, and the mixture was applied to a tissue homogenizer, collected, and incubated 45 minutes at 37° C. with shaking Cells were washed and established for cell culture in RPMI-1640 (INVITROGEN, Carlsbad, Calif.), 10% FBS (SIGMA, St. Louis, Mo.), 100 µg/mL Sodium Pyruvate, 20 µg/mL L-Proline (SIGMA), 1× HT Supplement consisting of 0.1 µM Sodium Hypoxanthine and 0.016 µM Thymidine, 5 units/mL Penicillin G and 5 units/mL Streptomycin Sulfate (INVITROGEN). Human GBM xenograft tumors were provided as a generous gifts from Dr. C. David James (UCSF, San Francisco, Calif.). Tumors were dissociated and cultured in DMEM (INVITROGEN) with 10% FBS to obtain cell lines, and used for analysis within the first 5 passages.

Anti-ephrinA1, anti-EphA2, anti-Fra-1 and donkey anti-goat IgG-HRP were obtained from Santa Cruz Biotechnology (Santa Cruz, Calif.). Anti-EphA2 B208 antibody was provided by MedImmune, Inc (Gaithersburg, Md.). Anti-EphA2 D7, anti-β-actin, anti-phosphotyrosine PY20, goat anti-mouse IgG-HRP and goat anti-rabbit IgG-HRP were obtained from SIGMA (St. Louis, Mo.). Anti-IL-13Rα2 was obtained from R&D Systems (Minneapolis, Minn.). Anti-phoso-Erk and anti-Erk were obtained from Cell Signaling Technology, Inc. (Danvers, Md.). Goat-anti-mouse IgG Oregon Green was obtained from Molecular Probes (Eugene, Oreg.). Anti-GFAP was obtained from Dako (Carpinteria, Calif.) and was used to stain cells grown on 12 mm coverslips and fixed in 10% formalin followed by incubation with donkey anti-rabbit rhodamine (Jackson Immuno Research Laboratories, Inc., West Grove, Pa.).

Immunohistochemistry.

Immunofluorescence of U-251 and SK-BR-3 cell lines was performed as described previously (Wykosky et al. (2005) Mol. Cancer Res. 3:541-551). Primary antibodies EphA2 monoclonal (1:200) and ephrinA1 (1:200) were diluted in 1.5% NGS and incubated overnight at 4° C. Slides were washed twice in PBS and incubated with secondary antibody for 45 min at room temperature. Secondary antibodies included donkey anti-rabbit rhodamine (1:200) (Jackson ImmunoResearch Laboratories, Inc., West Grove, Pa.) or goat anti-mouse IgG Oregon Green (1:200) (Molecular Probes, Eugene, Oreg.). Slides were counterstained with Hoescht No. 33258 Nuclear Counterstain (DAPI) (1:3000). Slides were mounted with Gel-Mount (Biomeda Corp., Foster City, Calif.).

For F-actin staining, cells were grown on sterile slides, treated with ephrinA1-Fc or IgG-Fc isotype control for the desired time, then rinsed with PBS and fixed in 10% formalin for 5 min. Cells were permeabilized in PBS+0.1% Triton-X100 for 1 min, stained with A1 exaFluor 488 phalloidin (1:200, Molecular Probes) and DAPI (1:3000) for 1 hr, rinsed in PBS, and mounted with Gel-Mount. Photomicrographs were taken with a 40× magnification oil immersion lens with a Zeiss Axiovision camera, and images were processed with Jasc Paint Shop Pro v6.01.

Tissue microarrays were obtained from Cybrdi, Inc (Gaithersburg Md.). Histiligical designations of tumor grade for each section were verified by a neuropathologist (CS). Slides were heated at 65° C., de-paraffinized in xylene, and re-hydrated. Antigen retrieval was performed with 10 mM sodium citrate buffer, pH 6.0, by microwaving twice for 5 minutes. Endogenous peroxidase activity was quenched by incubating slides for 30 minutes in peroxide/methanol. EphA2 and Fra-1 staining was performed using the SEN-SITEK HRP Anti-Polyvalent kit (SCYTEK Laboratories, Logan, Utah). Slides were blocked and incubated with primary antibody or PBS overnight at 4° C., followed by incubation with ScyTek biotinylated secondary antibody for 15 minutes, then SCYTEK Avidin-HRP for 20 minutes. IL-13Rα2, staining was performed using R & D Systems Cell & Tissue Staining Kit according to the manufacturer. Visualization with SCYTEK AEC/Chromagen was performed and allowed to proceed for 3-5 minutes. Slides were counterstained in hematoxylin for 1 minute, and mounted with Crystal-Mount (Biomedia, Beaufort, S.C.). Photomicrographs were taken with a 40× magnification lens with a Retiga 4000 camera using ImagePro Plus v5.1. Images were processed with Jasc Paint Shop Pro v6.01. Tissue sections were scored (i) based on the average percentage range of specific positive-stained cells within the entire section and assigned to one of the following frequency categories: 0-10%, 10-50%, or 50-100% positive-staining cells and (ii) based on the overall specific staining intensity for a given marker throughout the section and assigned a score of 0, none; 1, weak; 2, moderate; or 3, strong. A1 l sections were scored blindly by one person using a 20× objective lens. Diagnosis was first confirmed and then the staining frequency and intensity was validated independently by a neuropathologist (CS). Twelve percent of scores were initially different, all within one degree of staining category on the chosen scales. Discrepancies were discussed and resolved, resulting in 8% of scores differing from the original score. Notably, among the specimens in question, ⅔ were grade II astrocytomas.

Western Blot Analysis.

Western blotting and immunoprecipitation were performed as described (Wykosky et al. (2005) Mol. Cancer Res. 3:541-51). Media Membranes were incubated with primary antibody overnight at 4° C., and with secondary antibody conjugated with horseradish peroxidase (goat anti-mouse IgG, goat anti-rabbit IgG, or donkey anti-goat IgG) 1 hour at room temperature. Detection was performed using the ECL plus Western Blotting Detection System (GE Healthcare, Piscataway, N.J.). Membranes were exposed to autoradiographic film X-OMAT AR, and films scanned at 600×dpi and images compiled using Jasc Paint Shop Pro v 6.0.

Cytotoxicity Assay.

Human GBM explant cells ($5\times10^3$ cells/well) or U-251 MG cells ($1\times10^3$ cells/well) were plated in 96-well culture plates. IL-13.PE38QQR (Debinski et al. (1998) Nat. Biotechnol. 16:449-53) and ephrinA1-PE38QQR were diluted in PBS+0.1% BSA, added to each well, and incubated at 37° C. for 48 hours. Cells treated with cycloheximide served as a positive control for cell death. Cell viability was determined using an MTS (3-(4,5-dimethylthiazol-2-yl)-5-(3-carboxymethoxyphenyl)-2-(4-sulfophenyl)-2H-tetrazolium, inner salt)/PMS (phenazine methasulfate) cell proliferation assay (PROMEGA, Madison, Wis.). Cells were incubated with the MTS/PMS dye for 2-4 hours, and absorbance measured at 490 nm using a microplate reader. Each concentration of drug was tested in quadruplicate in each assay, and viability of cells treated with drug calculated as percent of untreated control cells.

Statistical Analyses.

All data sets were analyzed by one-way ANOVA followed by Bonferroni's Multiple Comparison test to determine level of significance between pairs of data sets, with the exception of the neuronal growth cone analysis, in which Nueman-Keuls post-hoc testing was used. $p<0.05$ was considered significant. Error bars represent mean+/−S.E.M.

Example 1

Transfection of U-251 MG GBM Cells with EphrinA1

GBM cell line U-251 MG was obtained from the American Type Culture Collection (Manassas, Va.). U-251 MG cells were grown in DMEM+glutamine with 10% FBS and 0.1 mmol/L non-essential amino acids. DNA (5 μg; ephrinA1 peDNA, His-ephrinA1 pcDNA or empty vector control) was transfected into cells growing in Opti-MEM (Invitrogen, Carlsbad, Calif.) using LipofectAMINE 2000 (Invitrogen). After 24 hrs, Opti-MEM was replaced with growth medium containing 20% fetal bovine serum. 24 hr later, the cells were split into 100 mm² Petri dishes and geneticin (800 μg/mL) was added to select clones. Individual clones were isolated and maintained in appropriate growth medium containing 200 μg/mL geneticin.

To examine what form of ephrinA1 fulfills a tumor suppressor function, U-251 MG GBM cells were transfected with ephrinA1 and observed diminished EphA2 levels when the cells were confluent; this supported the membrane-anchored presence of ephrinA1 and cell-to-cell interaction responsible for EphA2 activation and ensuing degradation. Unexpectedly, when cells were not confluent, EphA2 became lower, too, suggesting a release of a monomeric full-length ephrinA1 corresponding to the gene used for transfection.

Next, a monomer of ephrinA1 was detected in the media of the U-251 MG-ephrinA1 (+) cells, but not in the media of control cells. The media of the U-251 MG-ephrinA1 (+) cells was found to contain the EphA2-decreasing activity. In addition, the media caused EphA2 phosphorylation in a dose-dependent manner confirming specific activation of the EphA2 receptor. Moreover, a previously observed ability of recombinant ephrinA1-Fc to induce profound morphological changes in GBM cells was detected in the media of U-251 MG-ephrinA1 (+) cells as well.

A. EphrinA1-producing GBM cells and breast cancer cells exhibit down-regulated EphA2 independent of cell-cell contact. To investigate the functional interplay between EphA2 and ephrinA1, U-251 MG GBM cells, which naturally express high levels of EphA2 and very low levels of ephrinA1, were stably transfected with full-length human ephrinA1 (SEQ ID NO:2). Total RNA was isolated from human umbilical vein endothelial cells and reverse transcription was used to generate corresponding cDNA. The DNA sequence corresponding to the full-length human ephrinA1 gene was amplified by PCR using oligonucleotide primers specific for the sequence of human ephrinA1. The ephrinA1 gene product was then cloned into a commercially available plasmid mammalian expression vector, pcDNA 3.1(+) (Invitrogen), at the multi-cloning site of this vector.

Western blotting revealed that three clonally selected lines (#4, #7, and #12) over-expressed ephrinA1, which migrated as an immunoreactive band of ~25 kDa (FIG. 1A). Interestingly, a dramatic decrease in EphA2 protein was observed in those cells harboring the ephrinA1 transgene, in comparison with high levels of EphA2 in parental and mock-transfected cells (FIG. 1A). Immunofluorescence revealed the same differential expression of ephrinA1 and EphA2 (data not shown). Notably, ephrinA1-specific staining in transfected cells was more diffusely cytoplasmic and perinuclear and thus different from the staining pattern seen for EphA2, suggesting that ephrinA1 in these cells is not a membrane-localized protein. Hence, GBM cells that normally express high levels of EphA2 and low ephrinA1 can be stably transfected to over-express ephrinA1 that does not localize to cell membranes, and this coincides with a marked decrease in plasma membrane-bound EphA2.

Figure 1B:
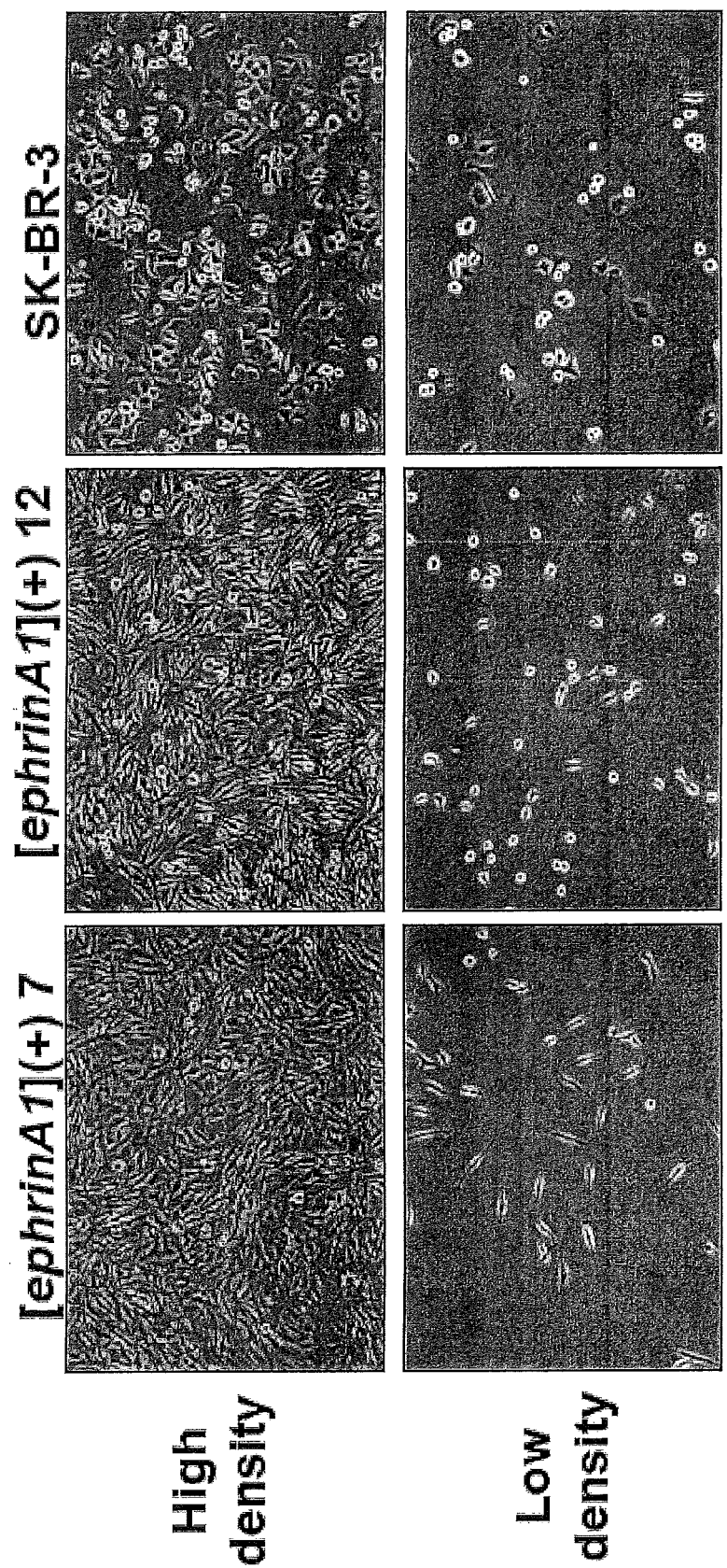

EphA2 undergoes ligand-mediated receptor internalization and degradation following activation by recombinant, homodimeric ephrinA1-Fc (Walker-Daniels et al. (2002) Mol. Cancer Res. 1:79-87). We investigated if the down-regulation of EphA2 in U-251[ephrinA1](+) cells is dependent on the extent of cell-cell contact, and potentially due to a membrane-bound form of ephrinA1. Thus, ephrinA1(+) and mock-transfected U-251 MG cells were plated at low density or grown to confluency (FIG. 1B). Also examined were SK-BR-3 cells, a breast carcinoma cell line shown previously to express high endogenous ephrinA1 and low EphA2 in cell lysates (Macrae et al. (2005) Cancer Cell 8:111-118). Breast cancer cell line SK-BR-3 was obtained from the American Type Culture Collection (Manassas, Va.). SK-BR-3 cells were grown in RPMI with 10% FBS.

Figure 1C:
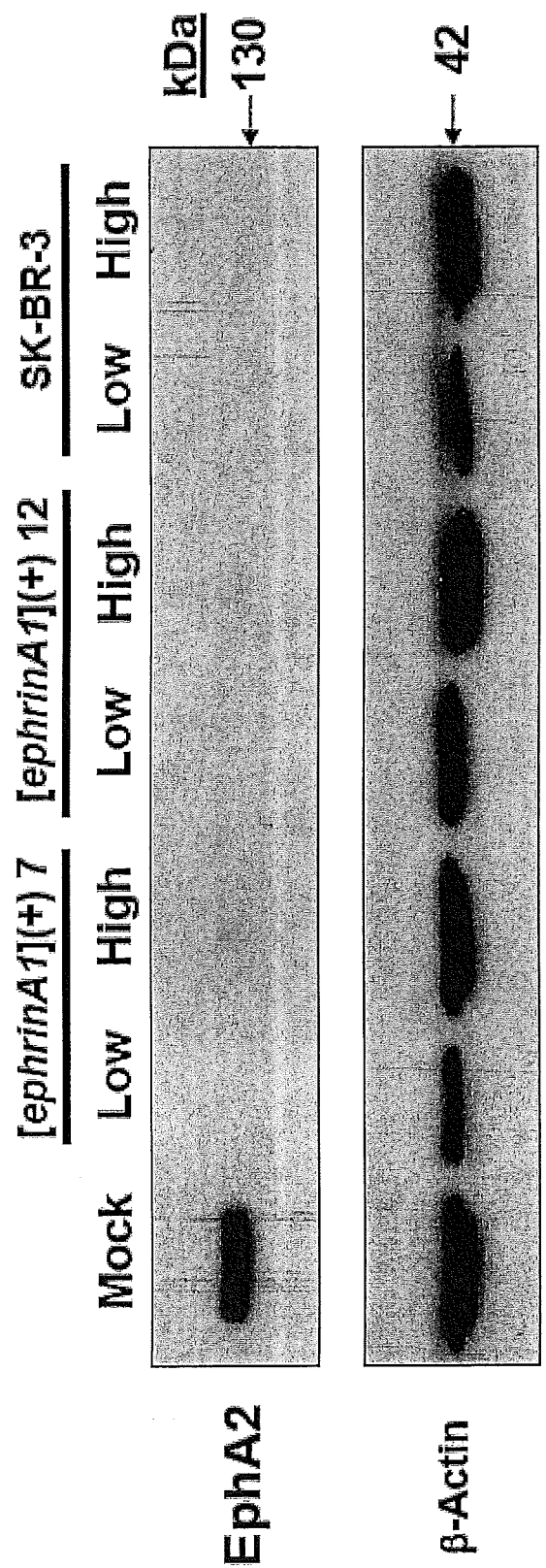

The down-regulation of EphA2 in U-251[ephrinA1](+) cells persisted despite the lack of extensive cell-cell contact (FIG. 1C). Furthermore, SK-BR-3 cells displayed undetectable levels of EphA2 at both low and high density. These findings support the notion that both ectopic and endogenous ephrinA1 is capable of down-regulating EphA2 in a manner that is not dependent on cell-cell contact.

Figure 2A:
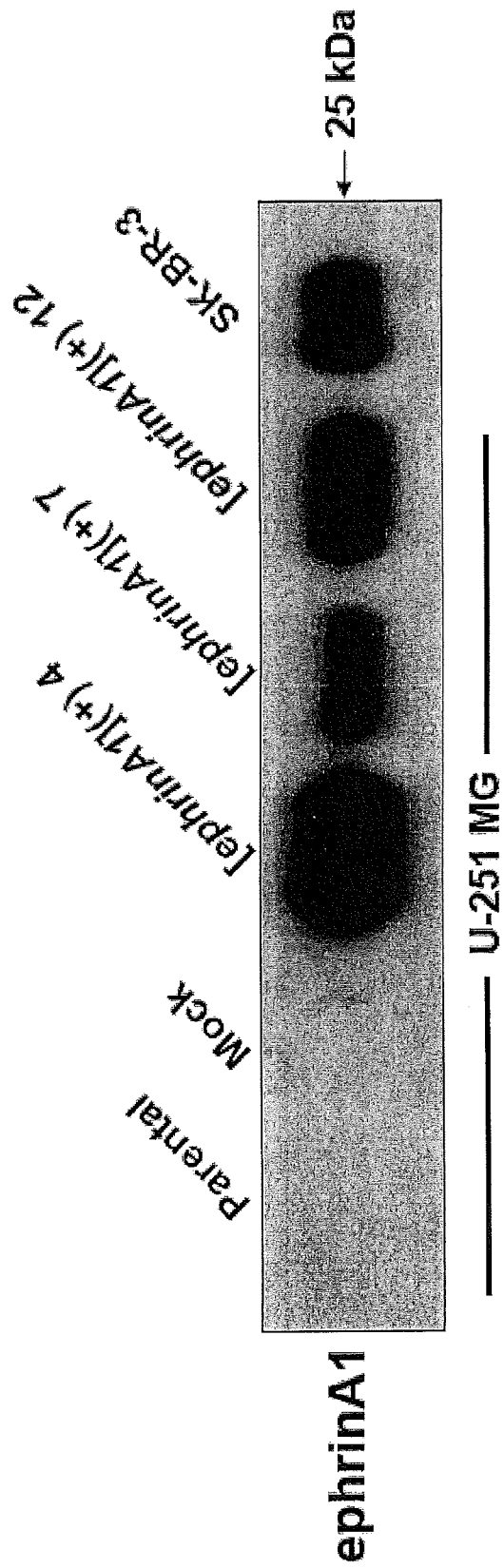
FIGS. 2A-2B. EphrinA1 expression in conditioned media under reducing and non-reducing conditions.
Figure 2B:
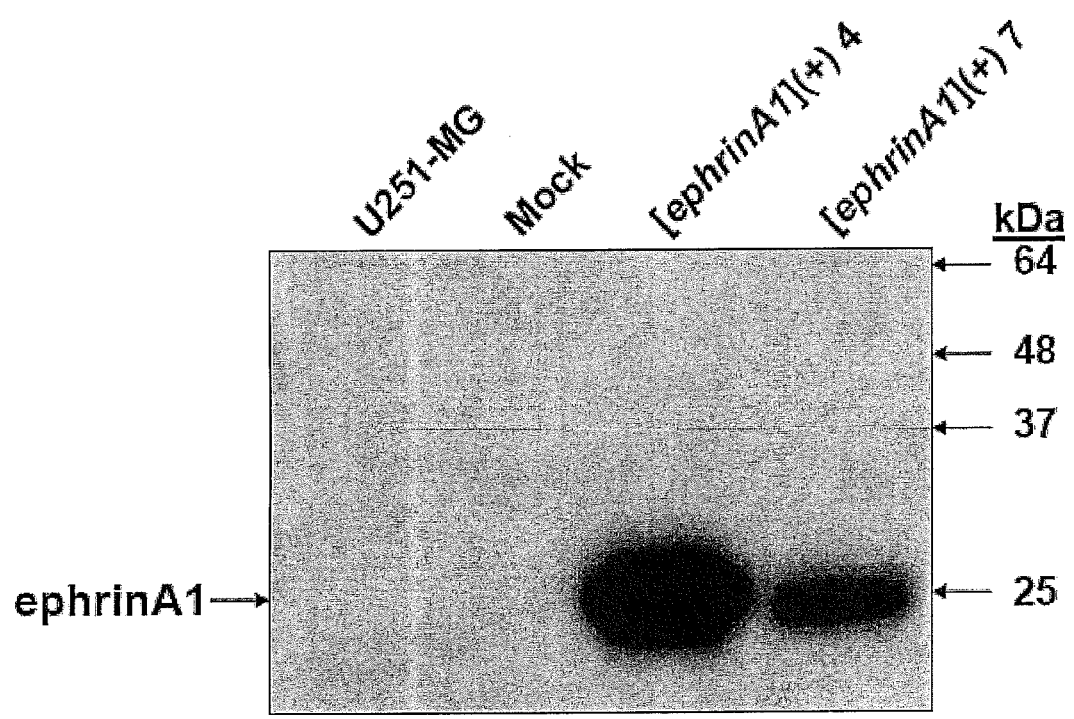

B. EphrinA1 is a soluble, monomeric protein in the media of cancer cells. To initially investigate the possible existence of soluble ephrinA1, media from U-251[ephrinA1](+) and SK-BR-3 cells was tested. Western blot analysis for ephrinA1 under reducing conditions revealed abundant expression of the protein in the media of ephrinA1-transfected and SK-BR-3 cells, but not parental or mock-transfected cells (FIG. 2A). To characterize the form of ephrinA1 in the media of transfected cells, we performed western blotting under non-reducing conditions, in which we detected a single, 25-kDa immunoreactive band corresponding to monomeric ephrinA1 in the media of the two studied U-251[ephrinA1](+) clones: #4 and #7 (FIG. 2B). There were no ephrinA1-immunoreactive proteins detected at the expected size of an ephrinA1 homodimer (50-60 kDa), suggesting that ephrinA1 is present as a monomer in the media of these cells. The same results were obtained with SK-BR-3 media under non-reducing conditions, suggesting that ephrinA1 is also a monomeric protein in cells that naturally produce the ligand (data not shown).

Figure 3A:
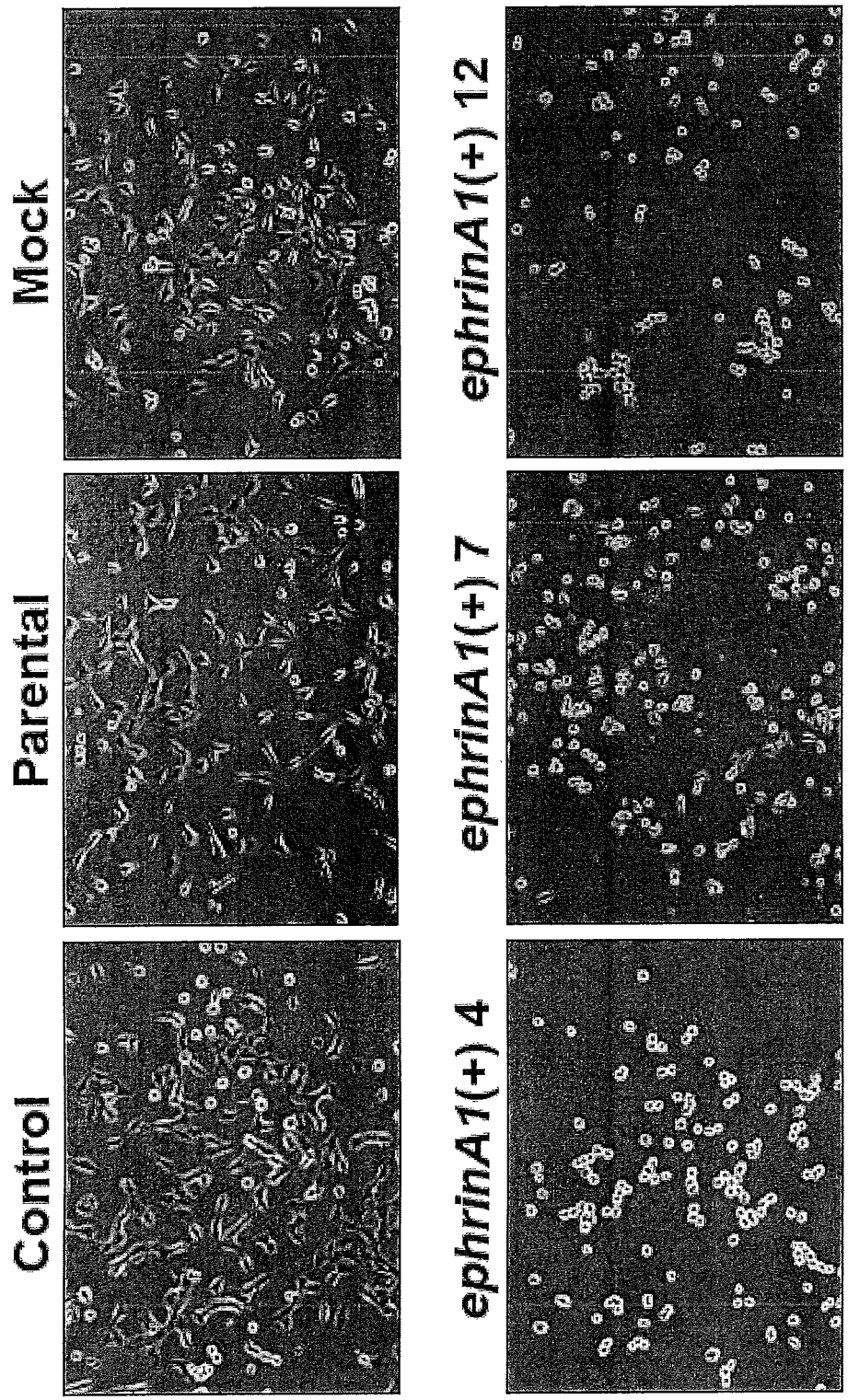
FIGS. 3A-3C. Effect of ephrinA1-conditioned media and ephrinA1-Fc on GBM cell morphology.
Figure 3B:
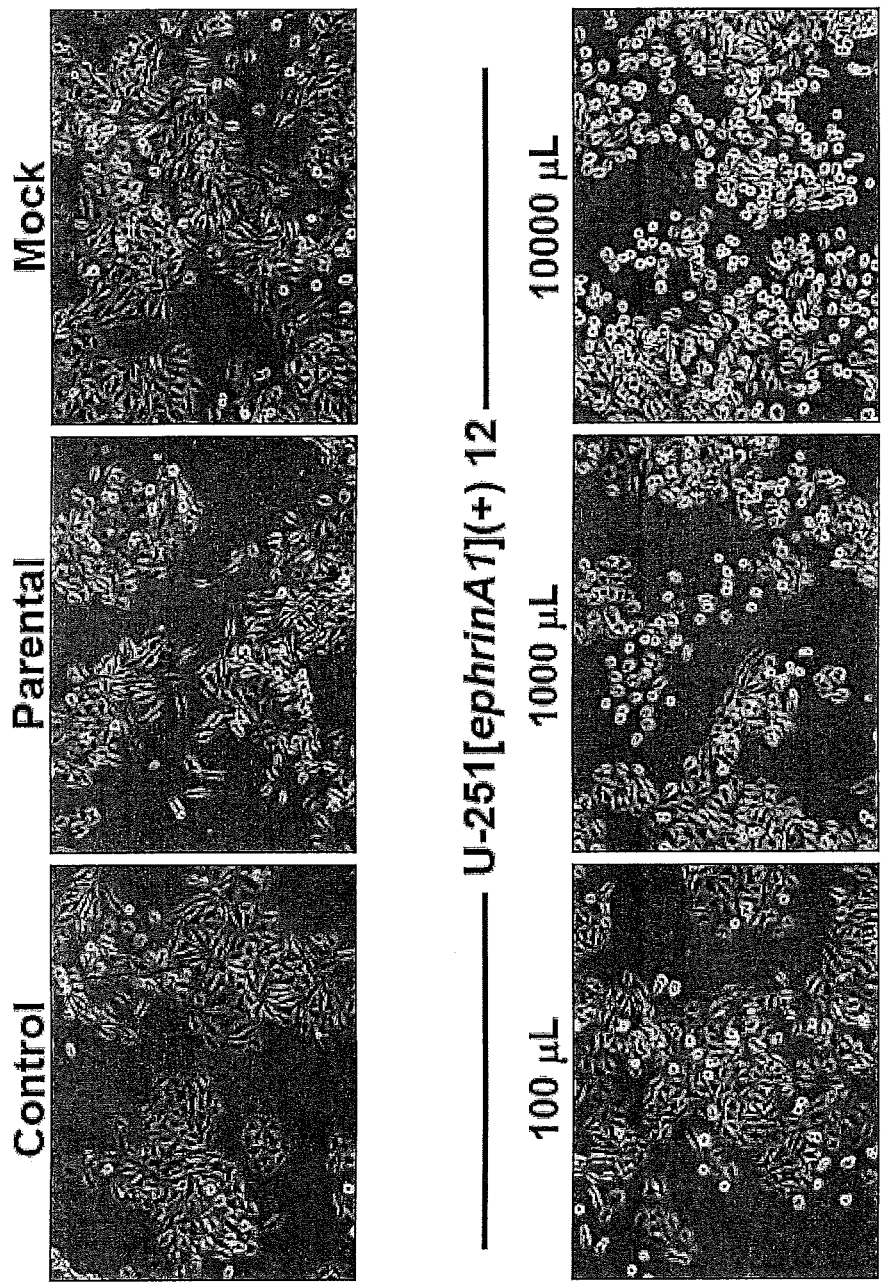
Figure 3C:
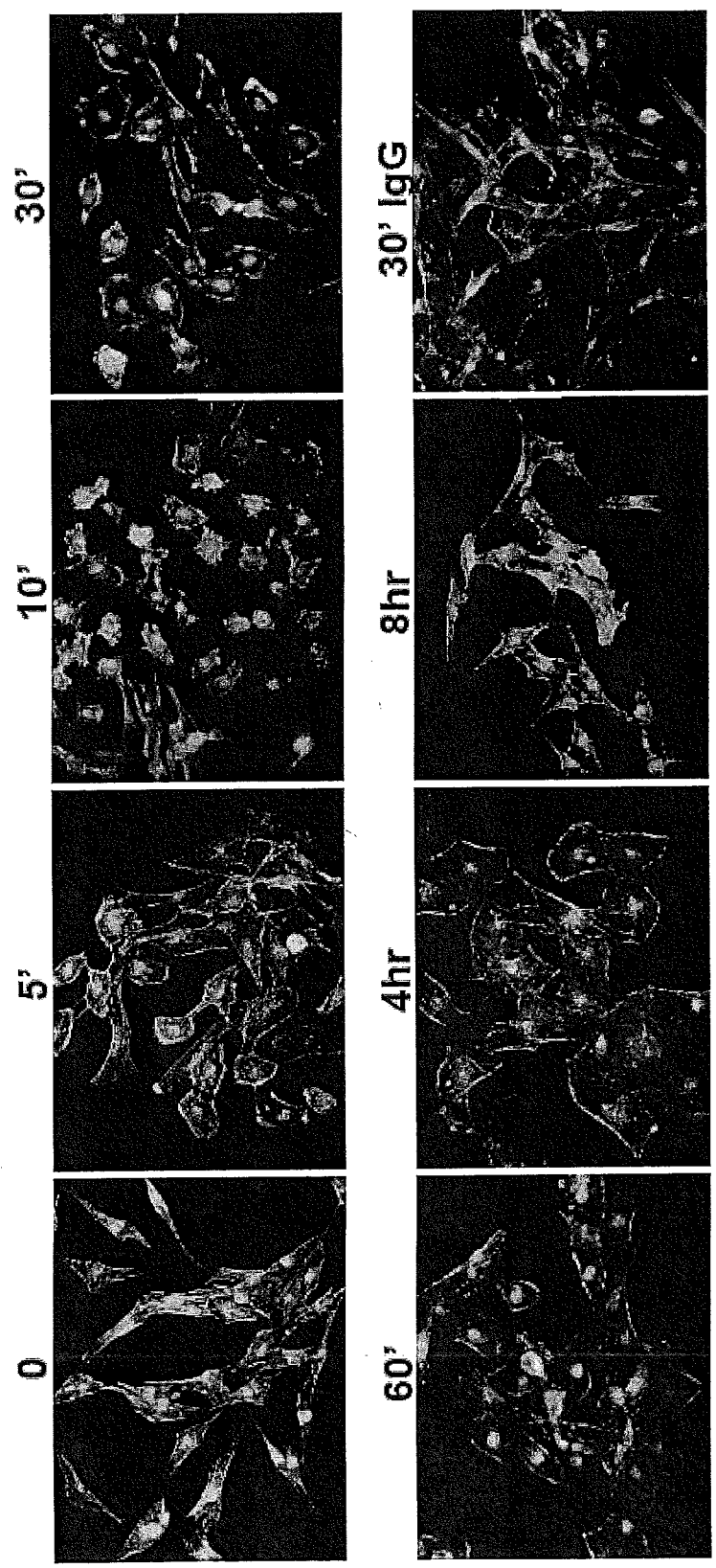

C. Monomeric, soluble ephrinA1 alters GBM cell morphology and down-regulates the EphA2 oncoprotein. Activation of EphA2 with recombinant homodimeric ephrinA1-Fc induces rapid, profound changes in the actin cytoskeleton in addition to causing receptor internalization and degradation (Miao et al. (2000) Nat. Cell Biol. 2:62-69). To explore the functional activity of soluble monomeric ephrinA1, parental U-251 MG cells were treated with media from self, mock-transfected, or U-251[ephrinA1](+) cells. Cells treated with conditioned media from control cells retained the shape typical of U-251 cells with distinct, elongated processes (FIG. 3A). However, cells treated with conditioned media from three different ephrinA1 (+) clones ("ephrinA1-conditioned media") rapidly became rounded, retracting most or all processes within 30 min (FIG. 3A). This phenomenon was dose-dependent, since its extent corresponded to the amount of conditioned media applied (FIG. 3B). Similar U-251 MG cell rounding was observed in response to treatment with recombinant dimeric ephrinA1-Fc (FIG. 3C).

Figure 4A:
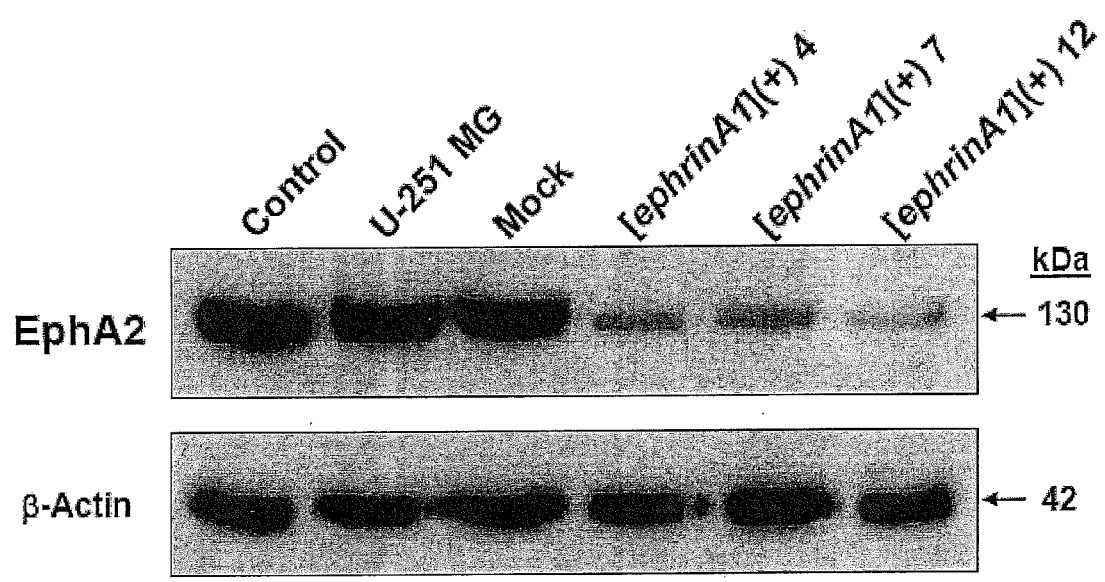
FIGS. 4A-4B. EphA2 expression in response to treatment with ephrinA1-conditioned media or ephrinA1-Fc.
Figure 4B:
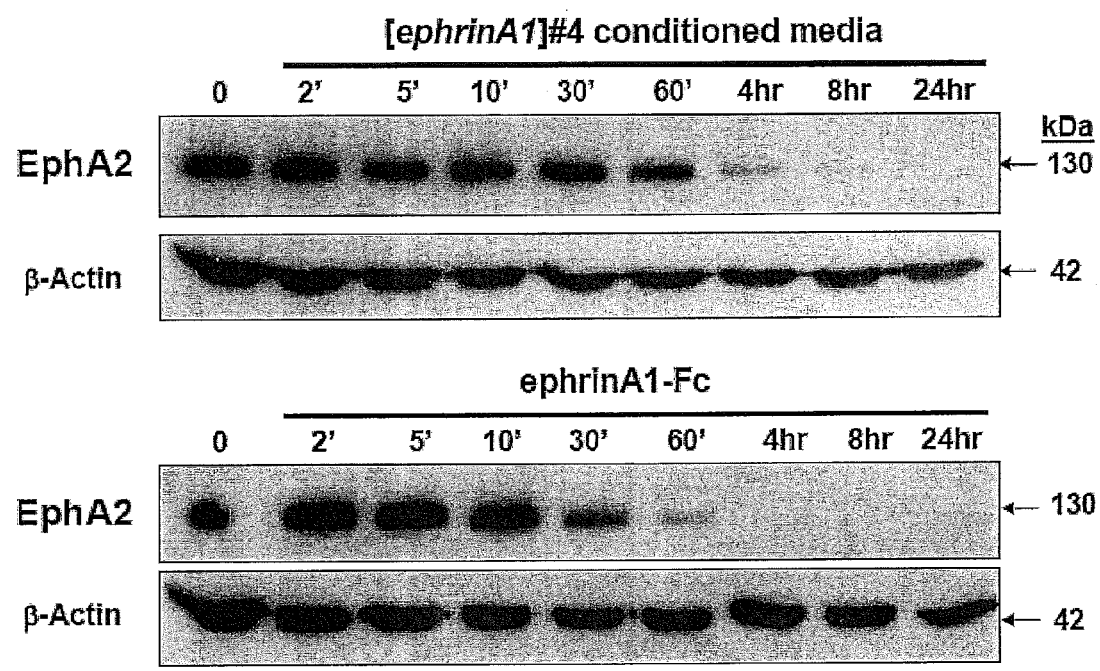

To validate the existence of functional, soluble ephrinA1 in the media of transfected cells, the effect of ephrinA1-conditioned media on the expression of EphA2 was investigated. Treatment of parental U-251 MG cells not harboring an ephrinA1 transgene with ephrinA1-conditioned media caused significant down-regulation of the receptor (FIG. 4A). The magnitude of EphA2 down-regulation in response to treatment with ephrinA1-conditioned media compared to treatment with ephrinA1-Fc was similar, although EphA2 expression began to decline after 60 min in response to ephrinA1-conditioned media and after 30 min in response to ephrinA1-Fc (FIG. 4B). In both cases, EphA2 remained suppressed for at least 24 hr in the presence of the ligand. Cells treated with parental or mock-conditioned media over time exhibited no change in the level of EphA2 whatsoever (data not shown). These results indicate that a soluble form of ephrinA1 that is present in the conditioned media of U-251[ephrinA1] (+) cells has the ability to function in a paracrine fashion on the EphA2 receptor.

Figure 5A:
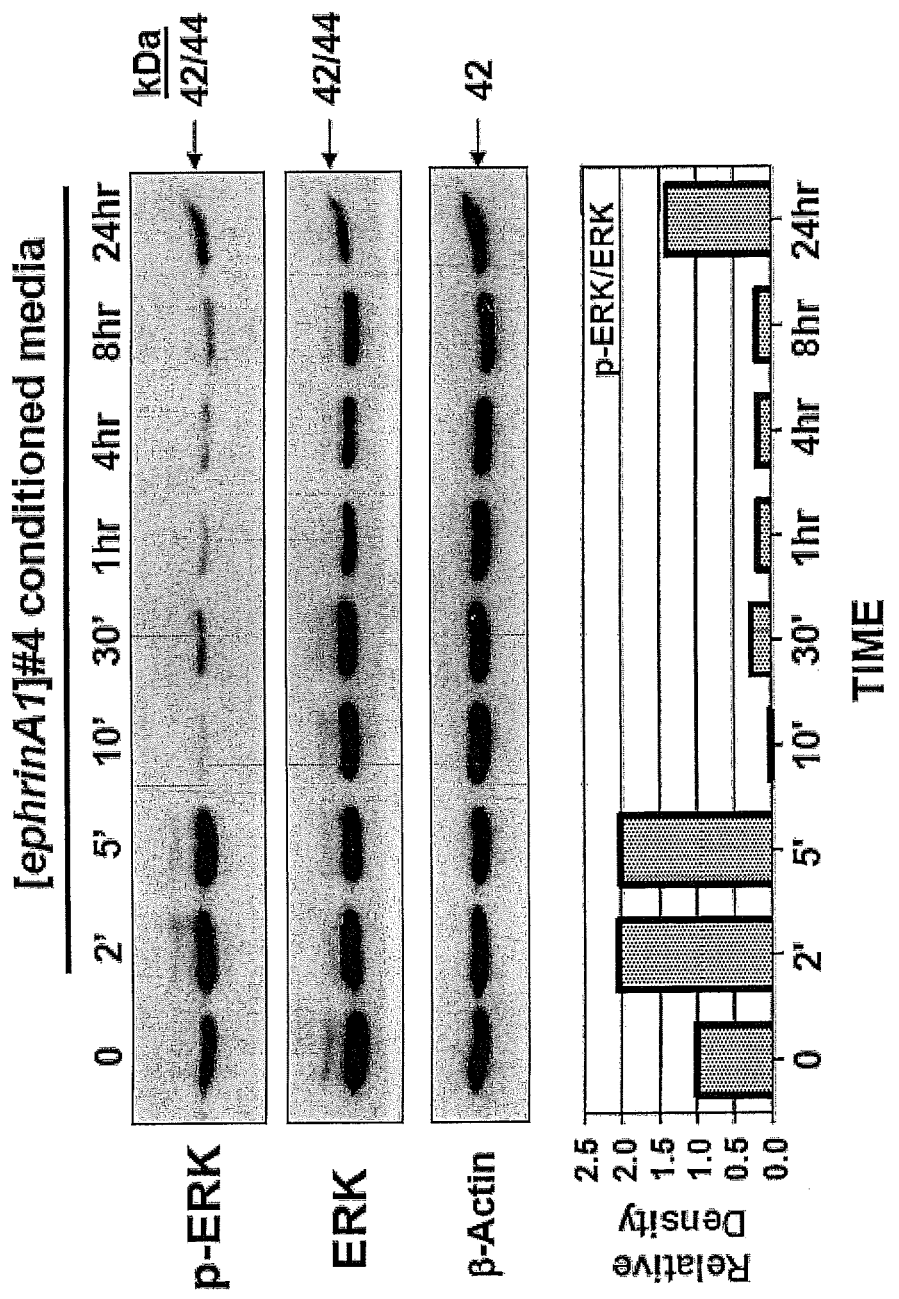
FIGS. 5A-5C. Effect of soluble, monomeric ephrinA1 and ephrinA1-Fc on the RAS-MAPK pathway and anchorage-independent growth.
Figure 5B:
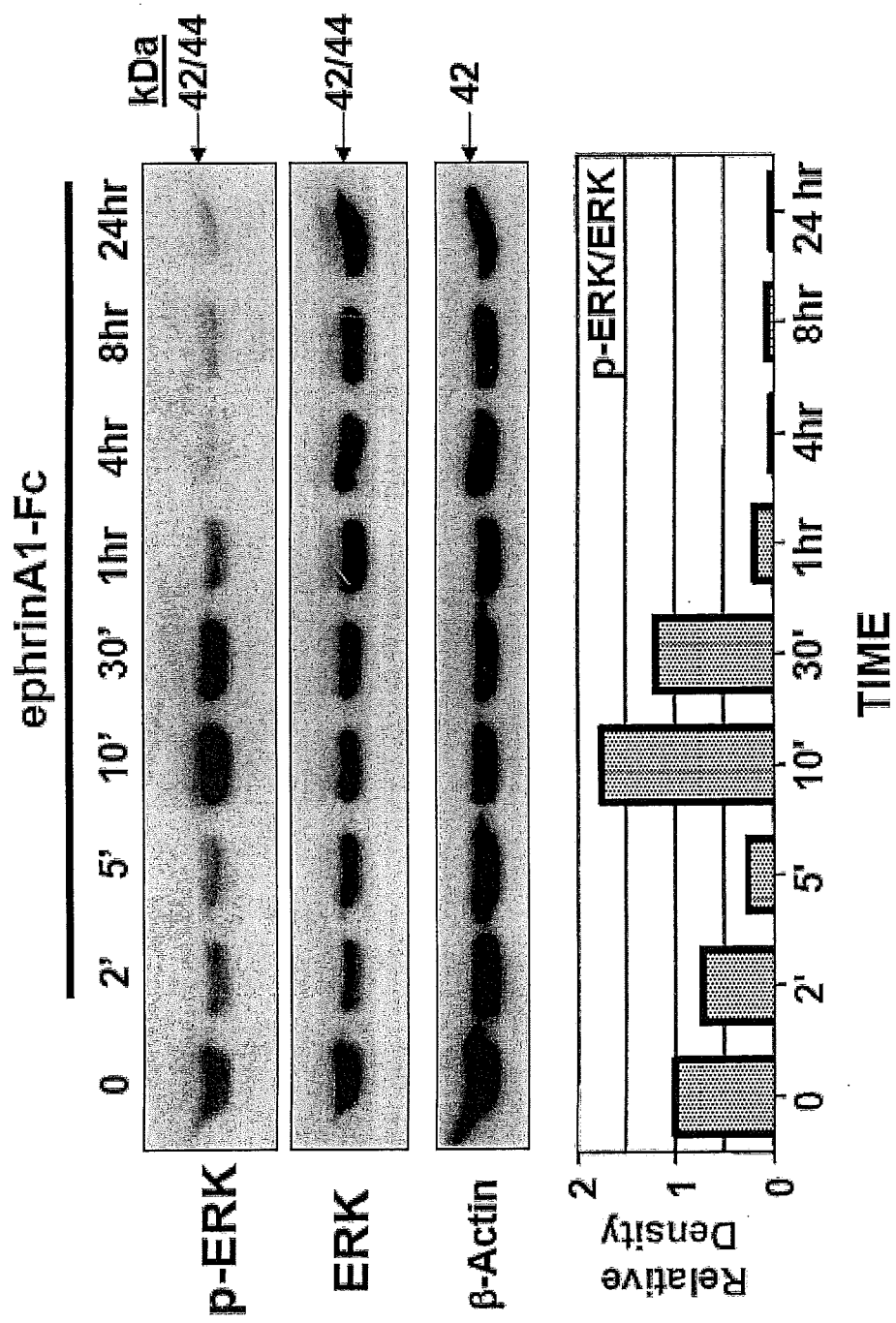

D. Soluble, monomeric ephrinA1 negatively regulates the Ras-MAPK pathway and suppresses anchorage-independent growth. Activation of EphA2 by ephrinA1 results in a suppression of signaling through the oncogenic Ras-MAPK pathway in breast and prostate cancer cells as well as in keratinocytes isolated from mouse skin (Miao et al. (2001) Nat. Cell Biol. 3:527-530; Guo et al. (2006) Cancer Res. 66:7050-7058). We investigated the effect of both ephrinA1-Fc- and ephrinA1-conditioned media on Ras-MAPK signaling downstream of EphA2 in GBM. At 10 min following treatment of U-251 MG cells with ephrinA1-conditioned media, we detected a sharp decrease in p-ERK expression (FIG. 5A). p-ERK remained suppressed up to 24 hr, at which point it had returned to baseline levels. Treatment with ephrinA1-Fc resulted in similar suppression of p-ERK, but was observed later, at about 1 hr following stimulation, and persisted through 24 hr (FIG. 5B). These observations suggest a prominent inhibition of the Ras-MAPK pathway by monomeric ephrinA1 through EphA2.

Figure 5C:
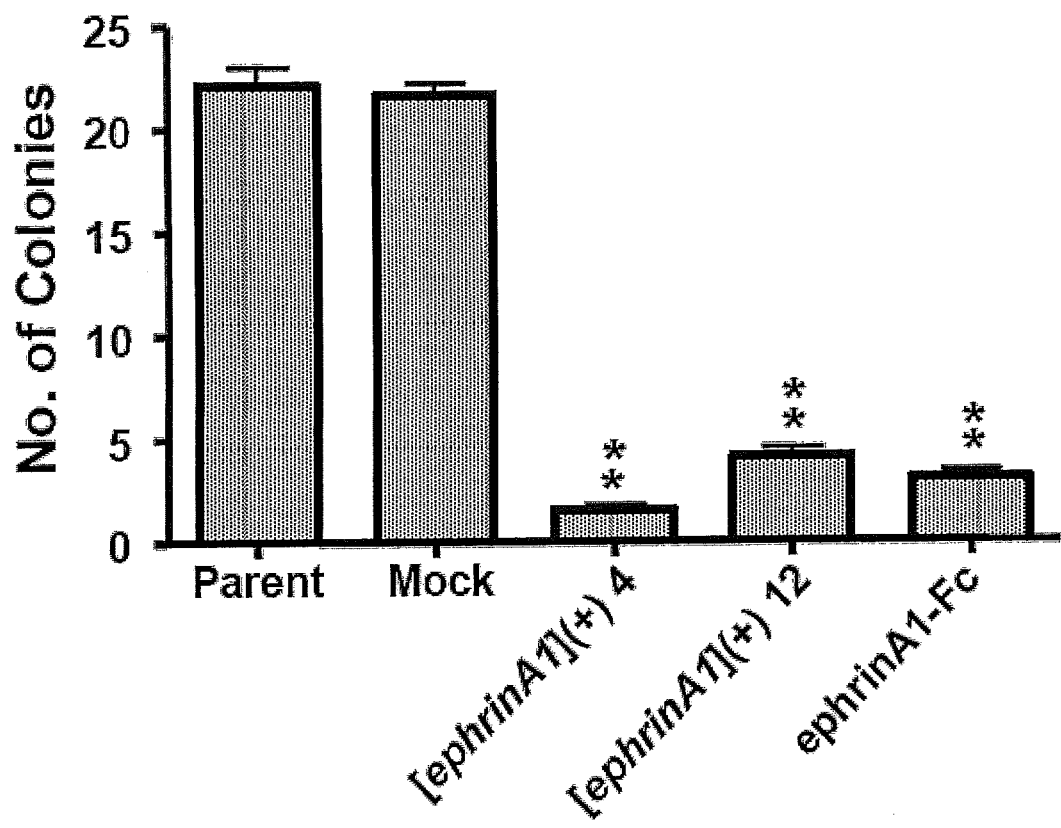

In another attempt to document a tumor-suppressing role for soluble, monomeric ephrinA1, U-251 MG cells express-ing the ligand were assessed for its effect on anchorage-independent growth. U-251[ephrinA1](+) cells (#4 and #12) displayed a dramatic impairment in the ability to form colonies in soft agar when compared to parental and mock-transfected cells (p<0.001) (FIG. 5C). Notably, the defect in anchorage-independent growth was similar for ephrinA1-producing cells and controls treated with dimeric ephrinA1-Fc.

Example 2

Transfection of U-251 MG GBM Cells with His-ephrinA1

In order to investigate the function of monomeric ephrinA1, U-251 MG cells were transfected with N-terminal 6-histidine-tagged ephrinA1 (His-ephrinA1). U-251 MG cells transfected with His-ephrinA1 were grown in 150 cm$^2$ tissue culture flasks until sub-confluent. Normal culture medium was replaced with low-serum medium containing 1% FBS for 24 hours. Conditioned media was collected and subject to buffer exchange by dialysis with binding buffer (20 mM sodium phosphate, 0.5M sodium chloride, 20 mM imidazole, pH 7.4). Dialyzed conditioned media was filtered and His-ephrinA1 purified by HisTrapHP Ni Sepharose High Performance via FPLC (Amersham, Piscataway, N.J.). Purified protein was eluted from column with binding buffer containing 500 mM imidazole. Protein was concentrated and buffer was exchanged to PBS with Microcon centrifugal filter devices (Millipore, Bedford, Md.).

Figure 6A:
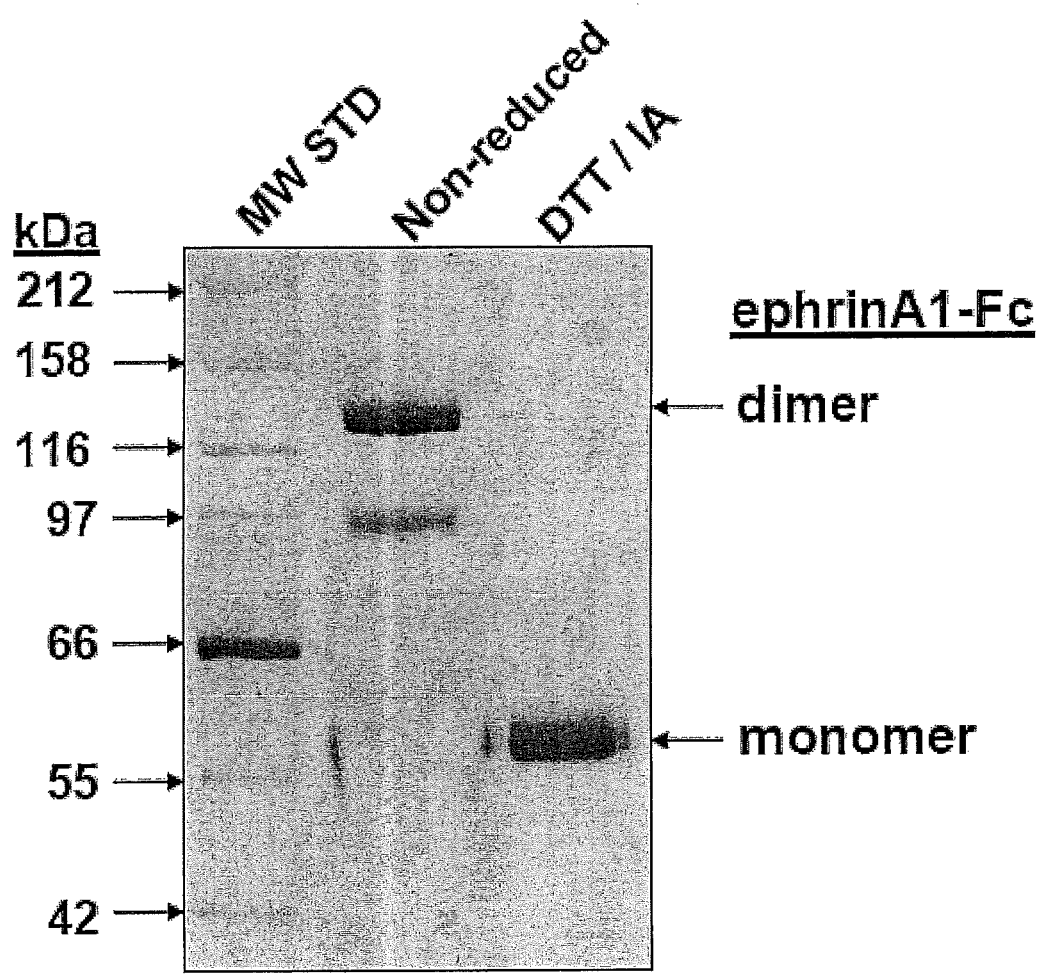
FIGS. 6A-6F. Effect of monomeric ephrinA1 on U-251 MG cell morphology, EphA2 activation, and cell migration.
Figure 6B:
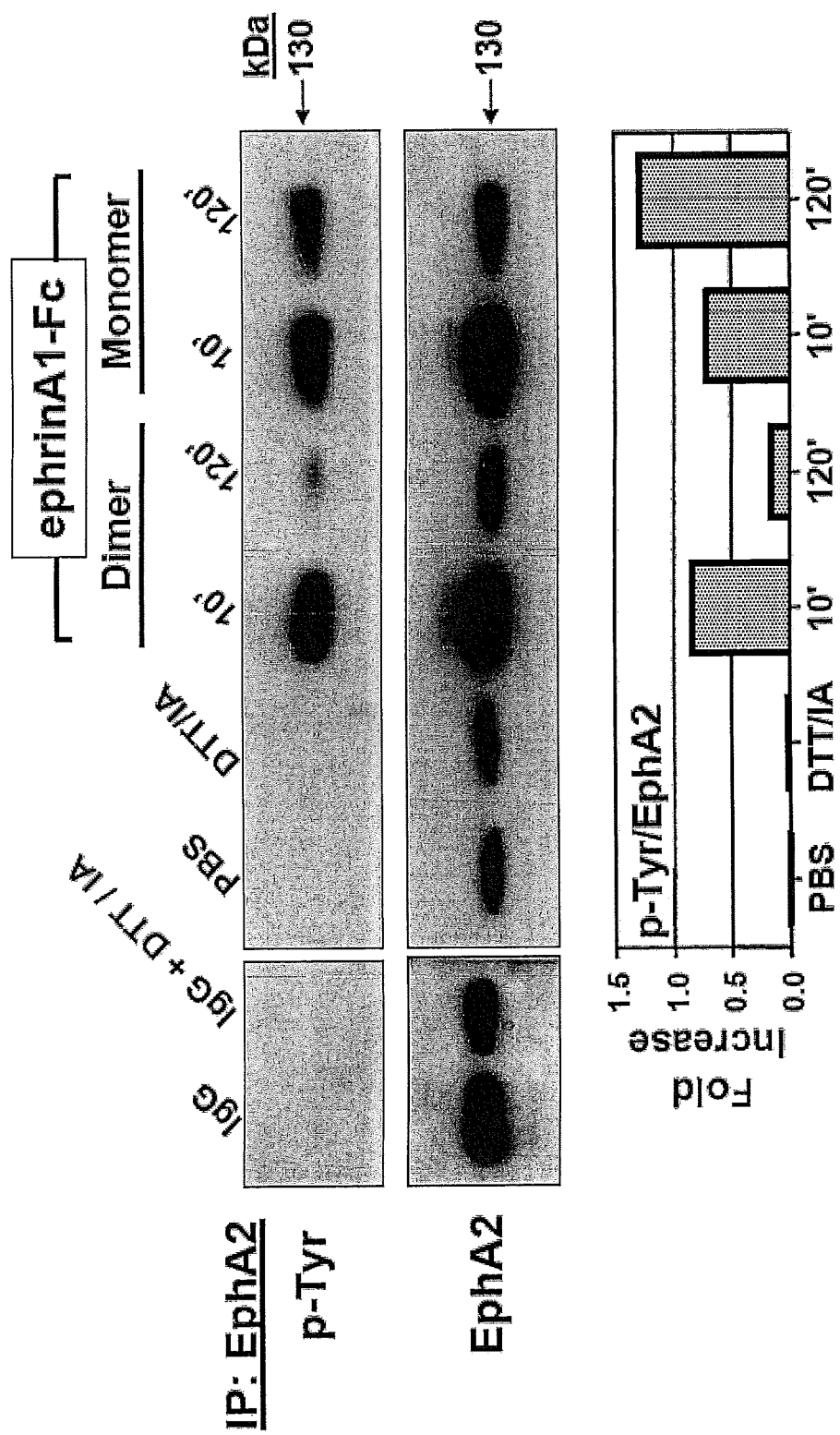

His-ephrinA1 was present as a monomer in the media of these cells and not in parental or mock-transfected cells, as seen by ephrinA1 western blotting under non-reducing conditions with two clonally selected lines (FIG. 6A). The monomeric protein was isolated from the media via Ni$^{2+}$ affinity chromatography, and was immunoreactive for ephrinA1 at the expected size of 25 kDa (FIG. 6A). This purified protein was then used to treat U-251 MG cells, which responded to, the monomeric ligand by changing cell morphology in a manner identical to ephrinA1-conditioned media and ephrinA1-Fc monomer or dimer (FIG. 6B).

Together, these results reveal that covalent dimerization and/or artificial clustering of ephrinA1 is not required for EphA2 activation or for the downstream phenotypic effects of cell rounding and migration and support the notion that soluble monomeric ephrinA1 released into the extracellular environment is a functional protein with tumor-suppressing effects on cancer cells via the EphA2 receptor.

Example 3

Reduction of a Homodimer of Recombinant ephrinA1-Fc

In another direct experiment, a homodimer of recombinant ephrinA1-Fc (R&D Systems) was reduced and the reactive sulfhydryl groups blocked. 10 mM DTT (Acros Organics, Morris Plains, N.J.) was added to recombinant mouse ephrinA1-Fc or IgG$_1$ isotype control diluted in PBS for 15 min at 37° C. Iodoacetamide (IA) (Sigma) was added at a final concentration of 20 mM and incubated at room temperature for 20 min. 10 mM DTT was added again and incubated for 15 min at 37° C. to scavenge any unused IA. Reduced products were used to treat cells, were subject to purification using Spin-OUT 12,000 Micro columns (Chemicon, Temecula, Calif.), or were visualized by separation with SDS-PAGE followed by staining with Coomassie blue.

Figure 6C:
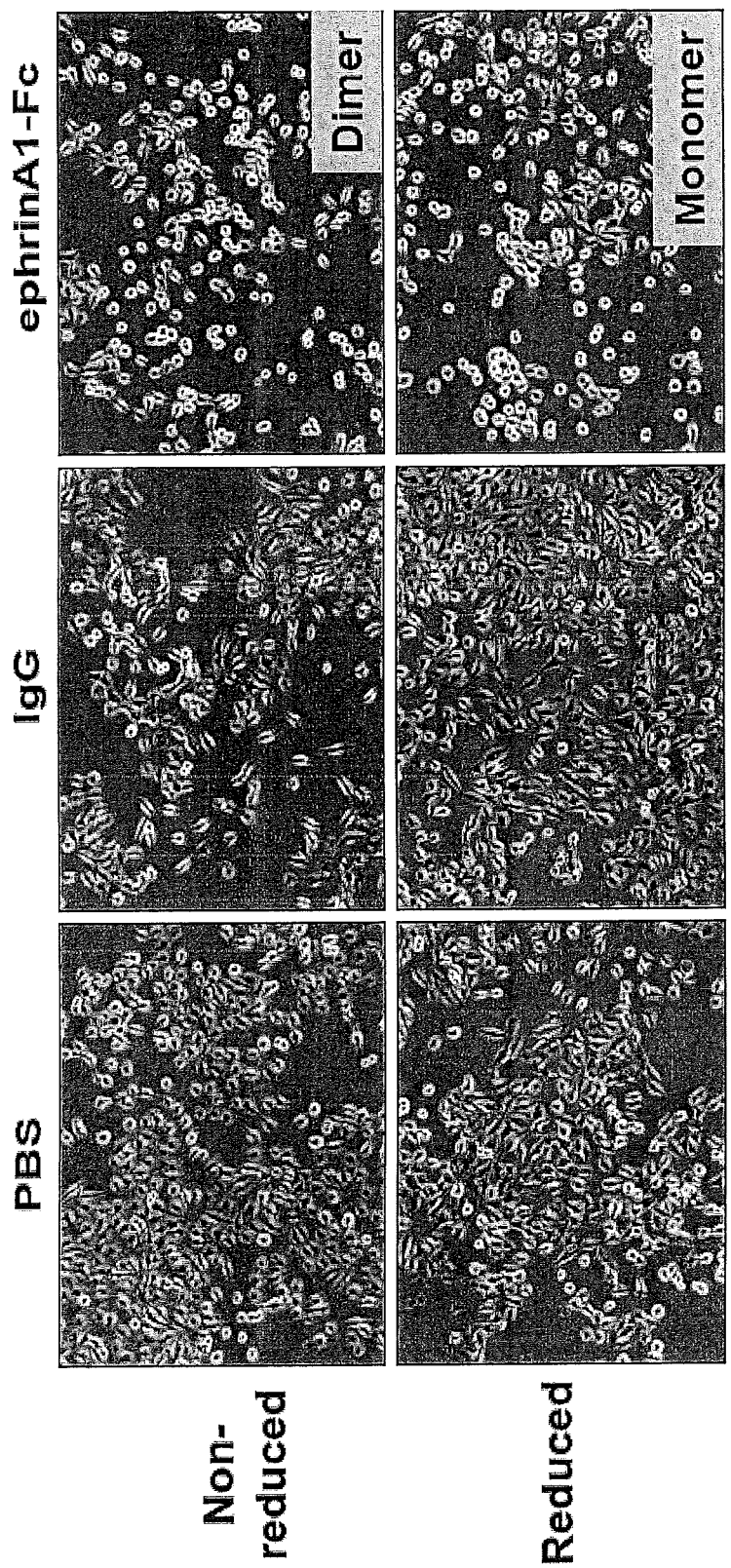

The finding that soluble ephrinA1 in conditioned media exists as a functional, monomeric protein led to an investigation into the possibility that recombinant ephrinA1-Fc (R&D Systems) may be functional in a monomeric form as well. Thus, the disulfide bonds in ephrinA1-Fc were reduced, and free thiol groups were covalently modified by iodoacetamide (IA) (Debinski et al. (1992) J. Clin. Invest 90:405-411). SDS-PAGE analysis of reduced and non-reduced proteins verified the presence of monomeric or dimeric ephrinA1-Fc, respectively (FIG. 6C).

Figure 6D:
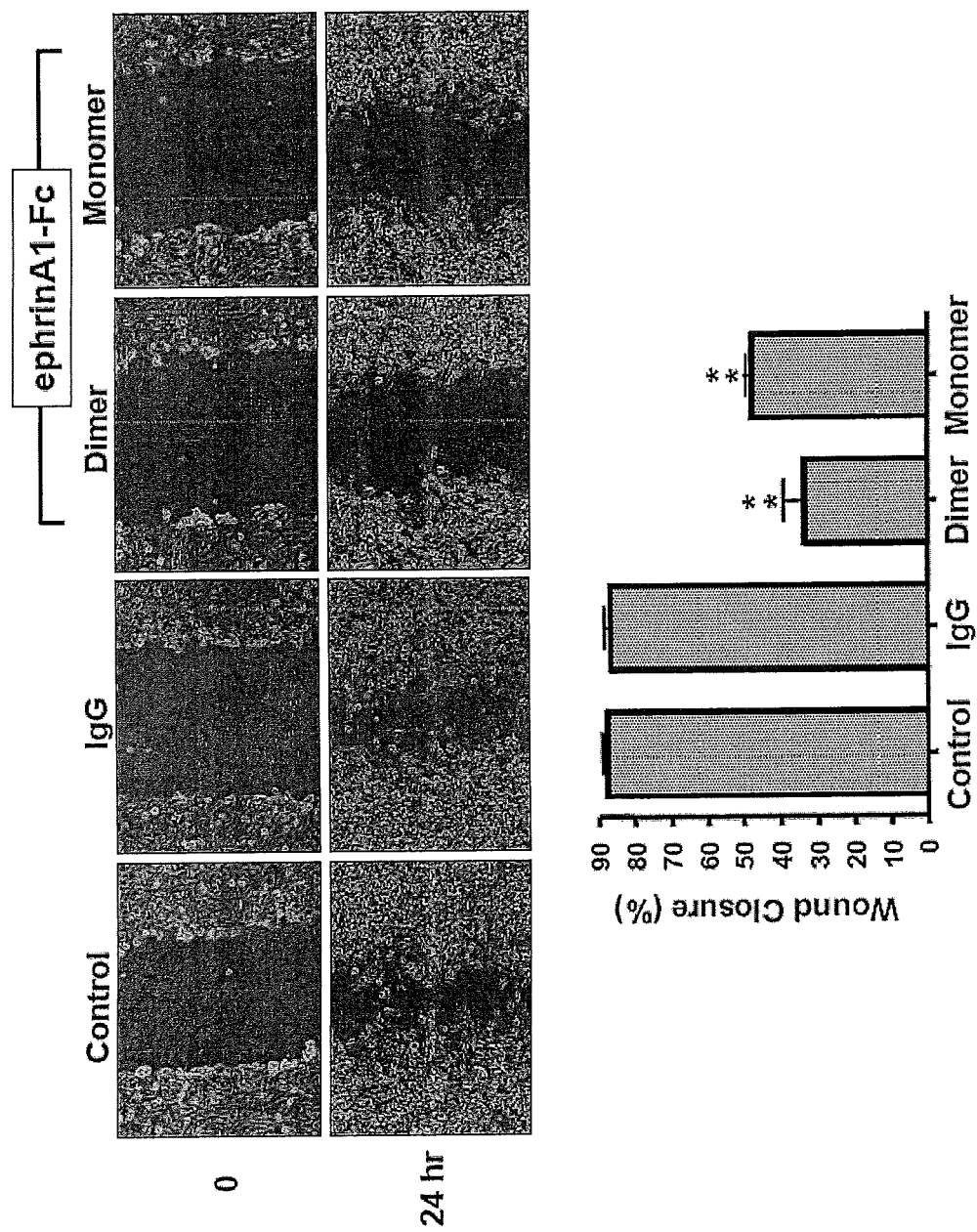
Figure 6E:
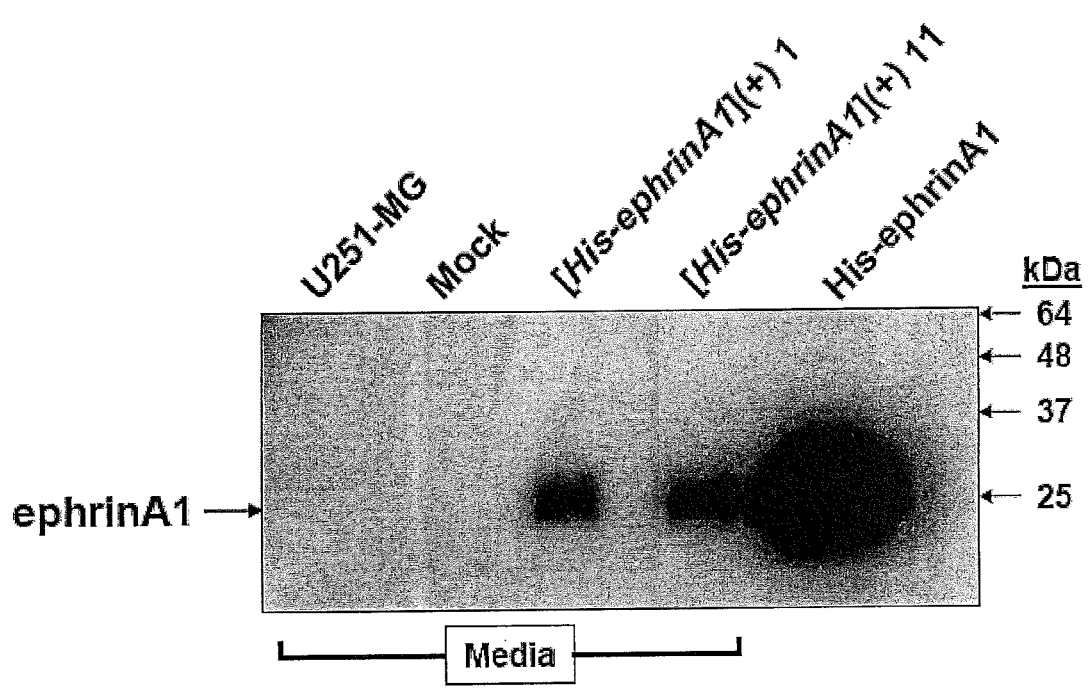

Strikingly, both dimeric and monomeric ephrinA1-Fc were capable of activating the receptor, as revealed by the presence of the immunoreactive band corresponding to phosphorylated EphA2 (FIG. 6D). The duration of EphA2 phosphorylation in response to treatment with the ephrinA1-Fc monomer was even longer than with the dimer. Phosphorylation of EphA2 was specifically mediated by ephrinA1-Fc and not affected by treatment with reducing agent and IA, or reduced and non-reduced IgG. Furthermore, treatment of U-251 MG cells with both dimeric and monomeric ephrinA1-Fc, and not IgG or PBS, resulted in significant cell rounding and loss of polarity (FIG. 6E).

A. Anchorage-independent growth assay. $2 \times 10^3$ cells were plated in 6-well dishes in growth medium plus 0.35% Agar (Difco), on a base layer of growth medium plus 0.5% Agar. Cells were supplemented with 1.0 µg/mL ephrinA1-Fc. ephrinA1-Fc was replenished and cells supplemented with fresh media 3 days after plating, and colonies were counted and photographed at low power after 14 days. Clusters of colonies greater than ~50 cells were counted in ten random fields at low power; each experimental condition or cell line was assayed in triplicate.

Figure 6F:
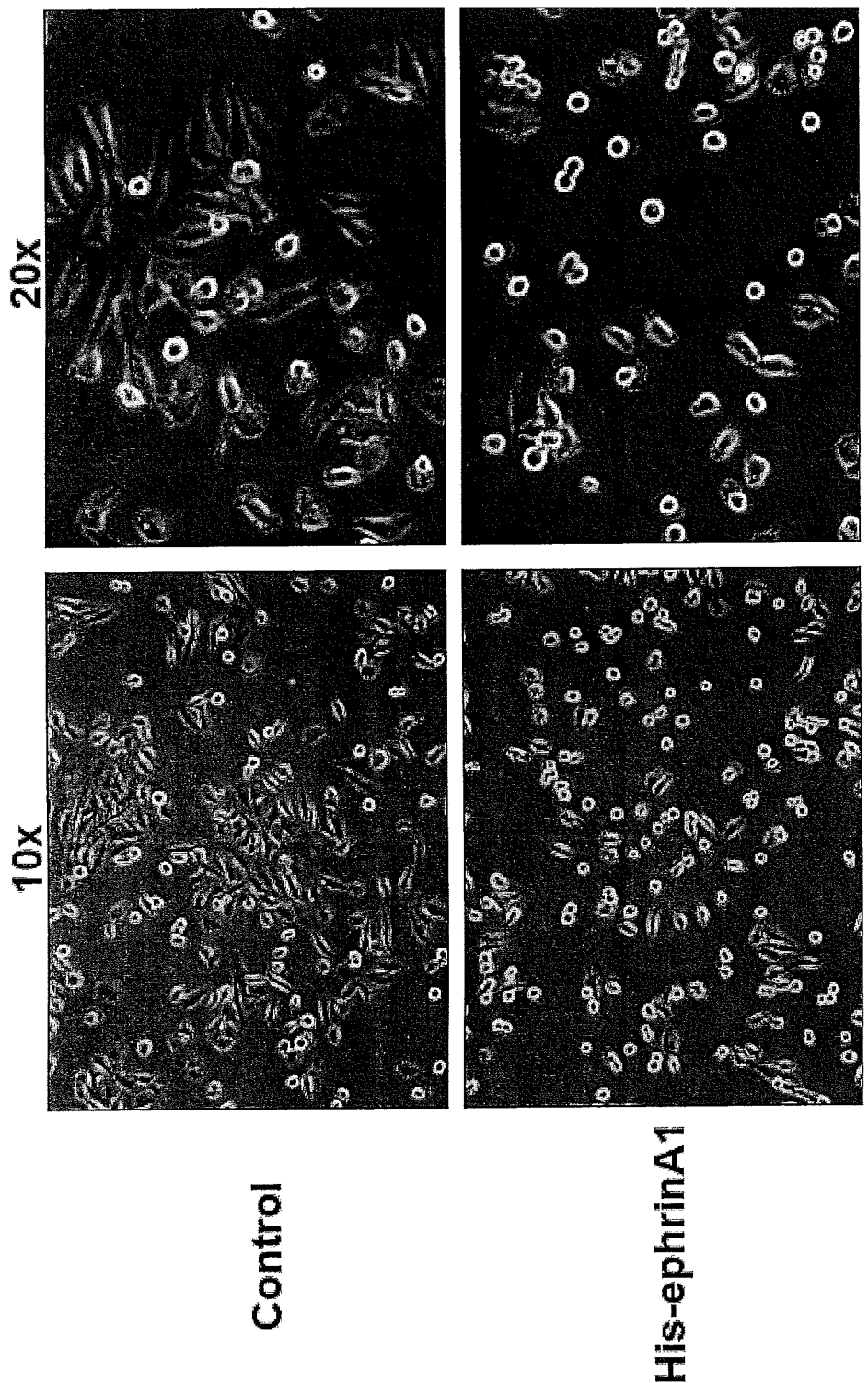

B. Migration assay. Further supporting the function of a monomer of ephrinA1, both monomeric and dimeric ephrinA1-Fc were very effective in inhibiting the migration of U-251 MG in a wound closure assay ($p<0.001$ vs. IgG-treated control) (FIG. 6F). U-251 MG cells were seeded onto 6-well dishes and allowed to grow until ~95% confluent. Wounds were made with a sterile 200 µL tip, cells were washed with PBS, and growth media containing monomeric or dimeric ephrinA1-Fc (1 µg/mL) was added. Phase contrast-microscopy pictures were taken of the same field at 0 hr and 24 hr following addition of treatment. ImagePro Plus software was used to analyze images. Distance of the wound in µM was measured in three places for each wound at each time point, and the percent wound closure over 24 hr was calculated for graphical representation. Thus, a monomer of ephrinA1-Fc has a similar potency to the homodimer in activating EphA2 in GBM cells.

C. Axonal Growth Cone Collapse. To investigate the possibility that a monomer of ephrinA1 is functional in mediating normal physiological processes, the roles of monomeric and dimeric ephrinA1-Fc in axonal growth cone collapse were compared. Primary rat cortical neurons were treated with monomeric or dimeric ephrinA1-Fc and fluorescently stained for F-actin to visualize growth cone structures.

Primary neuronal cultures were prepared as previously described (Turner et al. (2002) Exp. Neurol. 178:21-32). Briefly, the cortical lobes of embryonic day 18 Sprague-Dawley rat embryos were dissected and cells plated at low density on coverslips coated with 20 µg/mL poly-D-lysine (Sigma) and grown for 24 hours. EphrinA1-Fc (1 and 5 µg/mL), PBS (equal volume to ephrinA1-Fc), or $IgG_1$ isotype control (5 µg/mL) was added and cells incubated for 1 hour at 37° C. Cells were fixed, permeabilized, and stained with rhodamine-phalloidin (Invitrogen) for 20 min at room temperature, washed, and coverslips were mounted onto glass slides using Vectashield Hard Set mounting media containing DAPI (Vector Labs, Burlingame, Calif.). Images were acquired using an Olympus IX70 Inverted System Microscope (Olympus, Melville, N.Y.) and Hamamatsu digital camera (Hamamatsu City, Japan) with IPLab 3.6.4 software (Scanalytics, Inc, Fairfax Va.). Image-Pro Plus v.5.1 software was used for image analysis. Collapsed growth cones (CGC) were categorized as having a shrunken lamellipodia with no filopodia, and counts were normalized to the number of DAPI-stained nuclei in the same field by expressing data as a ratio of the number of collapsed growth cones/number of nuclei (CGC/DAPI). Mean CGC/DAPI ratio was determined for each treatment group.

Figure 7:
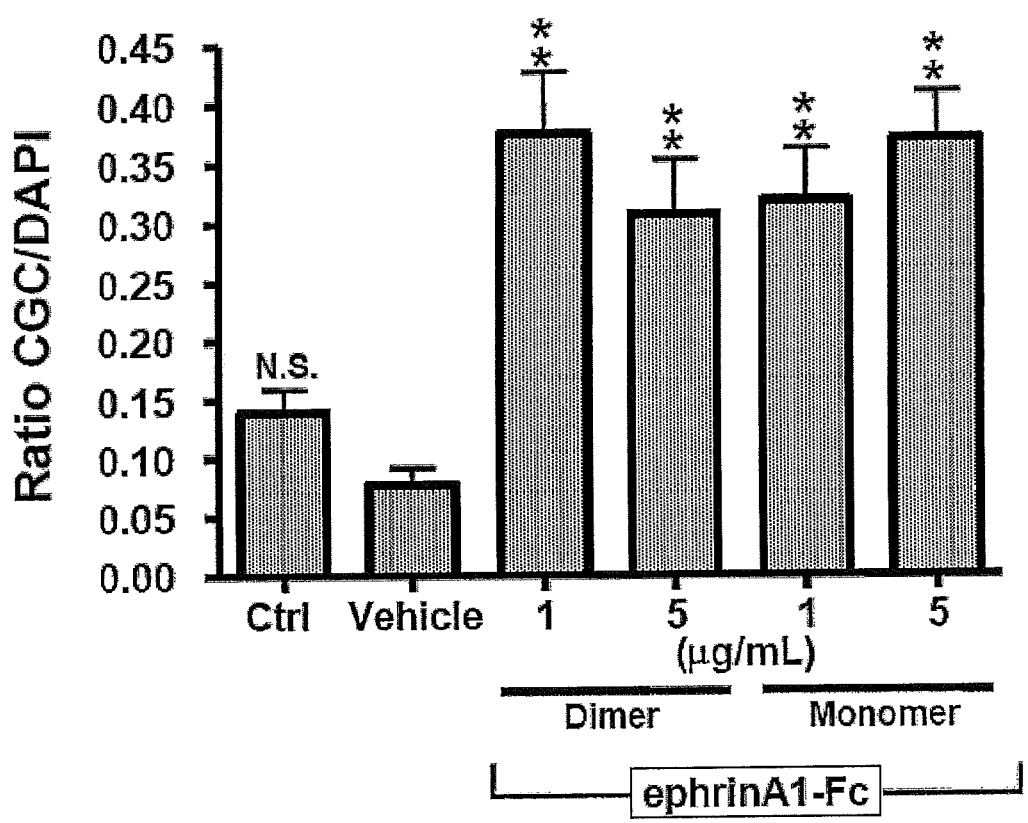
FIG. 7. Effect of monomeric and dimeric ephrinA1 on neuronal growth cones. Graphical representation of collapsed neuronal growth cones/total cell number (CGC/DAPI) for each treatment group. Primary rat cortical neurons were stained for F-actin following treatment for 1 hour with 1 μg/mL of a monomer or dimer of ephrinA1-Fc or an equal volume of PBS (vehicle). Nuclei were stained with DAPI. Control, non-treated cells. **, p<0.001 vs. vehicle; N.S., not statistically significant versus vehicle, p>0.05, Newman-Keuls Multiple Comparison Test.

Treatment with ephrinA1-Fc in both a monomeric and dimeric form for 1 hr resulted in a significant increase in collapsed axonal growth cones ($p<0.001$ versus vehicle-treated control) (FIG. 7). Treatment with 5 µg/mL of ligand did not lead to significantly more growth cone collapse, suggesting that a concentration of 1 µg/mL of ephrinA1-Fc represents saturating conditions. In sharp contrast to the distinct, collapsed growth cones of neurons treated with monomeric or dimeric ephrinA1-Fc, non-treated, vehicle-treated, or those neurons treated with IgG displayed well-developed, expanded growth cone structures and few, if any, collapsed growth cones (data not shown).

Example 4

Creation of ephrinA1-cytotoxin Constructs

Being that EphA2 is an internalized receptor that is over-expressed in GBM cells, we have produced a novel cytotoxin composed of ephrinA1, a ligand for EphA2, and a genetically modified bacterial toxin, *Pseudomonas* exotoxin A (PE38QQR).

EphrinA1-PE38QQR exhibited extremely potent and dose-dependent killing of GBM cells expressing EphA2, with an average $IC_{50}$ of $\sim 10^{-11}$ M using a cell viability assay. The cytotoxic effect of ephrinA1-PE38QQR was specific, since it was completely neutralized by an excess of ephrinA1 ligand. Cells that do not over-express EphA2, including normal human endothelial cells and GBM cells with down-regulated EphA2, were not responsive to the cytotoxin. Notably, ephrinA1-PE38QQR was also effective against breast and prostate cancer cells that over-express the EphA2 receptor.

To further validate the potential usefulness of EphA2-targeted therapies such as ephrinA1-PE38QQR, the presence and localization of EphA2 in GBM was explored by performing immunohistochemistry (IH) on tissue microarrays containing various grades of astrocytomas and normal. It was found that the level of EphA2 expression is significantly elevated in GBM versus lower-grade astrocytomas and normal brain ($p=0.001$ GBM vs. normal brain, $p=0.01$ GBM vs. grade II or grade III). EphA2 is localized specifically on the surface of GBM cells, both in established cell lines and in situ, as revealed by flow cytometry, confocal microscopy, and IH. Importantly, EphA2 is absent in normal brain.

Next, the cDNA encoding for a DT toxin, DT390, connected to ephrinA1 was cloned. The protein DT390-ephrinA1 begins with the DT sequence at the N-terminal end of the fusion protein. The N-terminal end of ephrinA1 is linked to the toxin, and the C-terminal end of the construct is a free C-terminal end of ephrinA1. Constructs encoding ephrinA1-PE4E were also cloned.

Figure 8A:
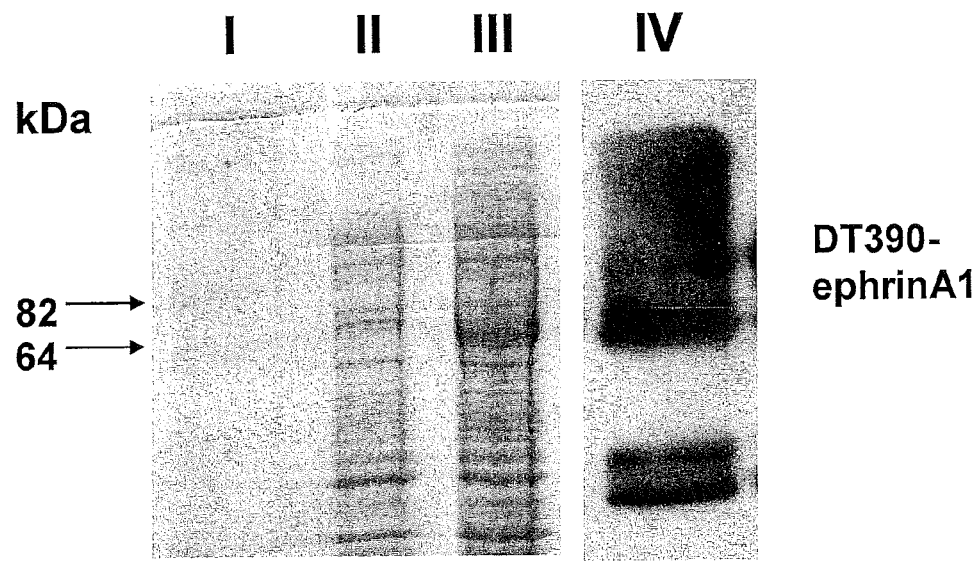
FIG. 8A-8B. DT390-ephrinA1 recombinant protein expression in *E. coli* and partial purification.
Figure 8B:
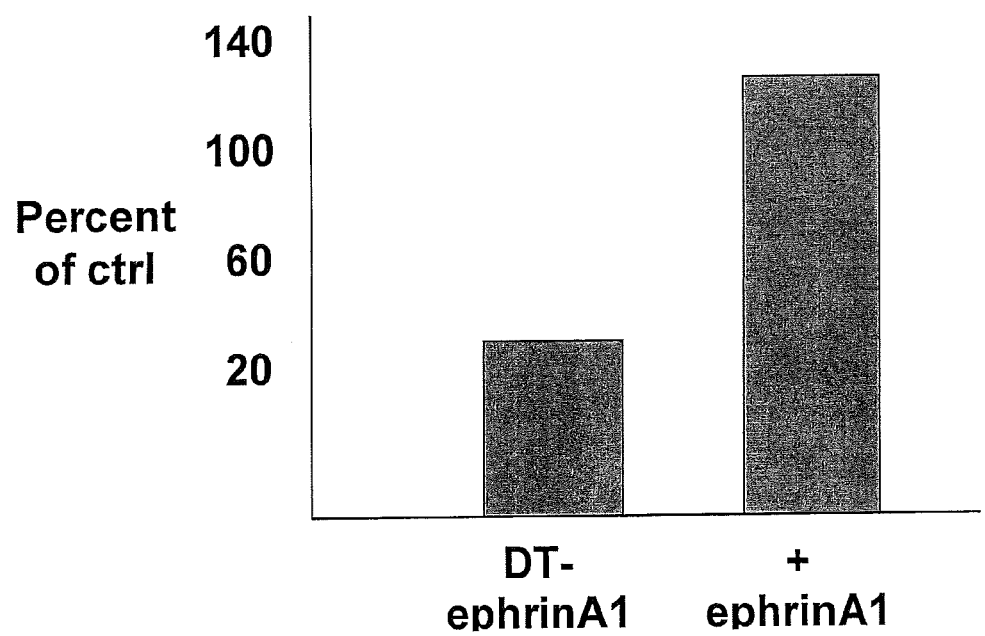

All three cytotoxin constructs were expressed in *E. coli*, with ephrinA1 and DT390-ephrinA1 demonstrating the best expression levels thus far (FIGS. 8A-8B). Therefore, a larger scale culture of bacteria transformed with the DT390-ephrinA1 was grown, the expressed protein being localized to the inclusion bodies. Upon isolating the inclusion bodies, the protein was denatured and renatured, then purified using FPLC (FIG. 8A).

The partially purified fractions of DT390-ephrinA1 were tested in a cell proliferation assay using the U-251 MG GBM cells. Surprisingly, at 15 nM concentration, the cytotoxin construct started to kill cancer cells. In order to document the specificity of the killing, the cells were pre-treated with commercially available ephrinA1-IgG recombinant protein. Pre-treatment protected cancer cells against the cytotoxic action of DT390-ephrinA1 (FIG. 8B).

Based on previous information that ephrinA1 monomer is potentially a much weaker ligand than its dimer, and that the EphA2 dimerization is needed for receptor internalization, the cytotoxic activity of DT390-ephrinA1 was wholly unexpected. It is noteworthy that ephrinA1 is placed at the N-terminal end of the ephrinA1-IgG construct, whereas ephrinA1 resides at the C-terminal end of the DT390-ephrinA1 construct. As such, it is likely that either the N- or C-terminal end of ephrinA1 can be linked to other recombinant proteins, a property that has been found attributable to IL-13 as a receptor ligand as well.

Example 5

Transient Silencing of EphA2 and/or ephrinA1 with siRNA

A new technology has been developed in which mammalian genes can be knocked down by transient transfection with silencing RNA duplexes (siRNA). This methodology was previously employed to successfully silence an AP-1 transcription factor, Fra-1, a factor discovered to be highly up-regulated in GBM (Debinski et al. (2001) Mol Med 7:598-608). In that vein, a siRNA duplex was designed to target human EphA2:

```
sense
                                    (SEQ ID NO: 21)
5' UGAAUGACAUGCCGAUCUA 3'
and anti-sense
                                    (SEQ ID NO: 22)
5' UAGAUCGGCAUGUCAUUCA 3'.
```

This sequence was BLAST-searched against expressed sequence tag libraries to ensure the specificity of the siRNA molecule. Desalted and deprotected synthetic oligonucleotides were made by Dharmacon (LaFayette, Colo.). The annealing of oligonucleotides is performed in 100 mM potassium acetate, 30 mM HEPES-KOH, pH 7.4, 2 mM magnesium acetate for 1 min. at 90° C., followed by 1 hr at 37° C. Control duplex oligonucleotides correspond to the inverse sequence or an siRNA scramble duplex.

siRNAs are transfected using the OligofectAMINE reagent (Invitrogen Life technologies). Transient transfections are carried out on 40-50% confluent cells plated one day before the experiment with 10% FBS without antibiotics using the siRNA ephA2 duplex and corresponding controls, in at least duplicates. For one well of a 24-well plate, 0.84 μg siRNA duplex is used. The effect of silencing is assayed 2, 3, 5 and 7 days after transfection. It has been observed that the silencing using siRNAs lasts between 6 and 10 generation times. The transfection efficiency will be evaluated by western blotting of EphA2 and general cell morphology, and compared to stably transfected and control cell lines.

Figure 9:
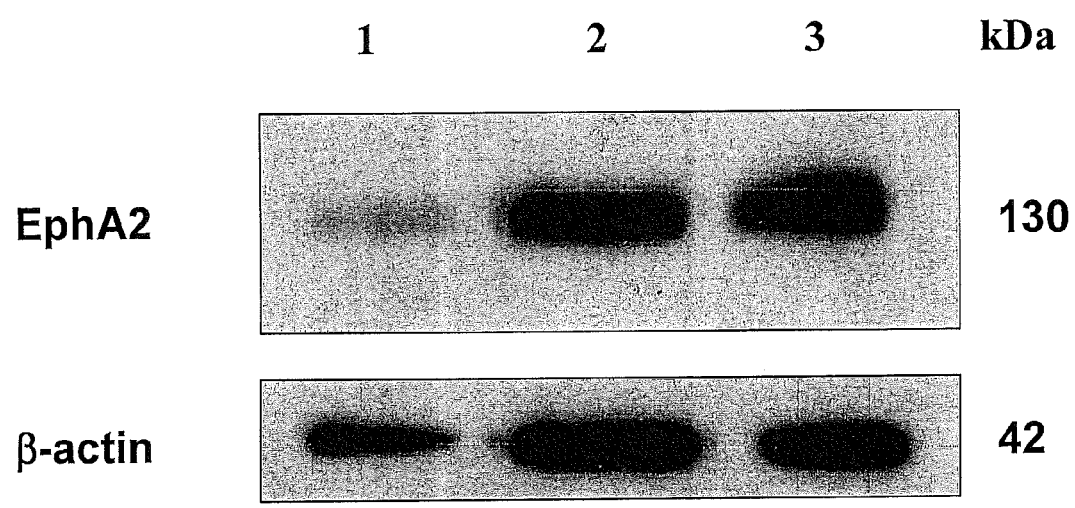
FIG. 9. Transient silencing of EphA2 with siRNA. Western blot of EphA2 in U-251 MG cells treated with ephA2 siRNA (1), nonsense siRNA (2), and sham-treated (3).

Experiments were performed in order to verify the silencing of EphA2 in U-251 MG GBM cells and found at least 50% decrease in immunoreactive EphA2 when standardized versus actin control (FIG. 9). In addition, the use of these siRNA resulted in a similar degree of EphA2 decrease in cells, producing a prominent anti-tumor effect in vivo, and thus represents a molecular candidate drug in tumors overexpressing EphA2, such as ovarian carcinoma and pancreatic adenocarcinoma (Landen et al. (2005) Cancer Res 65:6910-6818; Duxbury et al. (2004) Oncogene 23:1448-1456).

Example 6

Molecular Targeting of EphA2 and IL-13Rα2 to Xenografts

Three types of human xenografts of non-established GBM cells were obtained that can be implanted into immunocompromised animals. These three types of human GBM explants were characterized for EGFR expression: Mayo-GBM-5 does not demonstrate EGFR amplification, Mayo-GBM-6 has the EGFRvIII mutant amplified, and Mayo-GBM-12 has the wild type EGFR amplified (Pandita et al. (2004) Genes Chromosomes Cancer 39:29-36). These explants produce intracranial tumors of infiltrative character, a trait not seen with the majority of established human GBM cell lines (Pandita et al. (2004) Genes Chromosomes Cancer 39:29-36).

Mayo-GBM-6 and Mayo-GBM-5 cells were found to be highly responsive to an IL-13-based cytotoxin, IL13.E13K-PE38QQR. In fact, they appear to be more susceptible to the cytotoxin than the U-251 MG cells considered to be high-responders to the IL-13 cytotoxins (e.g., Debinski et al. (1999) Clin Cancer Res 5:985-990). The $IC_{50}$ in Mayo-GBM6 and MayoGBM5 cells is 0.3 ng/mL and 0.2 ng/mL, respectively, while in U-251 MG cells it was 0.8 to 1.5 ng/mL in two independent assays. Thus, these explants are several times more responsive towards the cytotoxin than the established GBM cells, which is indicative of a high level of expression of IL-13Rα2. Interestingly, these cells also over-express EphA2 and are suitable for in vivo targeted anti-EphA2 therapies.

This is the first attempt to create a cytotoxic therapy based on any of the ephrin ligands of either class (A or B). EphrinA1-PE38QQR is potent and specific, and forms the basis for the further clinical development of ephrinA1-based cytotoxins that can also be used in combination with IL-13Rα2-directed and Fra-1-directed therapies to improve the outcome of patients with GBM and other EphA2-expressing tumors.

Example 7

IL-13Rα2, Epha2, and Fra-1 Expression

To investigate the expression of IL-13Rα2, EphA2, and Fra-1 in astrocytomas, immunohistochemistry (IH) for each of these three proteins was performed using commercially available tissue microarrays containing pathologically-verified tumor tissue from 16 patients with WHO grade II, or low-grade, astrocytoma (A), 14 with WHO grade III, or anaplastic, astrocytoma (AA), and 46 with WHO grade IV GBM, in addition to 9 normal brain tissue samples. Specific staining for each protein was blindly scored first with respect to the percentage of positively stained tumor cells per tissue section. Table 1 displays the number and percentage of patients within each histological sub-type having a frequency of 0-10%, 10-50%, or 50-100% of tumor cells per section stained positive for IL-13Rα2, EphA2, and Fra-1.

TABLE 1

| | 0-10% [%] | 10-50% [%] | 50-100% [%] | Total |
|---|---|---|---|---|
| IL-13Rα2 | | | | |
| Normal Brain | 6 [75] | 1 [13] | 1 [13] | 8 |
| A | 6 [38] | 6 [37] | 4 [25] | 16 |
| AA | 3 [21] | 6 [42] | 5 [36] | 14 |
| GBM | 5 [11] | 5 [11] | 36 [78] | 46 |
| EphA2 | | | | |
| Normal Brain | 7 [78] | 2 [22] | 0 [0] | 9 |
| A | 5 [31] | 5 [32] | 6 [38] | 16 |
| AA | 1 [8] | 5 [38] | 7 [54] | 13 |
| GBM | 1 [2] | 3 [7] | 42 [91] | 46 |
| Fra-1 | | | | |
| Normal Brain | 6 [67] | 2 [22] | 1 [11] | 9 |
| A | 6 [38] | 5 [31] | 5 [31] | 16 |
| AA | 8 [57] | 2 [14] | 4 [29] | 14 |
| GBM | 7 [15] | 65 [13] | 33 [72] | 46 |

A, low grade astrocytoma; AA, anaplastic astrocytoma; GBM, glioblastoma. Number in brackets corresponds to percent of samples positive within each histological subtype.

Figure 10A:
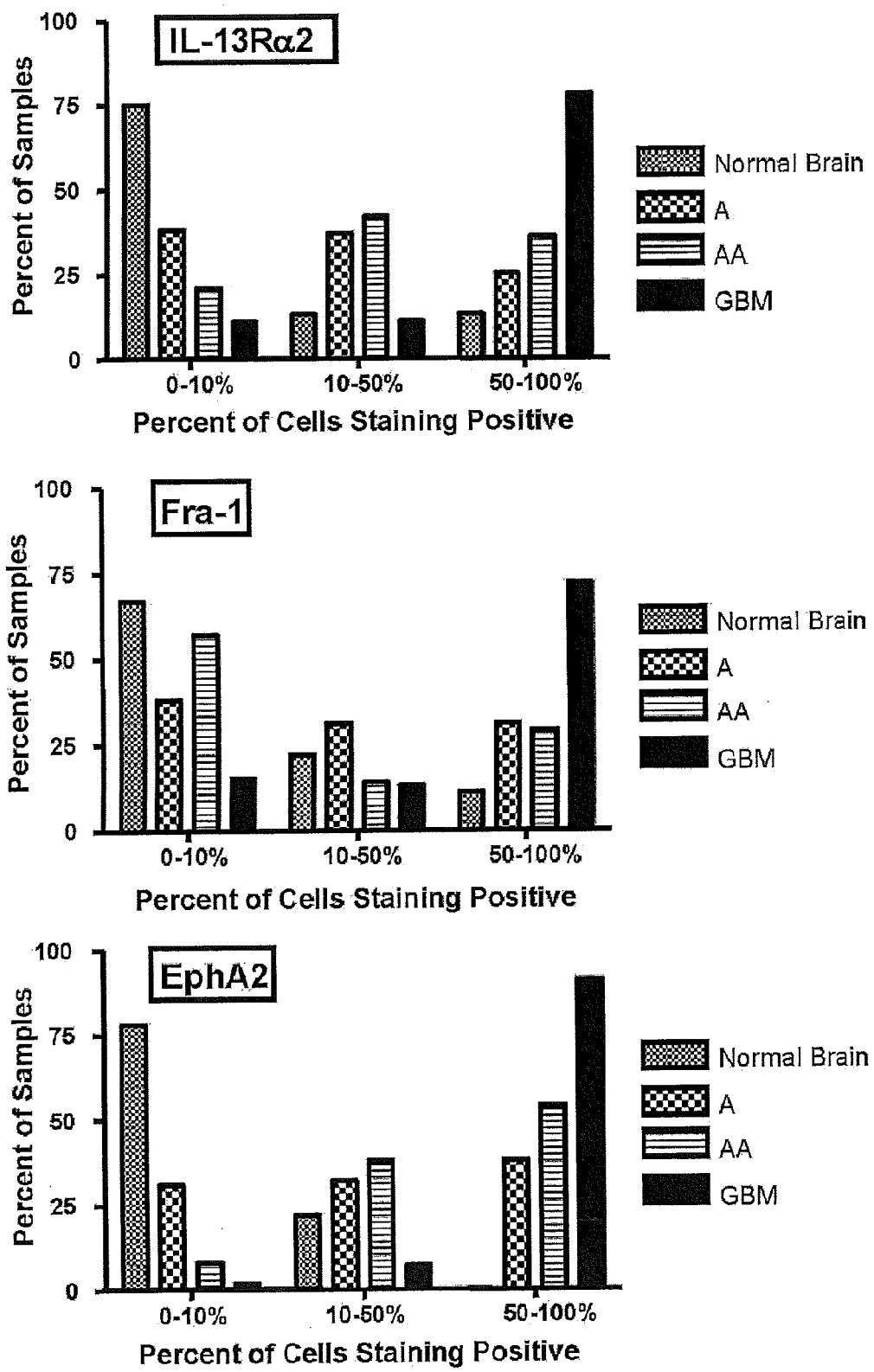
FIG. 10A-10D shows the analysis of IL-13Rα2, EphA2, and Fra-1 expression in astrocytomas and normal brain.

When considering frequency, those specimens with the most tumor cells stained positive (50-100%) were GBM, with 78, 91, and 72% of GBM specimens falling into this group for IL-13Rα2, EphA2, and Fra-1, respectively (Table 1, FIG. 10A). Those tumors with a frequency of 0-10% and 10-50% of positive-staining cells were more commonly low-grade and anaplastic astrocytomas rather than GBM (Table 1, FIG. 10A). Importantly, the majority of normal brain specimens fell into the 0-10% frequency category for all three markers (Table 1, FIG. 10A). Together, these findings indicate that the frequency of expression of IL-13Rα2, EphA2, and Fra-1 within a tumor is likely associated with astrocytoma grade.

A similar pattern was observed with respect to intensity of IL-13Rα2, EphA2, and Fra-1 staining Each specimen was assigned a numerical score based on the overall specific staining intensity of each marker: 0, none; 1, weak; 2, moderate; 3, strong. The staining intensity with respect to the percent of samples in each staining category for normal brain, low-grade astrocytoma, anaplastic astrocytoma, and GBM for each marker is depicted in Table 2 and FIG. 10B.

TABLE 2

| | None [%] | Weak [%] | Moderate [%] | Strong [%] | Total |
|---|---|---|---|---|---|
| IL-13Rα2 | | | | | |
| Normal Brain | 3 [38] | 4 [50] | 1 [13] | 0 [0] | 9 |
| A | 5 [31] | 4 [25] | 5 [31] | 2 [13] | 16 |
| AA | 2 [14] | 4 [29] | 7 [50] | 1 [7] | 13 |
| GBM | 3 [7] | 8 [17] | 21 [46] | 14 [30] | 46 |
| EphA2 | | | | | |
| Normal Brain | 3 [33] | 4 [44] | 2 [22] | 0 [0] | 9 |
| A | 2 [13] | 4 [25] | 5 [31] | 5 [31] | 16 |
| AA | 0 [0] | 4 [31] | 7 [54] | 2 [15] | 13 |
| GBM | 0 [0] | 1 [2] | 17 [37] | 28 [61] | 46 |
| Fra-1 | | | | | |
| Normal Brain | 2 [22] | 3 [33] | 4 [44] | 0 [0] | 9 |
| A | 3 [19] | 5 [31] | 6 [38] | 2 [13] | 16 |
| AA | 3 [21] | 5 [3] | 5 [36] | 1 [7] | 14 |
| GBM | 4 [9] | 3 [7] | 16 [35] | 23 [50] | 46 |

Number in brackets corresponds to percent of samples positive within each histological subtype.

Figure 10B:
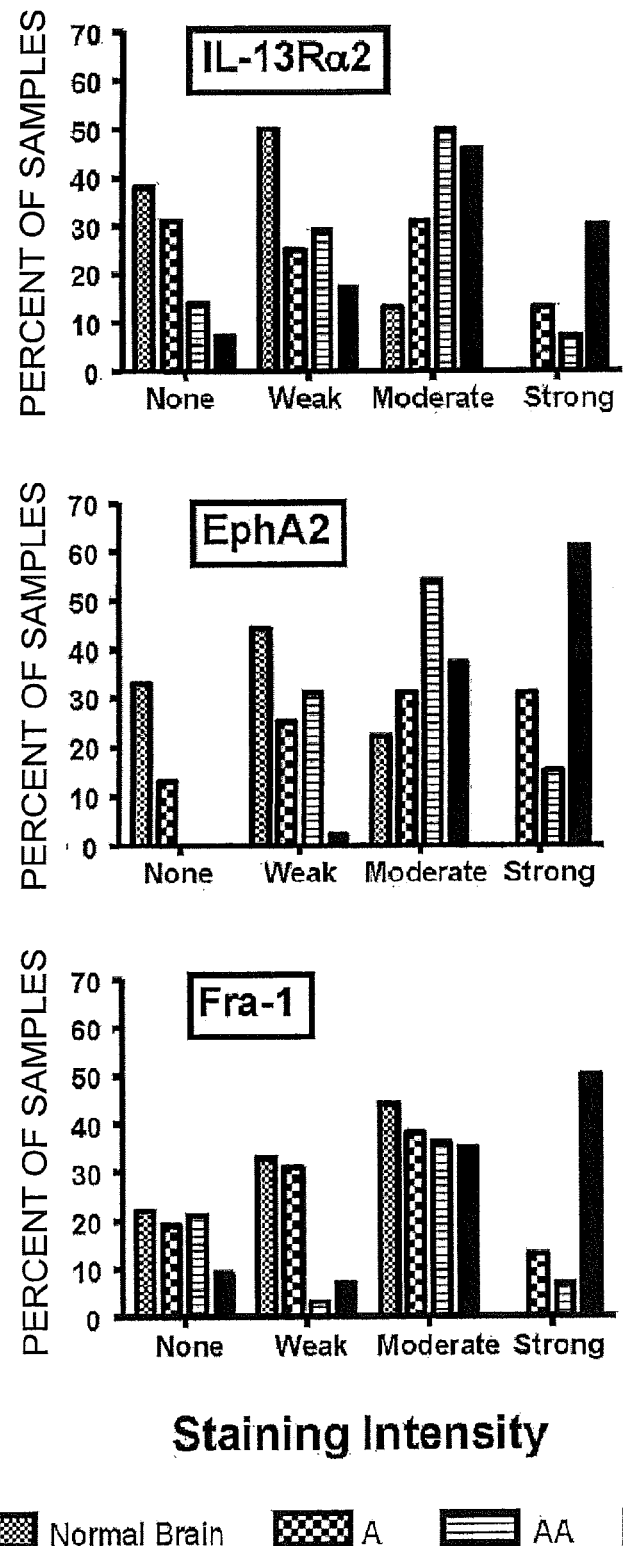
Figure 10C:
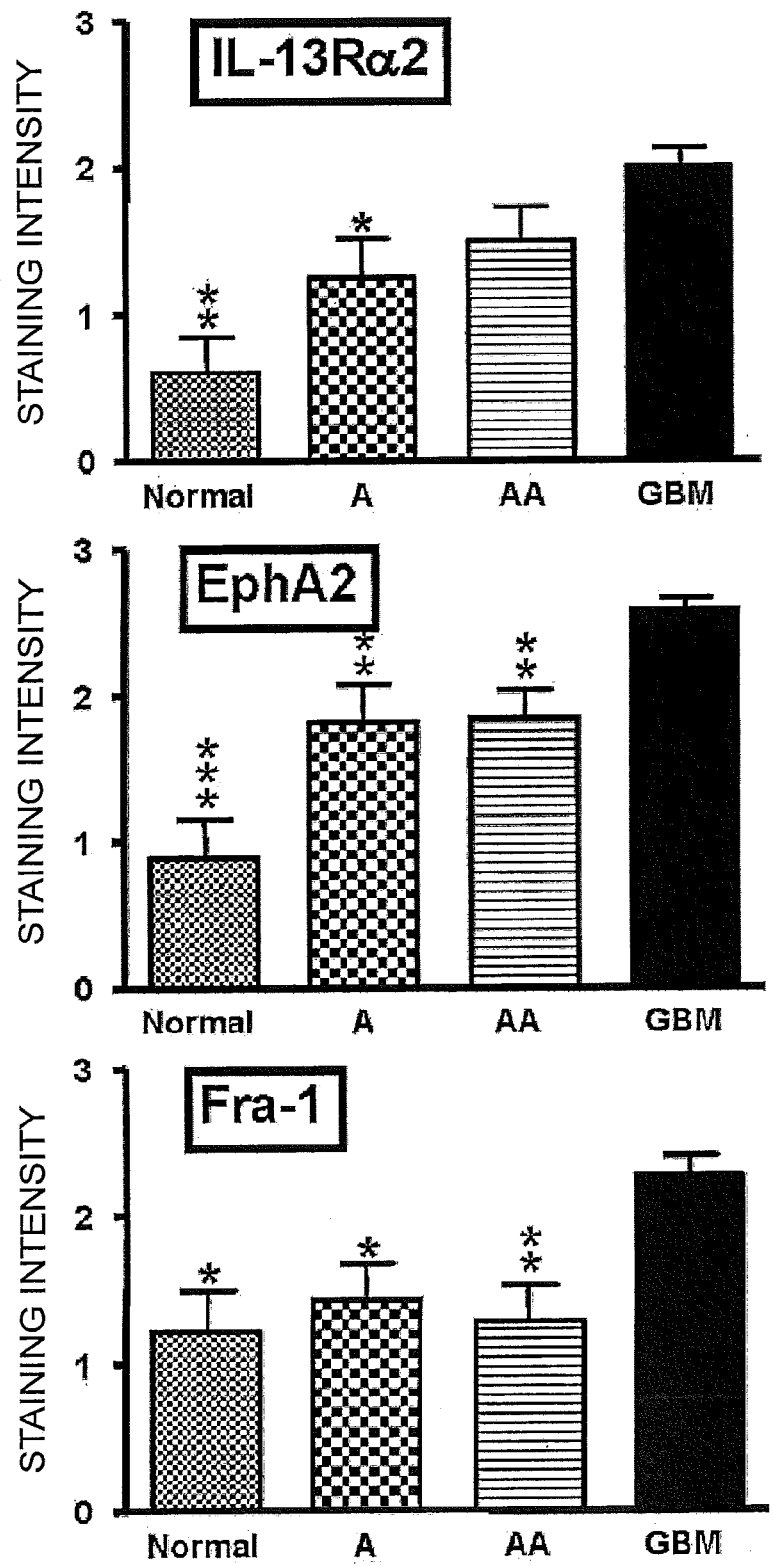
Figure 10D:
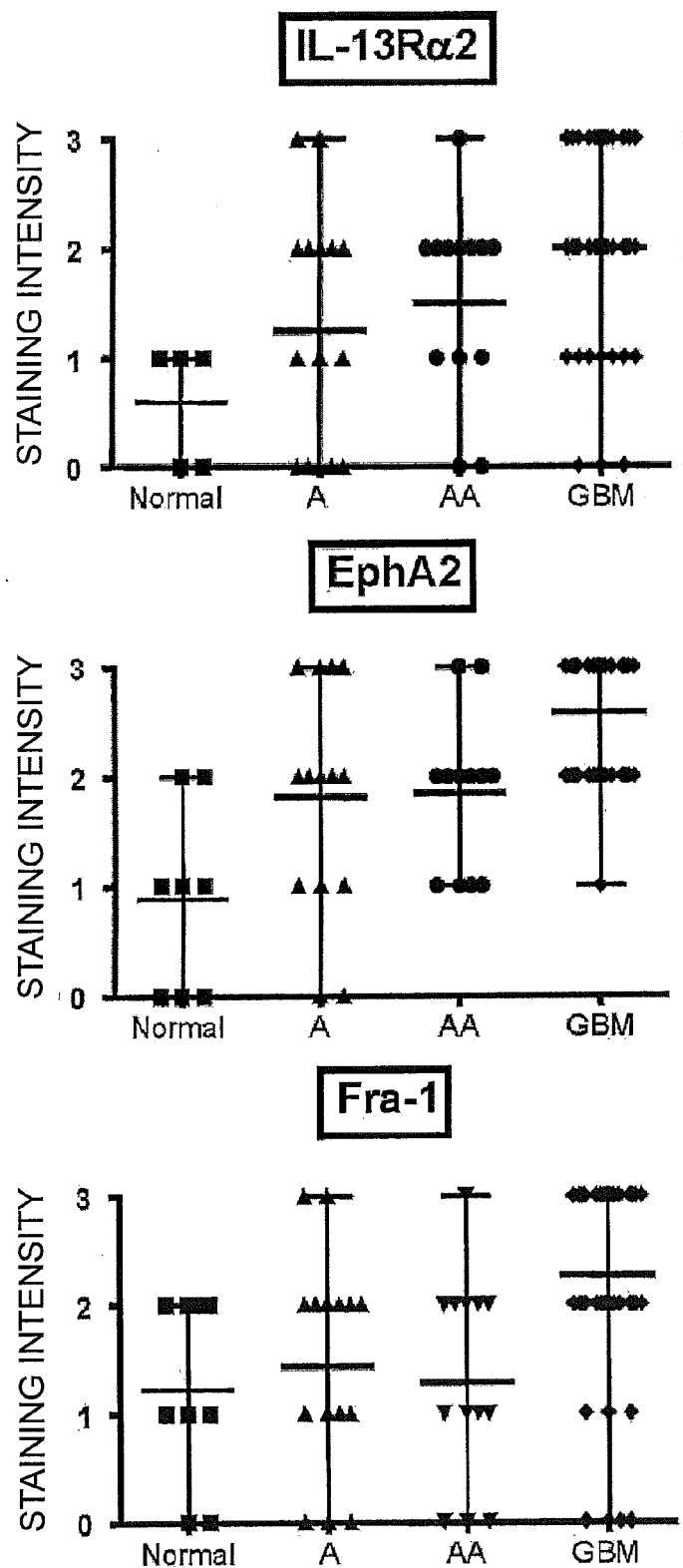
Figure 11A:
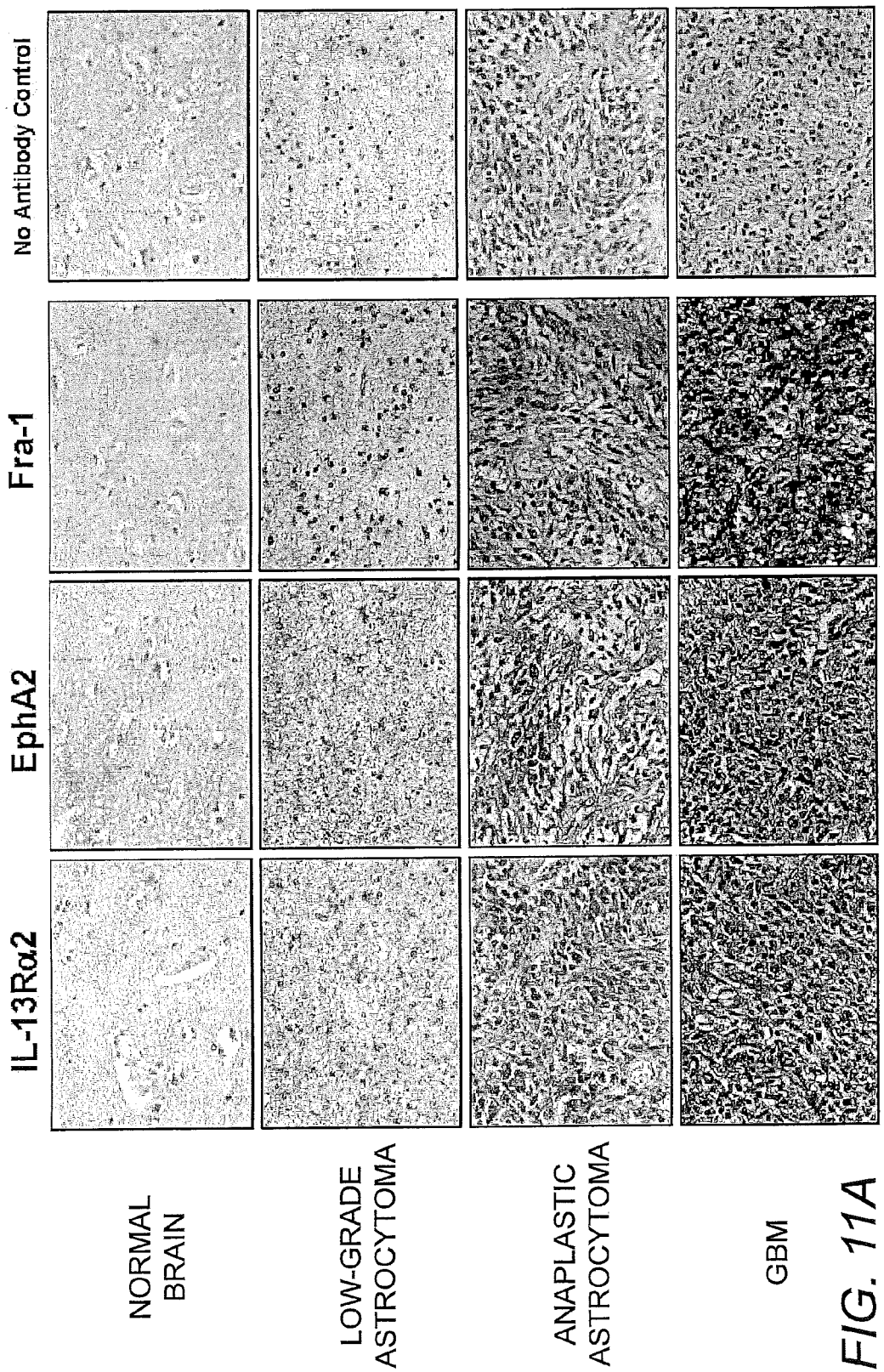
FIG. 11A-11D shows immunohistochemistry and western blot analysis of IL-13Rα2, EphA2, and Fra-1 expression in astrocytomas, normal brain, and human GBM xenograft tumors.

GBM included 30, 61, and 50% of samples with strong staining (intensity 3) for IL-13Rα2, EphA2, and Fra-1, respectively (Table 2, FIG. 10B). In contrast, normal brain never stained strongly for any of the three factors (Table 2, FIG. 10B). IL-13Rα2, EphA2, and Fra-1 staining intensity was significantly higher in GBM when compared to normal brain (p<0.01, IL-13Rα2; p<0.001, EphA2; p<0.05, Fra-1) (FIG. 10C). Moreover, all three factors were expressed at a significantly higher level in GBM than low-grade astrocytomas (p<0.05, IL-13Rα2; p<0.01, EphA2; p<0.05, Fra-1), and EphA2 and Fra-1 were more prevalent in GBM than anaplastic astrocytomas (p<0.01, EphA2; p<0.01, Fra-1) (FIG. 10C). Overall, the intensity of expression of all three markers increased with astrocytoma grade from normal brain to GBM (FIG. 10B,C,D). The intensity of IL-13Rα2, EphA2, and Fra1 for each individual patient specimen is shown in FIG. 10D, further representing a pattern indicative of the involvement of all three factors in astrocytoma formation/progression. This increase in expression of IL-13Rα2, EphA2, and Fra-1 as related to tumor grade is shown in representative sections of normal brain, low-grade astrocytoma, anaplastic astrocytoma, and GBM (FIG. 11A).

Example 8

Combined Expression of Epha2, IL-13Rα2, and Fra-1 in GBM

Figure 11B:
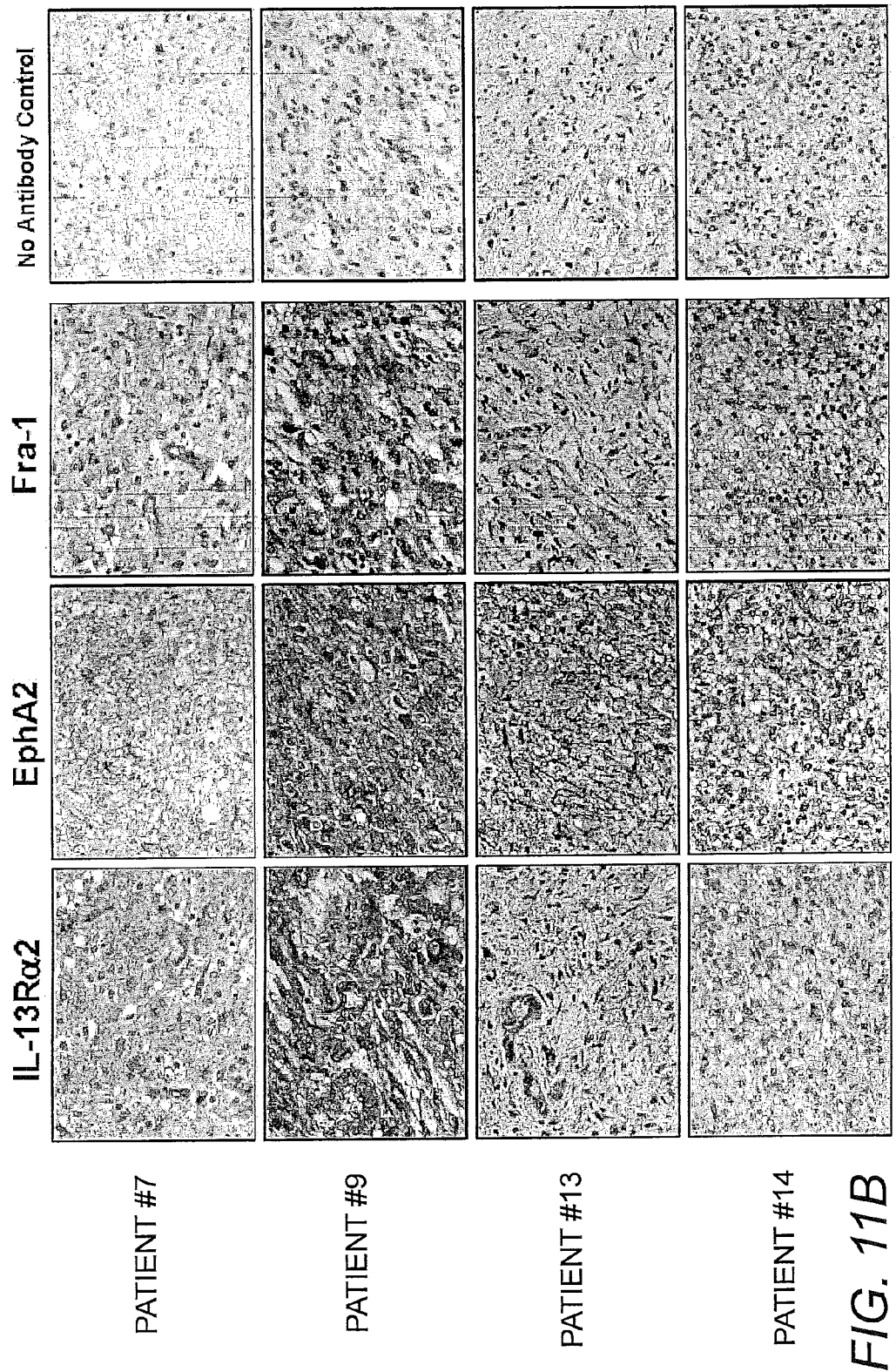

Despite the finding that IL-13Rα2, EphA2, and Fra-1 individually are over-expressed in a majority of GBM tumors when compared to low-grade and anaplastic astrocytomas and normal brain, none of these markers were strongly over-expressed in 100% of GBM cases, and some were expressed in less than 50% of cells within a given tumor (Tables 1 and 2, FIGS. 10A-10D). An expression profile for IL-13Rα2, EphA2, and Fra-1 for a representative 16 of the GBM samples analyzed depicts both the staining intensity score for each tumor as well as the frequency of positive-staining tumor cells (Table 3). This data revealed that 4/16(25%) of GBM patients had tumors that strongly over-expressed all three factors (staining intensity score of 3), albeit at variable frequencies of positive-staining tumor cells/specimen (Table 3). The remaining tumors either had low or moderate expression of one or more of the factors, such as in patient #7 for EphA2 (Table 3). It was evident, however, that at least one of the three markers was, in all cases, present at a level of intensity that we expect to be sufficient for effective therapeutic molecular targeting (moderate or strong staining intensity), and in a majority of tumor cells within the specimen (Table 3). The expression of all three proteins by immunohistochemistry is shown in patients #7, 9, 13, and 14 (FIG. 11B). Overall, 100% of GBM specimens over-expressed at least 1 of the 3 targets at a moderate or strong intensity.

Figure 11C:
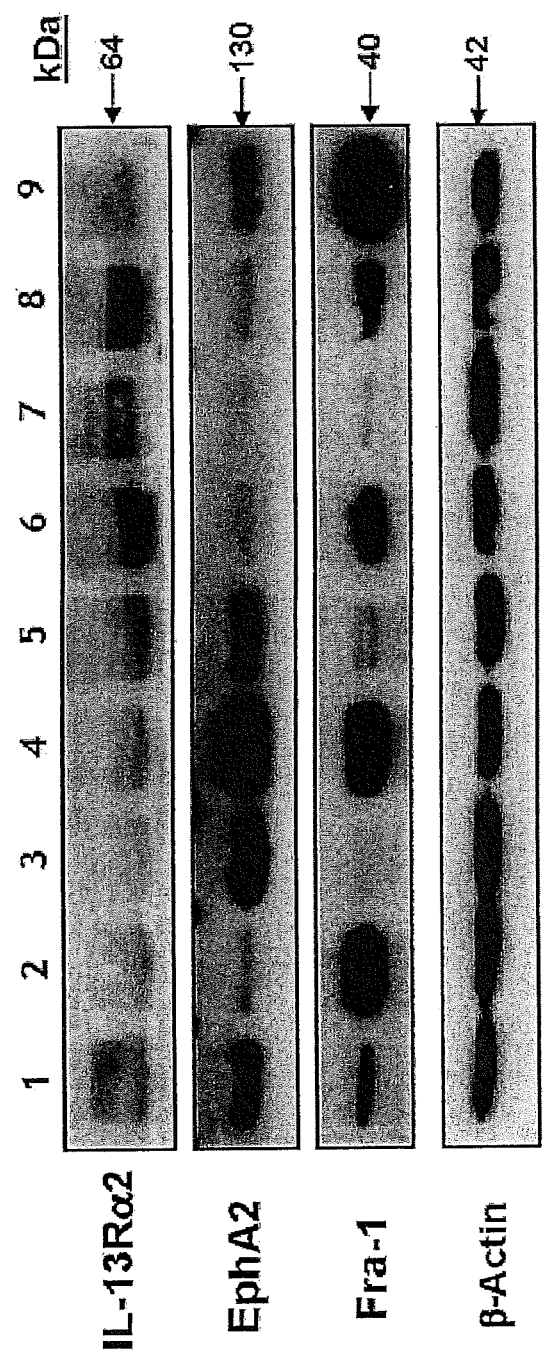

Western blot analysis of human GBM tumor tissue revealed results consistent with the immunohistochemical analysis. IL-13Rα2 was over-expressed in 5/9 specimens (FIG. 11C, #1, 5, 6, 7, 8), EphA2 in 5/9 (FIG. 11C, #1, 3, 4, 5, 9), and Fra-1 also in 5/9 (FIG. 11C, #2, 4, 6, 8, 9). Notably, those tumors which had low expression of one or more of the proteins, over-expressed at least one of the other two. For example, tumor #4 did not over-express IL-13Rα2, but displayed abundant EphA2 and Fra-1 (FIG. 11C). A similar pattern was observed for EphA2 in tumors #2, 6, and 8, and for Fra-1 in tumors #3 and 5 (FIG. 11C). Importantly, all GBM tumor specimens analyzed by western blot over-expressed at least one of the three proteins (FIG. 11C), further supporting the findings from IH analysis that the combined expression of IL-13Rα2, EphA2, and Fra-1 in GBM patient tumors is 100%. Moreover, these results indicate the need for a combinatorial targeted approach in order to attack tumors in all GBM patients.

TABLE 3

| Patient # | EphA2 | | IL-13Rα2 | | Fra-1 | |
|---|---|---|---|---|---|---|
| | Intensity | % Positive Cells | Intensity | % Positive Cells | Intensity | % Positive Cells |
| 1 | 3 | 50-100 | 3 | 50-100 | 3 | 10-50 |
| 2 | 3 | 50-100 | 2 | 50-100 | 2 | 10-50 |
| 3 | 3 | 50-100 | 2 | 50-100 | 3 | 50-100 |
| 4 | 3 | 50-100 | 3 | 50-100 | 2 | 10-50 |
| 5 | 3 | 50-100 | 2 | 10-50 | 2 | 10-50 |
| 6 | 2 | 50-100 | 3 | 50-100 | 2 | 0-10 |
| 7 | 1 | 0-10 | 2 | 50-100 | 3 | 10-50 |
| 8 | 3 | 50-100 | 3 | 50-100 | 3 | 50-100 |
| 9 | 3 | 50-100 | 3 | 50-100 | 3 | 50-100 |
| 10 | 2 | 10-50 | 3 | 50-100 | 2 | 50-100 |
| 11 | 2 | 50-100 | 3 | 50-100 | 3 | 50-100 |
| 12 | 2 | 50-100 | 2 | 50-100 | 2 | 50-100 |
| 13 | 3 | 50-100 | 2 | 10-50 | 0 | 0-10 |
| 14 | 2 | 50-100 | 2 | 0-10 | 2 | 50-100 |
| 15 | 2 | 50-100 | 3 | 50-100 | 3 | 50-100 |
| 16 | 3 | 50-100 | 3 | 50-100 | 3 | 50-100 |

Example 9

IL-13Rα2, Epha2, and Fra-1 Expression in Human GBM Tumor Cells

Figure 11D:
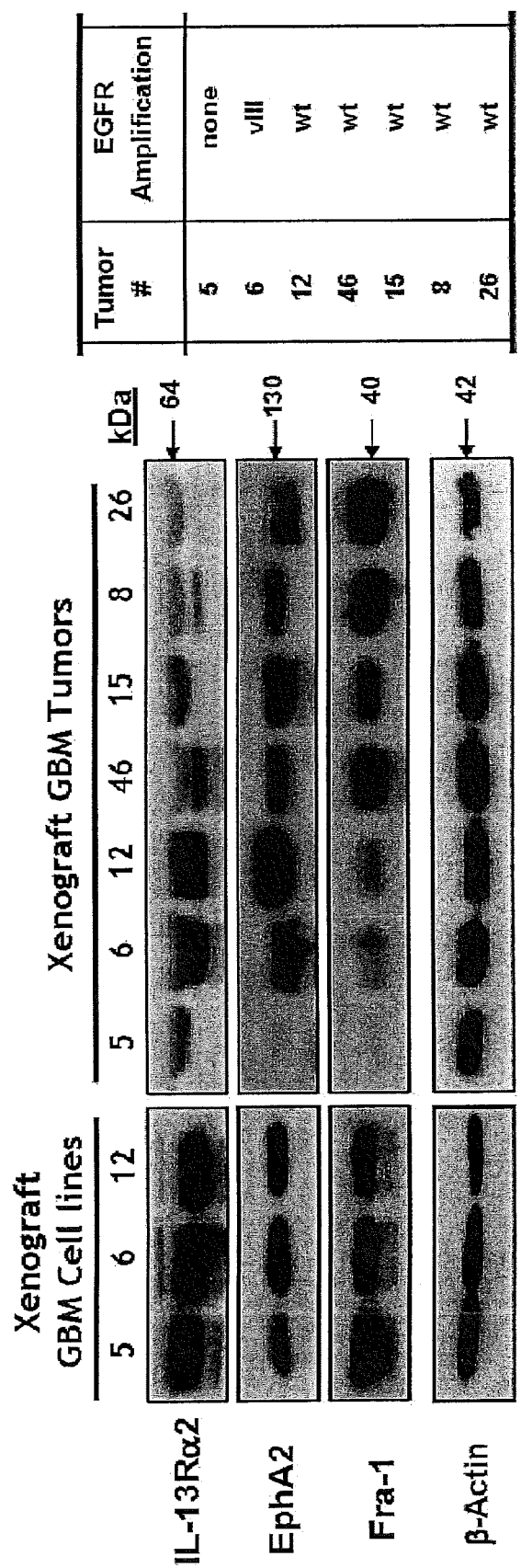

To further explore IL-13Rα2, EphA2, and Fra-1 expression in GBM, explanted human GBM tumors were analyzed which had been serially passaged in nude mice and established to resemble characteristics of the original tumor (Pandita et al. (2004) Genes Chromosomes Cancer 39:29-36; Sarkaria et al. (2006) Clin. Cancer Res. 12:2264-71). In addition, some of these tumors were cultured to obtain cell lines, and whole lysates from these cells were also used for the analysis. Western blot analysis revealed abundant expression of IL-13Rα2, EphA2, and Fra-1 in all three xenograft cell lines and a majority of the xenograft tumor specimens (FIG. 11D); all three cell lines were found previously to be highly susceptible to IL-13-based cytotoxins (data not shown). IL-13Rα2 was over-expressed in 5/7 tumors (FIG. 11D, #5, 6, 12, 46, and 15), EphA2 in 6/7 tumors (FIG. 11D, #6, 12, 46, 15, 8, and 26), and Fra-1 in 4/7 tumors (FIG. 11D, #46, 15, 8, and 26). Notably, every tumor displayed over-expression of at least one of the three proteins (FIG. 2D), supporting the immunohistochemical staining and results from western blot analysis of human GBM tumor tissue. Interestingly, the expression of all three factors varied somewhat when comparing tumor specimens and the corresponding established cell lines (FIG. 11D, xenograft cell lines and tumors #5, 6, and 12). These tumors have been previously characterized for EGFR amplification (FIGS. 11C and 11D; 5 out of 12 tumors analyzed had EGFR amplified and all of the EGFR-positive tumors were used in this assay), and it has been shown that the EGFR status of the tumors has a tendency to change upon establishment in culture (Pandita et al. (2004) Genes Chromosomes Cancer 39:29-36), which may also hold true for the markers of interest here. Interestingly, tumor #5, which has no EGFR amplification, has no detectable EphA2 or Fra-1. In contrast, EphA2 and Fra-1 are expressed in tumor #6, which has amplified EGFRvIII, and in tumors #12, 46, 15, 8, and 26, which over-express wild-type EGFR. Thus, this analysis reveals that EphA2 and Fra-1 expression correlates in general with the expression of EGFR in these tumors, in accordance with previous data revealing EphA2 and Fra-1 as part of a small group of genes whose expression is controlled by EGFRvIII (Ramnarain et al. (2006) Cancer Res. 66:867-74). However, they can also be over-expressed independently of EGFRs, indicative of other mechanisms involved in their upregulation (Ramnarain et al. (2006) Cancer Res. 66:867-74).

Example 10

IL-13Rα2 And Epha2-Targeted Cytotoxins Kill GBM Cells

Figure 12A:
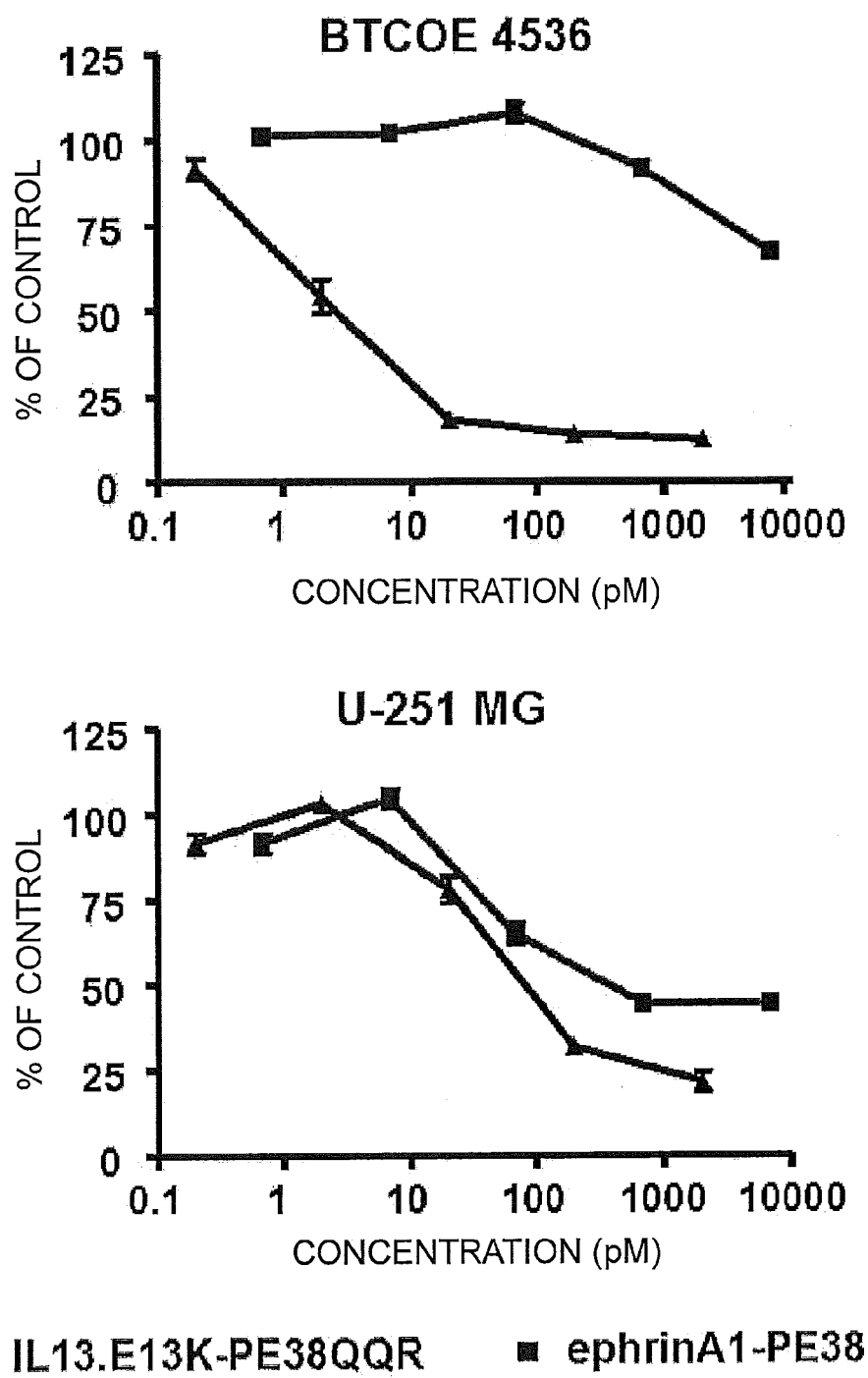
FIG. 12A-12C shows that human GBM cells are killed by IL-13Rα2- and EphA2-targeted cytotoxins.
Figure 12B:
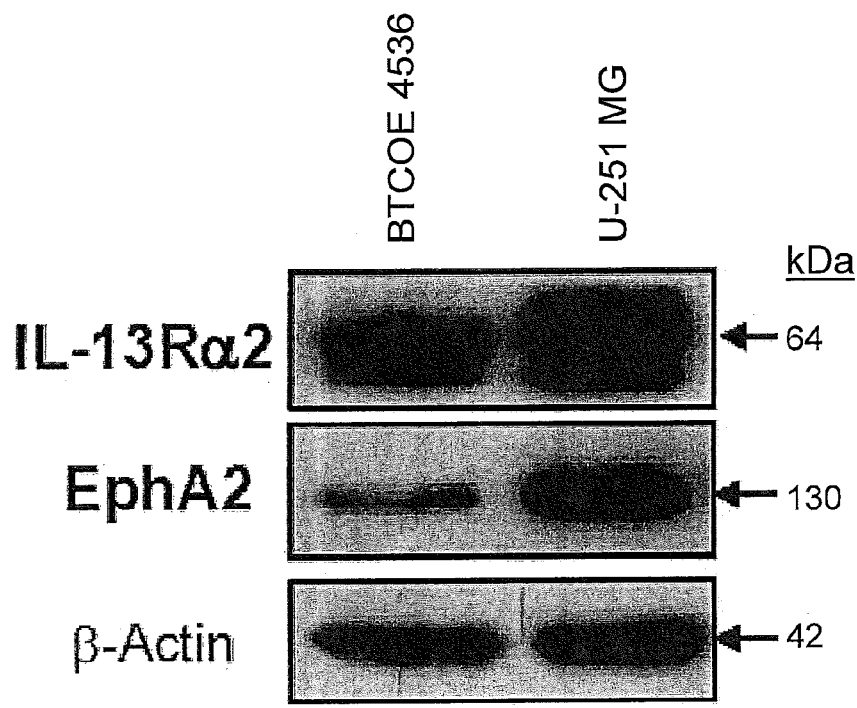
Figure 12C:
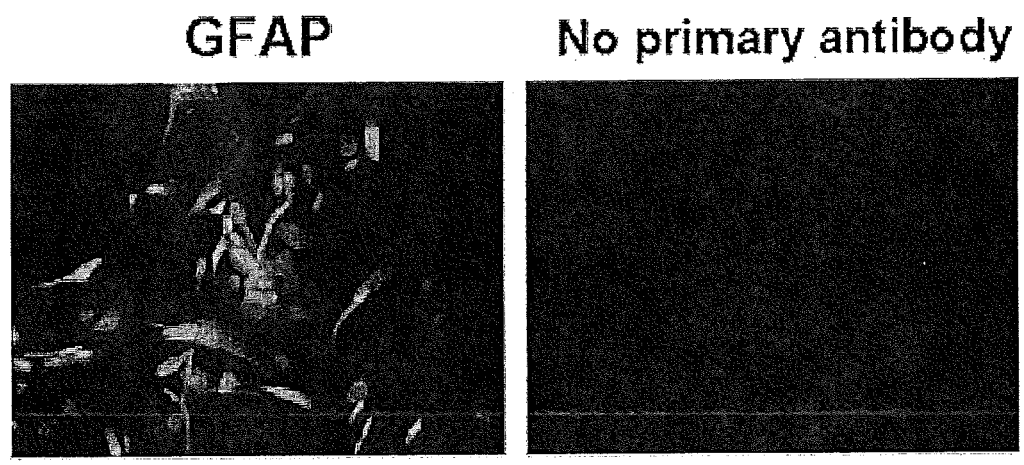

To confirm the utility of IL-13Rα2 and EphA2 as combinatorial molecular targets in GBM, tests were conducted to determine the ability of cytotoxins targeted to these plasma membrane receptors to kill primary cells cultured from fresh isolates of a pathologically-verified human GBM tumor specimen. IL-13.E13K.PE38QQR is a recombinant IL-13Rα2-targeted cytotoxin consisting of a mutated IL-13 ligand fused to PE38QQR, a derivative of *Pseudomonas* exotoxin A (Debinski et al. (1998) Nat. Biotechnol. 16:449-53). EphrinA1-PE38QQR is an EphA2-targeted cytotoxin consisting of the ephrinA1 ligand chemically conjugated to PE38QQR. Both cytotoxins have been found to have potent and specific killing activity against established GBM cell lines in culture (Debinski et al. (1998) Nat. Biotechnol. 16:449-53). It was found that tumor cells derived from BTCOE 4536, a GBM tumor, are killed by IL-13.E13K.PE38QQR and, to a much lesser extent, ephrinA1-PE38QQR (FIG. 12A). Accordingly, western blot analysis demonstrated that these cells highly over-expressed IL-13Rα2, and did not over-express EphA2 (FIG. 12B). The cells derived from BTCOE 4536 are, indeed, of astrocytic origin, as they expressed the astrocyte marker GFAP (FIG.

12C). Moreover, established human GBM cells were susceptible to killing with the targeted cytotoxins in accordance with their level of target protein expression. U-251 MG cells over-express both IL-13Rα2 and EphA2 to a similar degree (FIG. 12B), and were thus potently killed by both IL-13.E13K.PE38QQR and ephrinA1-PE38QQR (FIG. 12A). These results support the need for specific combinatorial approach simultaneously targeting multiple markers in order to have a single therapeutic option suitable for all GBM patients.

The foregoing is illustrative of the present invention, and is not to be construed as limiting thereof. The invention is defined by the following claims, with equivalents of the claims to be included therein.

That which is claimed is:

1. A method of treating a cancer expressing the oncogenic receptor EphA2 in a subject, comprising:
    administering active ephrinA1 in monomeric form to said subject in a treatment effective amount, wherein said active ephrinA1 in monomeric form is coupled to a therapeutic agent.

2. The method of claim 1, wherein said therapeutic agent is a radionuclide, chemotherapeutic agent or cytotoxic agent.

3. The method of claim 1, wherein said therapeutic agent comprises a *Pseudomonas* exotoxin.

4. The method of claim 1, wherein said cancer is selected from the group consisting of breast cancer, bladder cancer, pancreatic cancer, colorectal cancer, head and neck cancer, thyroid cancer, prostate cancer, and gliomas.

5. The method of claim 1, wherein the active ephrinA1 in monomeric form is provided in a pharmaceutically acceptable carrier.

6. The method of claim 1, wherein the active ephrinA1 in monomeric form coupled to a therapeutic agent is a fusion protein.

7. The method of claim 1, wherein the active ephrinA1 in monomeric form is conjugated as a fusion protein to a *Pseudomonas* exotoxin or a Diptheria toxin.

8. The method of claim 1, wherein the active ephrinA1 in monomeric form has a sequence selected from the group consisting of SEQ ID NO: 1, SEQ ID NO: 3, SEQ ID NO: 5, and SEQ ID NO: 7.

9. The method of claim 1, wherein the active ephrinA1 in monomeric form is produced by expressing a recombinant nucleic acid encoding said active ephrinA1 in a eukaryotic expression system.

* * * * *

SEQUENCE LISTING

<160> NUMBER OF SEQ ID NOS: 22

<210> SEQ ID NO 1
<211> LENGTH: 205
<212> TYPE: PRT
<213> ORGANISM: Homo sapiens

<400> SEQUENCE: 1

```
Met Glu Phe Leu Trp Ala Pro Leu Leu Gly Leu Cys Cys Ser Leu Ala
1               5                   10                  15

Ala Ala Asp Arg His Thr Val Phe Trp Asn Ser Ser Asn Pro Lys Phe
            20                  25                  30

Arg Asn Glu Asp Tyr Thr Ile His Val Gln Leu Asn Asp Tyr Val Asp
        35                  40                  45

Ile Ile Cys Pro His Tyr Glu Asp His Ser Val Ala Asp Ala Ala Met
    50                  55                  60

Glu Gln Tyr Ile Leu Tyr Leu Val Glu His Glu Glu Tyr Gln Leu Cys
65                  70                  75                  80

Gln Pro Gln Ser Lys Asp Gln Val Arg Trp Gln Cys Asn Arg Pro Ser
                85                  90                  95

Ala Lys His Gly Pro Glu Lys Leu Ser Glu Lys Phe Gln Arg Phe Thr
            100                 105                 110

Pro Phe Thr Leu Gly Lys Glu Phe Lys Glu Gly His Ser Tyr Tyr Tyr
        115                 120                 125

Ile Ser Lys Pro Ile His Gln His Glu Asp Arg Cys Leu Arg Leu Lys
    130                 135                 140

Val Thr Val Ser Gly Lys Ile Thr His Ser Pro Gln Ala His Val Asn
145                 150                 155                 160

Pro Gln Glu Lys Arg Leu Ala Ala Asp Asp Pro Glu Val Arg Val Leu
                165                 170                 175

His Ser Ile Ala His Ser Ala Ala Pro Arg Leu Phe Pro Leu Ala Trp
            180                 185                 190

Thr Val Leu Leu Leu Pro Leu Leu Leu Gln Thr Pro
        195                 200                 205
```

<210> SEQ ID NO 2
<211> LENGTH: 1519
<212> TYPE: DNA
<213> ORGANISM: Homo sapiens

<400> SEQUENCE: 2

```
ccacgcgtcc ggcgctgact gcgccgcgga gaaagccagt gggaacccag acccatagga      60
gacccgcgtc cccgctcggc ctggccaggc cccgcgctat ggagttcctc tgggcccctc     120
tcttgggtct gtgctgcagt ctggccgctg ctgatcgcca caccgtcttc tggaacagtt     180
caaatcccaa gttccggaat gaggactaca ccatacatgt gcagctgaat gactacgtgg     240
acatcatctg tccgcactat gaagatcact ctgtggcaga cgctgccatg gagcagtaca     300
tactgtacct ggtggagcat gaggagtacc agctgtgcca gccccagtcc aaggaccaag     360
```

-continued

| | |
|---|---|
| tccgctggca gtgcaaccgg cccagtgcca agcatggccc ggagaagctg tctgagaagt | 420 |
| tccagcgctt cacaccttc accctgggca aggagttcaa agaaggacac agctactact | 480 |
| acatctccaa acccatccac cagcatgaag accgctgctt gaggttgaag gtgactgtca | 540 |
| gtggcaaaat cactcacagt cctcaggccc atgtcaatcc acaggagaag agacttgcag | 600 |
| cagatgaccc agaggtgcgg gttctacata gcatcgctca cagtgctgcc ccacgcctct | 660 |
| tcccacttgc ctggactgtg ctgctccttc cacttctgct gctgcaaacc ccgtgaaggt | 720 |
| gtatgccaca cctggcctta agagggaca ggctgaagag agggacaggc actccaaacc | 780 |
| tgtcttgggg ccactttcag agccccagc cctgggaacc actccaccca caggcataag | 840 |
| ctatcaccta gcagcctcaa acgggtcag tattaaggtt ttcaaccgga aggaggccaa | 900 |
| ccagcccgac agtgccatcc ccaccttcac ctcggaggga tggagaaaga agtggagaca | 960 |
| gtcctttccc accattcctg cctttaagcc aaagaaacaa gctgtgcagg catggtccct | 1020 |
| taaggcacag tgggagctga gctggaaggg gccacgtgga tgggcaaagc ttgtcaaaga | 1080 |
| tgccccctcc aggagagagc caggatgccc agatgaactg actgaaggaa aagcaagaaa | 1140 |
| cagtttcttg cttggaagcc aggtacagga gaggcagcat gcttgggctg acccagcatc | 1200 |
| tcccagcaag acctcatctg tggagctgcc acagagaagt ttgtagccag gtactgcatt | 1260 |
| ctctcccatc ctggggcagc actccccaga gctgtgccag caggggggct gtgccaacct | 1320 |
| gttcttagag tgtagctgta agggcagtgc ccatgtgtac attctgccta gagtgtagcc | 1380 |
| taaagggcag ggcccacgtg tatagtatct gtatataagt tgctgtgtgt ctgtcctgat | 1440 |
| ttctacaact ggagtttttt tatacaatgt tctttgtctc aaaataaagc aatgtgtttt | 1500 |
| ttcgaaaaaa aaaaaaaaa | 1519 |

<210> SEQ ID NO 3
<211> LENGTH: 205
<212> TYPE: PRT
<213> ORGANISM: Homo sapiens

<400> SEQUENCE: 3

Met Glu Phe Leu Trp Ala Pro Leu Leu Gly Leu Cys Cys Ser Leu Ala
1               5                   10                  15

Ala Ala Asp Arg His Thr Val Phe Trp Asn Ser Ser Asn Pro Lys Phe
            20                  25                  30

Arg Asn Glu Asp Tyr Thr Ile His Val Gln Leu Asn Asp Tyr Val Asp
        35                  40                  45

Ile Ile Cys Pro His Tyr Glu Asp His Ser Val Ala Asp Ala Ala Met
    50                  55                  60

Glu Gln Tyr Ile Leu Tyr Leu Val Glu His Glu Glu Tyr Gln Leu Cys
65                  70                  75                  80

Gln Pro Gln Ser Lys Asp Gln Val Arg Trp Gln Cys Asn Arg Pro Ser
                85                  90                  95

Ala Lys His Gly Pro Glu Lys Leu Ser Glu Lys Phe Gln Arg Phe Thr
            100                 105                 110

Pro Phe Thr Leu Gly Lys Glu Phe Lys Glu Gly His Ser Tyr Tyr Tyr
        115                 120                 125

Ile Ser Lys Pro Ile His Gln His Glu Asp Arg Cys Leu Arg Leu Lys
    130                 135                 140

Val Thr Val Ser Gly Lys Ile Thr His Ser Pro Gln Ala His Asp Asn
145                 150                 155                 160

Pro Gln Glu Lys Arg Leu Ala Ala Asp Asp Pro Glu Val Arg Val Leu 165                 170                 175
His Ser Ile Gly His Ser Ala Ala Pro Arg Leu Phe Pro Leu Ala Trp
            180                 185                 190
Thr Val Leu Leu Leu Pro Leu Leu Leu Gln Thr Pro
            195                 200                 205

<210> SEQ ID NO 4
<211> LENGTH: 1590
<212> TYPE: DNA
<213> ORGANISM: Homo sapiens

<400> SEQUENCE: 4

| | |
|---|---|
| gccagatctg tgagcccagc gctgactgcg ccgcggagaa agccagtggg aacccagacc | 60 |
| cataggagac ccgcgtcccc gctcggcctg gccaggcccc cgctatgga gttcctctgg | 120 |
| gccctctct tgggtctgtg ctgcagtctg gccgctgctg atcgccacac cgtcttctgg | 180 |
| aacagttcaa atcccaagtt ccggaatgag gactacacca tacatgtgca gctgaatgac | 240 |
| tacgtggaca tcatctgtcc gcactatgaa atcactctg tggcagacgc tgccatggag | 300 |
| cagtacatac tgtacctggt ggagcatgag gagtaccagc tgtgccagcc ccagtccaag | 360 |
| gaccaagtcc gctggcagtg caaccggccc agtgccaagc atggcccgga aagctgtct | 420 |
| gagaagttcc agcgcttcac acctttcacc ctgggcaagg agttcaaaga aggacacagc | 480 |
| tactactaca tctccaaacc catccaccag catgaagacc gctgcttgag gttgaaggtg | 540 |
| actgtcagtg gcaaaatcac tcacagtcct caggcccatg acaatccaca ggagaagaga | 600 |
| cttgcagcag atgacccaga ggtgcgggtt ctacatagca tcggtcacag tgctgccca | 660 |
| cgcctcttcc cacttgcctg gactgtgctg ctccttccac ttctgctgct gcaaacccg | 720 |
| tgaaggtgta tgccacacct ggccttaaag agggacaggc tgaagagagg gacaggcact | 780 |
| ccaaacctgt cttggggcca ctttcagagc ccccagccct gggaaccact cccaccacag | 840 |
| gcataagcta tcacctagca gcctcaaaac gggtcagtat taaggttttc aaccggaagg | 900 |
| aggccaacca gcccgacagt gccatcccca ccttcacctc ggagggatgg agaaagaagt | 960 |
| ggagacagtc ctttcccacc attcctgcct ttaagccaaa gaaacaagct gtgcaggcat | 1020 |
| ggtcccttaa ggcacagtgg gagctgagct ggaaggggcc acgtggatgg gcaaagcttg | 1080 |
| tcaaagatgc cccctccagg agagagccag gatgcccaga tgaactgact gaaggaaaag | 1140 |
| caagaaacag tttcttgctt ggaagccagg tacaggagag gcagcatgct tgggctgacc | 1200 |
| cagcatctcc cagcaagacc tcatctgtgg agctgccaca gagaagtttg tagccaggta | 1260 |
| ctgcattctc tcccatcctg gggcagcact ccccagagct gtgccagcag ggggctgtg | 1320 |
| ccaacctgtt cttagagtgt agctgtaagg gcagtgccca tgtgtacatt ctgcctagag | 1380 |
| tgtagcctaa agggcagggc ccacgtgtat agtatctgta tataagttgc tgtgtgtctg | 1440 |
| tcctgatttc tacaactgga gttttttat acaatgttct ttgtctcaaa ataaagcaat | 1500 |
| gtgtttttc ggacatgctt ttctgccact ccatattaaa acatatgacc attgagtccc | 1560 |
| tgctaaaaaa aaaaaaaaa aaaaaaaaa | 1590 |

<210> SEQ ID NO 5
<211> LENGTH: 183
<212> TYPE: PRT
<213> ORGANISM: Homo sapiens

<400> SEQUENCE: 5

Met Glu Phe Leu Trp Ala Pro Leu Leu Gly Leu Cys Cys Ser Leu Ala

```
  1               5                  10                 15
Ala Ala Asp Arg His Thr Val Phe Trp Asn Ser Ser Asn Pro Lys Phe
                20                  25                 30
Arg Asn Glu Asp Tyr Thr Ile His Val Gln Leu Asn Asp Tyr Val Asp
                35                  40                 45
Ile Ile Cys Pro His Tyr Glu Asp His Ser Val Ala Asp Ala Ala Met
            50                  55                 60
Glu Gln Tyr Ile Leu Tyr Leu Val Glu His Glu Glu Tyr Gln Leu Cys
65                  70                  75                 80
Gln Pro Gln Ser Lys Asp Gln Val Arg Trp Gln Cys Asn Arg Pro Ser
                85                  90                 95
Ala Lys His Gly Pro Glu Lys Leu Ser Glu Lys Phe Gln Arg Phe Thr
                100                 105                110
Pro Phe Thr Leu Gly Lys Glu Lys Glu Gly His Ser Tyr Tyr Tyr
                115                 120                125
Ile Ser His Ser Pro Gln Ala His Asp Asn Pro Gln Glu Lys Arg Leu
            130                 135                140
Ala Ala Asp Asp Pro Glu Val Arg Val Leu His Ser Ile Gly His Ser
145                 150                 155                160
Ala Ala Pro Arg Leu Phe Pro Leu Ala Trp Thr Val Leu Leu Leu Pro
                165                 170                175
Leu Leu Leu Leu Gln Thr Pro
            180
```

<210> SEQ ID NO 6
<211> LENGTH: 1524
<212> TYPE: DNA
<213> ORGANISM: Homo sapiens

<400> SEQUENCE: 6

```
gccagatctg tgagcccagc gctgactgcg ccgcggagaa agccagtggg aacccagacc        60
cataggagac ccgcgtcccc gctcggcctg gccaggcccc gcgctatgga gttcctctgg       120
gcccctctct tgggtctgtg ctgcagtctg ccgctgctg atcgccacac cgtcttctgg        180
aacagttcaa atcccaagtt ccggaatgag actacacca tacatgtgca gctgaatgac        240
tacgtggaca tcatctgtcc gcactatgaa gatcactctg tggcagacgc tgccatggag        300
cagtacatac tgtacctggt ggagcatgag gagtaccagc tgtgccagcc ccagtccaag        360
gaccaagtcc gctggcagtg caaccggccc agtgccaagc atgggccgga gaagctgtct        420
gagaagttcc agcgcttcac cctttcacc ctgggcaagg agttcaaaga aggacacagc        480
tactactaca tctctcacag tcctcaggcc catgacaatc cacaggagaa agacttgca        540
gcagatgacc cagaggtgcg ggttctacat agcatcggtc acagtgctgc cccacgcctc        600
ttcccacttg cctggactgt gctgctcctt ccacttctgc tgctgcaaac cccgtgaagg       660
tgtatgccac acctggcctt aaagagggac aggctgaaga gagggacagg cactccaaac        720
ctgtcttggg gccactttca gagccccag ccctgggaac cactcccacc acaggcataa        780
gctatcacct agcagcctca aaacgggtca gtattaaggt tttcaaccgg aaggaggcca        840
accagcccga cagtgccatc cccaccttca cctcggaggg atgagaaag aagtggagac         900
agtcctttcc caccattcct gcctttaagc caaagaaaca agctgtgcag gcatggtccc        960
ttaaggcaca gtgggagctg agctggaagg ggcacgtgg atgggcaaag cttgtcaaag       1020
atgcccctc caggagagag ccaggatgcc cagatgaact gactgaagga aaagcaagaa       1080
```

| | | | | |
|---|---|---|---|---|
| acagtttctt | gcttggaagc | caggtacagg | agaggcagca | tgcttgggct gacccagcat | 1140 |
| ctcccagcaa | gacctcatct | gtggagctgc | cacagagaag | tttgtagcca ggtactgcat | 1200 |
| tctctcccat | cctggggcag | cactccccag | agctgtgcca | gcagggggc tgtgccaacc | 1260 |
| tgttcttaga | gtgtagctgt | aagggcagtg | cccatgtgta | cattctgcct agagtgtagc | 1320 |
| ctaaagggca | gggcccacgt | gtatagtatc | tgtatataag | ttgctgtgtg tctgtcctga | 1380 |
| tttctacaac | tggagttttt | ttatacaatg | ttctttgtct | caaataaag caatgtgttt | 1440 |
| tttcggacat | gcttttctgc | cactccatat | taaaacatat | gaccattgag tccctgctaa | 1500 |
| aaaaaaaaaa | aaaaaaaaaa | aaaa | | | 1524 |

<210> SEQ ID NO 7
<211> LENGTH: 205
<212> TYPE: PRT
<213> ORGANISM: Mus musculus

<400> SEQUENCE: 7

Met Glu Phe Leu Trp Ala Pro Leu Leu Gly Leu Cys Cys Ser Leu Ala
1               5                   10                  15

Ala Ala Asp Arg His Ile Val Phe Trp Asn Ser Ser Asn Pro Lys Phe
            20                  25                  30

Arg Glu Glu Asp Tyr Thr Val His Val Gln Leu Asn Asp Tyr Leu Asp
        35                  40                  45

Ile Ile Cys Pro His Tyr Glu Asp Ser Val Ala Asp Ala Ala Met
    50                  55                  60

Glu Arg Tyr Thr Leu Tyr Met Val Glu His Gln Glu Tyr Val Ala Cys
65                  70                  75                  80

Gln Pro Gln Ser Lys Asp Gln Val Arg Trp Asn Cys Asn Arg Pro Ser
                85                  90                  95

Ala Lys His Gly Pro Glu Lys Leu Ser Val Lys Phe Gln Arg Phe Thr
            100                 105                 110

Pro Phe Ile Leu Gly Lys Glu Phe Lys Glu Gly His Ser Tyr Tyr Tyr
        115                 120                 125

Ile Ser Lys Pro Ile Tyr His Gln Glu Ser Gln Cys Leu Lys Leu Lys
    130                 135                 140

Val Thr Val Asn Gly Lys Ile Thr His Asn Pro Gln Ala His Val Asn
145                 150                 155                 160

Pro Gln Glu Lys Arg Leu Gln Ala Asp Asp Pro Glu Val Gln Val Leu
                165                 170                 175

His Ser Ile Gly Tyr Ser Ala Pro Arg Leu Phe Pro Leu Val Trp
            180                 185                 190

Ala Val Leu Leu Leu Pro Leu Leu Leu Leu Gln Ser Gln
        195                 200                 205

<210> SEQ ID NO 8
<211> LENGTH: 1473
<212> TYPE: DNA
<213> ORGANISM: Mus musculus

<400> SEQUENCE: 8

| | | | | |
|---|---|---|---|---|
| agatttgtga | tcgtggtgcc | tactgtaccg | tggagaagcc | tgtgggaacc ttacactgca | 60 |
| gagctctcgt | cctggcctgg | ctcggcccgg | ccccgcgcta | tggagttcct ttgggcccct | 120 |
| ctcttgggtc | tgtgctgcag | tctggccgct | gctgaccgcc | acatcgtctt ctggaacagt | 180 |
| tcaaatccca | agttccgtga | ggaggactac | acggtgcacg | tgcagctgaa tgactaccta | 240 |

-continued

```
gacatcatct gcccacatta cgaggacgac tctgtggcag atgcagccat ggagcgatac    300
acactgtaca tggtggaaca ccaggagtat gtggcatgcc aacccagtc aaggaccag      360
gtccgttgga attgcaaccg gcccagtgcc aagcatggcc cggagaagct gtctgtgaaa    420
ttccagcgct tcacgccttt tatcttgggc aaggagttca aggaaggaca cagctactac    480
tacatctcca aacctatcta ccatcaggaa tcccagtgct gaagctgaa ggtgactgtc    540
aatggcaaaa tcactcataa tccccaggcc catgtcaacc acaggagaa gagactccaa     600
gcagatgacc cggaagtaca ggttttgcac agcattggtt acagtgccgc ccccgcctc    660
ttcccactgg tctgggcagt attgctccta ccactgctgc tgctgcaatc tcagtgaggg    720
tgtacgcttg ccctggctta tggattggaa tgggactaag gggcagcccc agccctggga    780
acctctccca ctacacccac aagacgccca catgaagcct caaaaggttc agtattaagg    840
gttttaaccg aaaagagttt aaccagccca actgtgccat ccctgcctcc acttcagagg    900
gatggagaaa gaagtggaga aggtccttaa cctgcagttt ctgcctttaa gccaaagaaa    960
caagctgtgc ggacctggcc cattaagagg cctcagtggg agaagggcta aaagagcct   1020
gaggtcatgc ggttggacac tgaacttggt aaagacgtcc ttccccaagg aagccataat   1080
gtgcagatga actgaccgaa ggaaaagctt gagacagctc cctgcggggg agccaggtac   1140
agaagaggca gcttgggctg acccagcatc tctgcaagat ttccacctgc tgggctgcca   1200
gagaggtttg tagcccggcc ctgactgcat cctccccatc cctggggcaa cattccctgg   1260
agctgtgcca acaggaggac tgaagcagcc tggttttaga gtgtagctgt aagggcagtg   1320
cccgtgtgta cagtctgtgg agtttagctt aacgggcagg gcccacatgt acagtgtctg   1380
tatataaatg tgctgtatct gttcatttct atgactgcag ggttttttta tacagtgttt   1440
ttggattcat ataaattga tggtttttta tgg                                 1473
```

<210> SEQ ID NO 9
<211> LENGTH: 146
<212> TYPE: PRT
<213> ORGANISM: Homo sapiens

<400> SEQUENCE: 9

```
Met His Pro Leu Leu Asn Pro Leu Leu Leu Ala Leu Gly Leu Met Ala
1               5                   10                  15

Leu Leu Leu Thr Thr Val Ile Ala Leu Thr Cys Leu Gly Gly Phe Ala
            20                  25                  30

Ser Pro Gly Pro Val Pro Pro Ser Thr Ala Leu Arg Glu Leu Ile Glu
        35                  40                  45

Glu Leu Val Asn Ile Thr Gln Asn Gln Lys Ala Pro Leu Cys Asn Gly
    50                  55                  60

Ser Met Val Trp Ser Ile Asn Leu Thr Ala Gly Met Tyr Cys Ala Ala
65                  70                  75                  80

Leu Glu Ser Leu Ile Asn Val Ser Gly Cys Ser Ala Ile Glu Lys Thr
                85                  90                  95

Gln Arg Met Leu Ser Gly Phe Cys Pro His Lys Val Ser Ala Gly Gln
            100                 105                 110

Phe Ser Ser Leu His Val Arg Asp Thr Lys Ile Glu Val Ala Gln Phe
        115                 120                 125

Val Lys Asp Leu Leu Leu His Leu Lys Lys Leu Phe Arg Glu Gly Gln
    130                 135                 140

Phe Asn
145
```

```
<210> SEQ ID NO 10
<211> LENGTH: 1282
<212> TYPE: DNA
<213> ORGANISM: Homo sapiens

<400> SEQUENCE: 10
aagccaccca gcctatgcat ccgctcctca atcctctcct gttggcactg ggcctcatgg      60
cgcttttgtt gaccacggtc attgctctca cttgccttgg cggctttgcc tcccaggcc     120
ctgtgcctcc ctctacagcc ctcagggagc tcattgagga gctggtcaac atcacccaga    180
accagaaggc tccgctctgc aatggcagca tggtatggag catcaacctg acagctggca    240
tgtactgtgc agccctggaa tcctgatca acgtgtcagg ctgcagtgcc atcgagaaga     300
cccagaggat gctgagcgga ttctgcccgc acaaggtctc agctgggcag ttttccagct    360
tgcatgtccg agacaccaaa atcgaggtgg cccagtttgt aaaggacctg ctcttacatt    420
taaagaaact ttttcgcgag ggacagttca actgaaactt cgaaagcatc attatttgca    480
gagacaggac ctgactattg aagttgcaga ttcattttc tttctgatgt caaaaatgtc     540
ttgggtaggc gggaaggagg gttagggagg ggtaaaattc cttagcttag acctcagcct    600
gtgctgcccg tcttcagcct agccgacctc agccttcccc ttgcccaggg ctcagcctgg    660
tgggcctcct ctgtccaggg ccctgagctc ggtggaccca gggatgacat gtccctacac    720
ccctcccctg ccctagagca cactgtagca ttacagtggg tgccccccctt gccagacatg    780
tggtgggaca gggacccact tcacacacag gcaactgagg cagacagcag ctcaggcaca    840
cttcttcttg gtcttattta ttattgtgtg ttatttaaat gagtgtgttt gtcaccgttg    900
gggattgggg aagactgtgg ctgctagcac ttggagccaa gggttcagag actcagggcc    960
ccagcactaa agcagtggac accaggagtc cctggtaata agtactgtgt acagaattct   1020
gctacctcac tggggtcctg ggcctcgga gcctcatccg aggcagggtc aggagagggg    1080
cagaacagcc gctcctgtct gccagccagc agccagctct cagccaacga gtaatttatt   1140
gttttttcctt gtatttaaat attaaatatg ttagcaaaga gttaatatat agaagggtac  1200
cttgaacact gggggagggg acattgaaca agttgtttca ttgactatca aactgaagcc    1260
agaaataaag ttggtgacag at                                              1282

<210> SEQ ID NO 11
<211> LENGTH: 131
<212> TYPE: PRT
<213> ORGANISM: Mus musculus

<400> SEQUENCE: 11

Met Ala Leu Trp Val Thr Ala Val Leu Ala Leu Ala Cys Leu Gly Gly
1               5                   10                  15

Leu Ala Ala Pro Gly Pro Val Pro Arg Ser Val Ser Leu Pro Leu Thr
            20                  25                  30

Leu Lys Glu Leu Ile Glu Glu Leu Ser Asn Ile Thr Gln Asp Gln Thr
        35                  40                  45

Pro Leu Cys Asn Gly Ser Met Val Trp Ser Val Asp Leu Ala Ala Gly
    50                  55                  60

Gly Phe Cys Val Ala Leu Asp Ser Leu Thr Asn Ile Ser Asn Cys Asn
65                  70                  75                  80

Ala Ile Tyr Arg Thr Gln Arg Ile Leu His Gly Leu Cys Asn Arg Lys
                85                  90                  95
```

Ala Pro Thr Thr Val Ser Ser Leu Pro Asp Thr Lys Ile Glu Val Ala
            100                 105                 110

His Phe Ile Thr Lys Leu Leu Ser Tyr Thr Lys Gln Leu Phe Arg His
        115                 120                 125

Gly Pro Phe
    130

<210> SEQ ID NO 12
<211> LENGTH: 1206
<212> TYPE: DNA
<213> ORGANISM: Mus musculus

<400> SEQUENCE: 12

```
acaagccagc agcctaggcc agcccacagt tctacagctc cctggttctc tcactggctc     60
tgggcttcat ggcgctctgg gtgactgcag tcctggctct tgcttgcctt ggtggtctcg    120
ccgccccagg gccggtgcca agatctgtgt ctctccctct gacccttaag gagcttattg    180
aggagctgag caacatcaca aagaccagac tcccctgtg caacggcagc atggtatgga    240
gtgtggacct ggccgctggc gggttctgtg tagccctgga ttccctgacc aacatctcca    300
attgcaatgc catctacagg acccagagga tattgcatgg cctctgtaac cgcaaggccc    360
ccactacggt ctccagcctc cccgatacca aaatcgaagt agcccacttt ataacaaaac    420
tgctcagcta cacaaagcaa ctgtttcgcc acggccccct ctaatgagga gagaccatcc    480
ctgggcatct cagctgtgga ctcatttttc tttctcacat cagactttgc tggggagagg    540
cagggaggag ggttgaggag aagggagat gcctcagctt tggcctcagc ctgcactgcc    600
tgcctagtgc tcagggtctc agcctggcaa caccccacc ccaccccac cccgccgcc    660
ccatcccatc cctacagaaa actgcagcaa gaccgtgagt ccagcctgtg gcctggtcca    720
cacagggcaa ctgaggcagg cagcagcttg agcacatttc ttcttgatct tatttattat    780
ggttgtgtgt tatttaaatg agtctgtcag tatcccggtg gggacatggt ttgctgccta    840
tgccctgggg gctccagcat tgaagcagtg ggctctgggg tccctggcaa tattactgta    900
tacataactc tgctacctca ctgtagcctc caggtctcac cccaggcagg gagatgggag    960
gggaggccag agcaacactc ctgtctgcca cggcagcaac cagccctcag ccatgaaata   1020
acttattgtt ttgttcttat atttaaagta ttaaatagct tagcaaagag ttaataatat   1080
atggaagaat ggcctgttac actcaaggtg atgtgtagtg aatgggggga gggtggtggg   1140
tttgtcactg aacaaacttt tcattgactg tcaaactaga aaccggaaat aaagatggtg   1200
acagat                                                              1206
```

<210> SEQ ID NO 13
<211> LENGTH: 131
<212> TYPE: PRT
<213> ORGANISM: Rattus norvegicus

<400> SEQUENCE: 13

Met Ala Leu Trp Val Thr Ala Val Leu Ala Leu Ala Cys Leu Gly Gly
1               5                   10                  15

Leu Ala Thr Pro Gly Pro Val Arg Arg Ser Thr Ser Pro Pro Val Ala
            20                  25                  30

Leu Arg Glu Leu Ile Glu Glu Leu Ser Asn Ile Thr Gln Asp Gln Lys
        35                  40                  45

Thr Ser Leu Cys Asn Ser Ser Met Val Trp Ser Val Asp Leu Thr Ala
    50                  55                  60

```
Gly Gly Phe Cys Ala Ala Leu Glu Ser Leu Thr Asn Ile Ser Ser Cys
 65                  70                  75                  80

Asn Ala Ile His Arg Thr Gln Arg Ile Leu Asn Gly Leu Cys Asn Gln
                 85                  90                  95

Lys Ala Ser Asp Val Ala Ser Ser Pro Pro Asp Thr Lys Ile Glu Val
            100                 105                 110

Ala Gln Phe Ile Ser Lys Leu Leu Asn Tyr Ser Lys Gln Leu Phe Arg
        115                 120                 125

Tyr Gly His
        130

<210> SEQ ID NO 14
<211> LENGTH: 443
<212> TYPE: DNA
<213> ORGANISM: Rattus norvegicus

<400> SEQUENCE: 14
atggcactct gggtgactgc agtcctggct ctcgcttgcc ttggtggtct tgccacccca      60
gggccagtgc ggagatccac atctccccct gtggccctca gggagcttat cgaggagctg     120
agcaacatca cacaagacca gaagacttcc ctgtgcaaca gcagcatggt atggagcgtg     180
gacctgacag ctggcgggtt ctgtgcagcc ctggaatccc tgaccaacat ctccagttgc     240
aatgccatcc acaggaccca gaggatattg aatggcctct gtaaccaaaa ggcctcggat     300
gtggcttcca gccccccaga taccaaaatc gaagtagccc agtttatatc aaaactgctc     360
aattactcca gcaacttttt ccgctatggc cactgagggg agaccggccc tggacatctc     420
agctgtggac ctcagttgtg gat                                              443

<210> SEQ ID NO 15
<211> LENGTH: 271
<212> TYPE: PRT
<213> ORGANISM: Homo sapiens

<400> SEQUENCE: 15

Met Phe Arg Asp Phe Gly Glu Pro Gly Pro Ser Ser Gly Asn Gly Gly
  1               5                  10                  15

Gly Tyr Gly Gly Pro Ala Gln Pro Pro Ala Ala Gln Ala Ala Gln
             20                  25                  30

Gln Lys Phe His Leu Val Pro Ser Ile Asn Thr Met Ser Gly Ser Gln
         35                  40                  45

Glu Leu Gln Trp Met Val Gln Pro His Phe Leu Gly Pro Ser Ser Tyr
 50                  55                  60

Pro Arg Pro Leu Thr Tyr Pro Gln Tyr Ser Pro Pro Gln Pro Arg Pro
 65                  70                  75                  80

Gly Val Ile Arg Ala Leu Gly Pro Pro Gly Val Arg Arg Arg Pro
             85                  90                  95

Cys Glu Gln Ile Ser Pro Glu Glu Glu Arg Arg Arg Val Arg Arg
            100                 105                 110

Glu Arg Asn Lys Leu Ala Ala Ala Lys Cys Arg Asn Arg Arg Lys Glu
        115                 120                 125

Leu Thr Asp Phe Leu Gln Ala Glu Thr Asp Lys Leu Glu Asp Glu Lys
        130                 135                 140

Ser Gly Leu Gln Arg Glu Ile Glu Glu Leu Gln Lys Gln Lys Glu Arg
145                 150                 155                 160

Leu Glu Leu Val Leu Glu Ala His Arg Pro Ile Cys Lys Ile Pro Glu
                165                 170                 175
```

Gly Ala Lys Glu Gly Asp Thr Gly Ser Thr Ser Gly Thr Ser Ser Pro
            180                 185                 190

Pro Ala Pro Cys Arg Pro Val Pro Cys Ile Ser Leu Ser Pro Gly Pro
        195                 200                 205

Val Leu Glu Pro Glu Ala Leu His Thr Pro Thr Leu Met Thr Thr Pro
    210                 215                 220

Ser Leu Thr Pro Phe Thr Pro Ser Leu Val Phe Thr Tyr Pro Ser Thr
225                 230                 235                 240

Pro Glu Pro Cys Ala Ser Ala His Arg Lys Ser Ser Ser Ser Ser Gly
                245                 250                 255

Asp Pro Ser Ser Asp Pro Leu Gly Ser Pro Thr Leu Leu Ala Leu
            260                 265                 270

<210> SEQ ID NO 16
<211> LENGTH: 954
<212> TYPE: DNA
<213> ORGANISM: Homo sapiens

<400> SEQUENCE: 16
agccgtgtac cccgcagagc cgccagcccc gggcatgttc cgagacttcg gggaacccgg     60
cccgagctcc gggaacggcg gcgggtacgg cggccccgcg cagcccccgg ccgcagcgca    120
ggcagcccag cagaagttcc acctggtgcc aagcatcaac accatgagtg cagtcagga    180 gctgcagtgg atggtacagc ctcatttcct ggggcccagc agttacccca ggcctctgac    240
ctaccctcag tacagccccc acaaccccg gccaggagtc atccgggccc tggggccgcc    300 tccagggta cgtcgaaggc cttgtgaaca gatcagcccg aggaagagg agcgccgccg    360 agtaaggcgc gagcggaaca agctggctgc ggccaagtgc aggaaccgga ggaaggaact    420
gaccgacttc ctgcaggcgg agactgacaa actggaagat gagaaatctg gctgcagcg    480 agagattgag gagctgcaga gcagaaggga gcgcctagag ctggtgctgg aagcccaccg    540
acccatctgc aaaatcccgg aaggagccaa ggaggggac acaggcagta ccagtggcac    600
cagcagccca ccagcccct gccgcccgtg accttgtatc tcccttcc cagggcctgt    660 gcttgaacct gaggcactgc acaccccac actcatgacc acaccctccc taactccttt    720 caccccagc ctggtcttca cctacccag cactcctgag ccttgtgcct cagctcatcg    780
caagagtagc agcagcagcg gagacccatc tctgacccc cttggctctc aaccctcct    840 cgctttgtga ggcgcctgag ccctactccc tgcagatgcc accctagcca atgtctcctc    900 ccccttccccc accggtccag ctggcctgga cagtatccca catccaactc cagc         954

<210> SEQ ID NO 17
<211> LENGTH: 275
<212> TYPE: PRT
<213> ORGANISM: Rattus norvegicus

<400> SEQUENCE: 17

Met Tyr Arg Asp Phe Gly Glu Pro Gly Pro Ser Ser Gly Ala Gly Ser
1               5                   10                  15

Ala Tyr Gly Arg Pro Ala Gln Pro Gln Gln Ala Gln Thr Gln Thr Val
            20                  25                  30

Gln Gln Gln Lys Phe His Leu Val Pro Ser Ile Asn Ala Val Ser Gly
        35                  40                  45

Ser Gln Glu Leu Gln Trp Met Val Gln Pro His Phe Leu Gly Pro Ser
    50                  55                  60

Gly Tyr Pro Arg Pro Leu Thr Tyr Pro Gln Tyr Ser Pro Pro Gln Pro
65                  70                  75                  80

Arg Pro Gly Val Ile Arg Ala Leu Gly Pro Pro Gly Val Arg Arg
                85                  90                  95

Arg Pro Cys Glu Gln Ile Ser Pro Glu Glu Glu Arg Arg Arg Val
            100                 105                 110

Arg Arg Glu Arg Asn Lys Leu Ala Ala Ala Lys Cys Arg Asn Arg Arg
            115                 120                 125

Lys Glu Leu Thr Asp Phe Leu Gln Ala Glu Thr Asp Lys Leu Glu Asp
            130                 135                 140

Glu Lys Ser Gly Leu Gln Arg Glu Ile Glu Glu Leu Gln Lys Gln Lys
145                 150                 155                 160

Glu Arg Leu Glu Leu Val Leu Glu Ala His Arg Pro Ile Cys Lys Ile
                165                 170                 175

Pro Glu Glu Asp Lys Lys Asp Thr Gly Gly Thr Ser Ser Thr Ser Gly
                180                 185                 190

Ala Gly Ser Pro Pro Gly Pro Cys Arg Pro Val Pro Cys Ile Ser Leu
            195                 200                 205

Ser Pro Gly Pro Val Leu Glu Pro Glu Ala Leu His Thr Pro Thr Leu
210                 215                 220

Met Thr Thr Pro Ser Leu Thr Pro Phe Thr Pro Ser Leu Val Phe Thr
225                 230                 235                 240

Tyr Pro Ser Thr Pro Glu Pro Cys Ser Ser Ala His Arg Lys Ser Ser
                245                 250                 255

Ser Ser Ser Gly Asp Pro Ser Ser Asp Pro Leu Gly Ser Pro Thr Leu
            260                 265                 270

Leu Ala Leu
        275

<210> SEQ ID NO 18
<211> LENGTH: 1663
<212> TYPE: DNA
<213> ORGANISM: Rattus norvegicus

<400> SEQUENCE: 18
cctgggggtc gtgaagttcc gagcggacgg gtccacggag gttcatctgg agaggtgggt      60
cccctgcgag gtgaaaggcg ccgctgcgac acacccccac cccccgcggt gcagtggttc     120
agcccaataa cttttcattc ataaaaaaga ccagactctg cgaggcgcga gtgagtcaga     180
accgcagccg ccgacgcgga ccctaccgaa catccagccc agggcatgta ccgagacttc     240
ggggaaccgg gaccgagttc cggggctggc agcgcgtacg gtcgccccgc gcagccccag     300
caagcgcaga cacagacagt ccagcagcag aagttccacc ttgtgccaag catcaacgct     360
gtcagtggca gccaggaatt gcagtggatg gtgcagcctc atttcctggg acccagcggc     420
tatccccgac tctgacccta tccccagtac agtcccccctc agccccgacc aggagtcata     480
cgagccctag ggccacctcc aggggtgcga cgcaggccct gtgagcagat cagcccggag     540
gaggaagagc gccgcagggt gagacgcgag cggaacaagc tagcagctgc taagtgcaga     600
aaccgaagaa aggaattgac agacttcctg caggcggaga ccgacaagtt ggaggatgag     660
aaatcggggc tgcagcgtga gatcgaagag ctgcagaagc agaaggaacg ccttgagctg     720
gtgctggaag cccatcgccc catctgcaaa atcccagaag aagacaagaa ggacacaggt     780
ggtaccagca gcacgagtgg ggcgggtagc ccaccgggcc cctgccgccc agtgccttgt     840
atctcccttt ctccaggacc cgtacttgaa ccggaagcac tgcataccccc cacgctcatg     900

```
accacaccct ctctgactcc ttttactccg agtctggttt tcacctatcc tagcacacca      960
gagccttgtt cctcagccca tcgaaagagt agcagcagca gtggtgaccc ctcctccgac     1020
cccctaggtt ctcccacact cctggctttg tgaggcaccc agccacaccc cttgcaggtg     1080
ctacccgttg tcatctcctt tccctgttca tccagcaggc ctggaccata ccatgcccc      1140
aaaccagcag gtcttttatc tctttcaagt agaacaaaca tgttatgctt tgatatagag     1200
ccagcttggg ggtccccaaa gctgctcact gtttctctag agctggccta tcataatttg     1260
catacagaga aaatatgtcc ctctgccaga gtaagcctgg cagctctgac tttgtagatc     1320
cccagtggtc ctttgatgcc ttgcagacca ctttcccaca ccatgtcact tcttcatgt      1380
tatccagcct actctaagcc tagatagaag gtgcccttta actagcctag aacactaact     1440
cacacagcac caacgccag cagcaccagg acaccctgta ggctcctcct gatcaggagg      1500
caccaacagc ttctgtgatg agctgagctg tactccctag ctctgagaag cttttagctc     1560
tggggtatcc aagcctccac agcaagggca gctgctattt attttcctaa agagactatt     1620
tttatacaaa ccttccaaaa tggaataaaa ggcttgaagc tct                      1663

<210> SEQ ID NO 19
<211> LENGTH: 273
<212> TYPE: PRT
<213> ORGANISM: Mus musculus

<400> SEQUENCE: 19

Met Tyr Arg Asp Tyr Gly Glu Pro Gly Pro Ser Ser Gly Ala Gly Ser
1               5                   10                  15

Ala Tyr Gly Arg Pro Ala Gln Pro Pro Gln Ala Gln Ala Gln Thr Ala
            20                  25                  30

Gln Gln Gln Lys Phe His Phe Val Pro Ser Ile Asp Ser Ser Ser Gln
        35                  40                  45

Glu Leu His Trp Met Val Gln Pro His Phe Leu Gly Pro Thr Gly Tyr
    50                  55                  60

Pro Arg Pro Leu Ala Tyr Pro Gln Tyr Ser Pro Gln Pro Arg Pro
65                  70                  75                  80

Gly Val Ile Arg Ala Leu Gly Pro Pro Gly Val Arg Arg Arg Pro
                85                  90                  95

Cys Glu Gln Ile Ser Pro Glu Glu Glu Arg Arg Val Arg Arg
            100                 105                 110

Glu Arg Asn Lys Leu Ala Ala Ala Lys Cys Arg Asn Arg Arg Lys Glu
        115                 120                 125

Leu Thr Asp Phe Leu Gln Ala Glu Thr Asp Lys Leu Glu Asp Glu Lys
    130                 135                 140

Ser Gly Leu Gln Arg Glu Ile Glu Glu Leu Gln Lys Gln Lys Glu Arg
145                 150                 155                 160

Leu Glu Leu Val Leu Glu Ala His Arg Leu Ile Cys Lys Ile Pro Glu
                165                 170                 175

Gly Asp Lys Lys Asp Pro Gly Gly Ser Gly Ser Thr Ser Gly Ala Ser
            180                 185                 190

Ser Pro Pro Ala Pro Gly Arg Pro Val Pro Cys Ile Ser Leu Ser Pro
        195                 200                 205

Gly Pro Val Leu Glu Pro Glu Ala Leu His Thr Pro Thr Leu Met Thr
    210                 215                 220

Thr Pro Ser Leu Thr Pro Phe Thr Pro Ser Leu Val Phe Thr Tyr Pro
225                 230                 235                 240
```

```
Ser Thr Pro Glu Pro Cys Ser Ser Thr His Arg Lys Ser Ser Ser Ser
                245                 250                 255

Ser Gly Asp Pro Ser Ser Asp Pro Leu Gly Ser Pro Thr Leu Leu Ala
            260                 265                 270

Leu

<210> SEQ ID NO 20
<211> LENGTH: 1034
<212> TYPE: DNA
<213> ORGANISM: Mus musculus

<400> SEQUENCE: 20
gtccacagag gttcatctgg agaggtgggt cccctgcgag gtgaaaggcg ccgctgagac      60
acgcccccac ccctgtggt gcaagtggtt cagcccaaga acttttcatt cataaaaaag     120
accagactcc gagaggcgcg agtgagtcag aaccgcagcc gccaacgcgg accctaccga    180
acatccagcc cagggcatgt accgagacta cggggaaccg ggaccgagct ccggggctgg    240
cagcgcgtac ggtcgccccg cgcagccccc gcaagctcag gcacagaccg cccagcagca    300
gaagttccac tttgtgccaa gcatcgacag cagcagccag gaactgcact ggatggtgca    360
gcctcatttc ctgggaccca ctggctatcc ccgacctctg gcctatcccc agtacagtcc    420
ccctcagccc cggccaggag tcatacgagc cctaggccca cctccggggg tgcgtcgcag    480
gccctgcgag cagatcagcc cagaggagga agagcgccgc agggtgagac gcgagcggaa    540
caagctagca gctgctaagt gcagaaaccg aagaaggag ctgacagact tcctgcaggc    600
ggagaccgac aaattggagg atgagaaatc ggggctgcag cgagagattg aagagctgca    660
gaagcagaag gaacgccttg agctggtgct ggaagcccat cgcctcatct gcaaaatccc    720
agaaggagac aagaaggacc aggtggttc tggcagcacc agcggggcta gcagcccacc    780
agcccccggc cgcccagtgc cttgcatctc cctttctcca ggacccgtac ttgaaccgga    840
agcactgcat ccccacgc tcatgaccac accctctctg actcctttta ctccgagtct    900
ggttttcacc tatcctagca caccagaacc ttgctcctcc actcaccgaa agagtagcag    960
cagcagtggc gacccctcct ccgaccccct gggctctcct acactcctgg ctttgtgagg   1020
cacccagcca catc                                                    1034

<210> SEQ ID NO 21
<211> LENGTH: 19
<212> TYPE: RNA
<213> ORGANISM: Artificial
<220> FEATURE:
<223> OTHER INFORMATION: siRNA sequence

<400> SEQUENCE: 21
ugaaugacau gccgaucua                                                 19

<210> SEQ ID NO 22
<211> LENGTH: 19
<212> TYPE: RNA
<213> ORGANISM: Artificial
<220> FEATURE:
<223> OTHER INFORMATION: siRNA sequence

<400> SEQUENCE: 22
uagaucggca ugucauuca                                                 19
```